(12) United States Patent
Tori et al.

(10) Patent No.: US 11,479,806 B2
(45) Date of Patent: Oct. 25, 2022

(54) METHODS OF PRODUCING AMPLIFIED DOUBLE STRANDED DEOXYRIBONUCLEIC ACIDS AND COMPOSITIONS AND KITS FOR USE THEREIN

(71) Applicant: TAKARA BIO USA, INC., Mountain View, CA (US)

(72) Inventors: Kazuo Tori, Mountain View, CA (US); Magnolia Bostick, San Mateo, CA (US); Andrew Farmer, Los Altos, CA (US)

(73) Assignee: Takara Bio USA, Inc., San Jose, CA (US)

( * ) Notice: Subject to any disclaimer, the term of this patent is extended or adjusted under 35 U.S.C. 154(b) by 320 days.

(21) Appl. No.: 16/321,418

(22) PCT Filed: Nov. 8, 2017

(86) PCT No.: PCT/US2017/060717
§ 371 (c)(1),
(2) Date: Jan. 28, 2019

(87) PCT Pub. No.: WO2018/089550
PCT Pub. Date: May 17, 2018

(65) Prior Publication Data
US 2021/0062243 A1    Mar. 4, 2021

Related U.S. Application Data

(60) Provisional application No. 62/420,503, filed on Nov. 10, 2016.

(51) Int. Cl.
| | | |
|---|---|---|
| *C12Q 1/68* | (2018.01) | |
| *C12Q 1/6806* | (2018.01) | |
| *C12N 15/10* | (2006.01) | |
| *C12Q 1/6844* | (2018.01) | |

(52) U.S. Cl.
CPC ....... *C12Q 1/6806* (2013.01); *C12N 15/1096* (2013.01); *C12Q 1/6844* (2013.01); *C12Q 2521/107* (2013.01); *C12Q 2525/155* (2013.01); *C12Q 2525/161* (2013.01); *C12Q 2525/173* (2013.01); *C12Q 2525/179* (2013.01); *C12Q 2535/122* (2013.01); *C12Q 2563/149* (2013.01)

(58) Field of Classification Search
None
See application file for complete search history.

(56) References Cited

U.S. PATENT DOCUMENTS

| | | | |
|---|---|---|---|
| 2014/0004569 A1 | 1/2014 | Lambowitz et al. | |
| 2014/0113332 A1* | 4/2014 | Betts | C12Q 1/6853 435/91.5 |
| 2015/0307874 A1 | 10/2015 | Jaitin et al. | |
| 2015/0329891 A1 | 11/2015 | Tan et al. | |
| 2016/0258016 A1 | 9/2016 | Sandberg et al. | |

FOREIGN PATENT DOCUMENTS

| | | | |
|---|---|---|---|
| WO | WO 2012148497 A2 | 4/2012 | |
| WO | WO 2012116146 A1 | 8/2012 | |
| WO | WO-2016126871 A2 * | 8/2016 | ............ B01F 5/0655 |
| WO | WO 2016126871 A2 | 8/2016 | |
| WO | WO2017222057 A1 | 12/2017 | |

OTHER PUBLICATIONS

Zhu et al. Reverse Transcriptase template switching: A SMART approach for full-length cDNA library construction. Biotechniques, vol. 30, p. 892-897, 2001.*
Clontech Laboratories, Inc. "SMARTer™ PCR cDNA Synthesis Kit User Manual", www.clontech.com, pp. 1-30, 2014.
Clontech Laboratories, Inc. "DNA Smart™ ChIP-Seq Kit User Manual", www.clontech.com, pp. 1-23, 2016.
Clontech Laboratories, Inc. "Be SMART™ About First-Strand cDNA Synthesis", www.clontech.com, pp. 1-3, 2009.
Clontech Laboratories, Inc. "High Yield PCR EcoDry™ Premix Protocol-At-A-Glance (PT5151-2)", www.clontech.com, 1 page, 2013.
Clontech Laboratories, Inc. "Titanium® One-Step RT-PCR Kit User Manual", www.clontech.com, 10 pages, 2011.
Clontech Laboratories, Inc. "Titanium® One-Step RT-PCR Kit Protocol", www.clontech.com, 2 pages, 2011.
Clontech Laboratories, Inc. "SMARTScribe™ Reverse Transcriptase Protocol-At-A-Glance", www.clontech.com, 2 pages, 2015.
Takara Bio, Inc. "Takara PrimeScript™ RT-PCR Kit", Cat. # RR014A, www.takara-bio.com, 11 pages, downloaded Mar. 2019.
Takara Bio, Inc. "Takara PrimeScript™ One Step RT-PCR Kit Ver.2", Cat. # RR055A, www.takara-bio.com, 11 pages, downloaded Mar. 2019.
Eastburn, et al. "Microfluidic droplet enrichment for targeted sequencing", Nucleic Acids Research, 2015, 8 pages.
Freeman, et al. "Profiling the T-cell receptor beta-chain repertoire by massively parallel sequencing", Genome Research, 19:1817-1824, 2009.
Kapyeyn, et al. "Incorporation of non-natural nucleotides into template-switching oligonucleotides reduces background and improves cDNA synthesis from very small RNA samples", BMC Genomics 2010, 11:413.
Martin, et al. "RNA-specific ribonucleotidyl transferases", RNA (2007), 13:1834-1849.
Zhang, et al. "Isolation and Analysis of Rare Norovirus Recombinants from Coinfected Mice Using Drop-Based Microfluidics", Journal of Virology, Aug. 2015 vol. 89 No. 15, 13 pages.

(Continued)

*Primary Examiner* — Suryaprabha Chunduru
(74) *Attorney, Agent, or Firm* — Bret E. Field; Bozicevic, Field & Francis LLP

(57) ABSTRACT

Methods of producing an amplified double stranded deoxyribonucleic acid (dsDNA) from a nucleic acid sample are provided. Aspects of the methods include amplifying using a single product nucleic acid primer and a template switch oligonucleotide to produce an amplified dsDNA product. Compositions and kits for use in performing the methods are also provided.

14 Claims, 21 Drawing Sheets
Specification includes a Sequence Listing.

(56) References Cited

OTHER PUBLICATIONS

Zhu, et al. "Reverse Transcriptase Template Switching: A SMART Approach for Full-Length cDNA Library Construction", BioTechniques 30:892-897 (Apr. 2001).

\* cited by examiner

FIG. 8
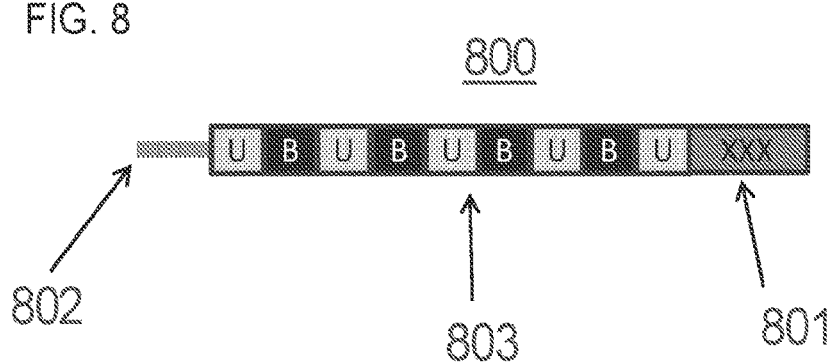
FIG. 9
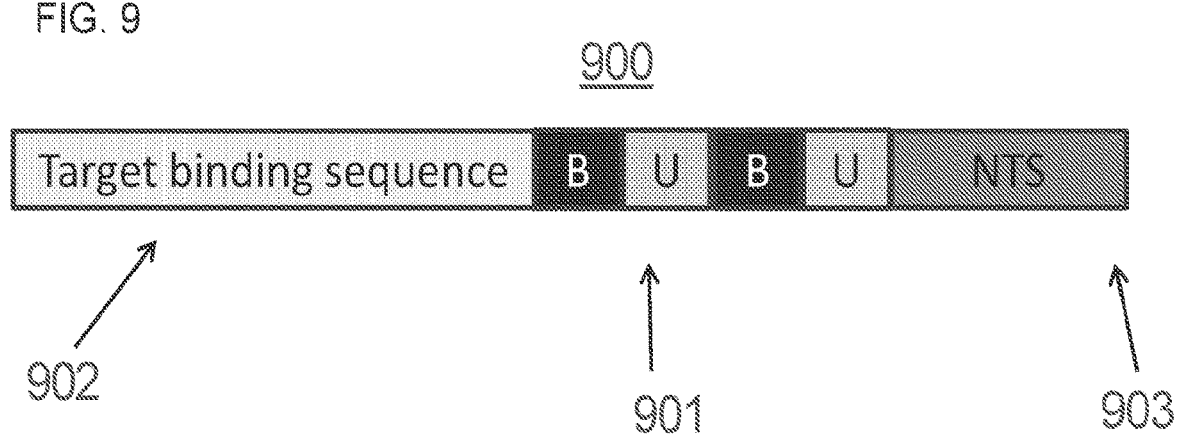
FIG. 10
Scheme Code    BUMI
CATBBUUBUBU
CAABUUBBUBU
CTABUBUBUBU
TACBUBBUBUB FIG. 11
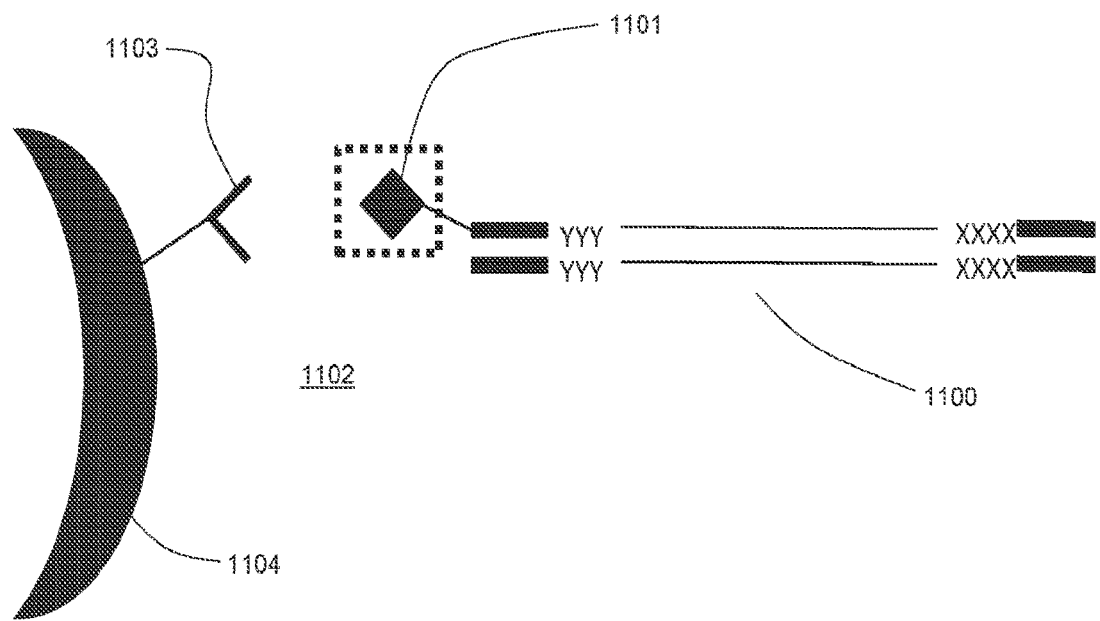
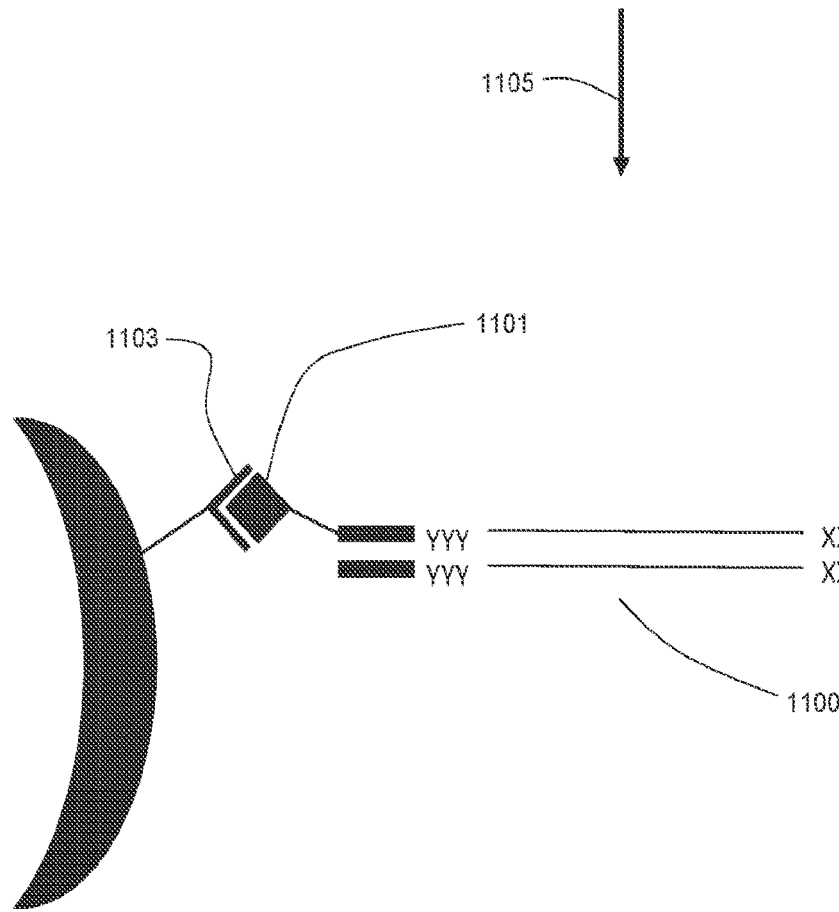

FIG. 18
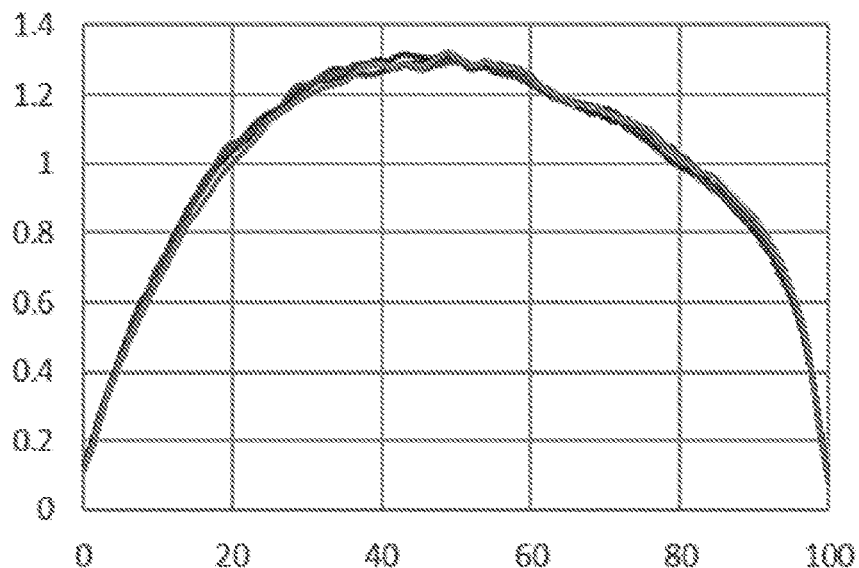
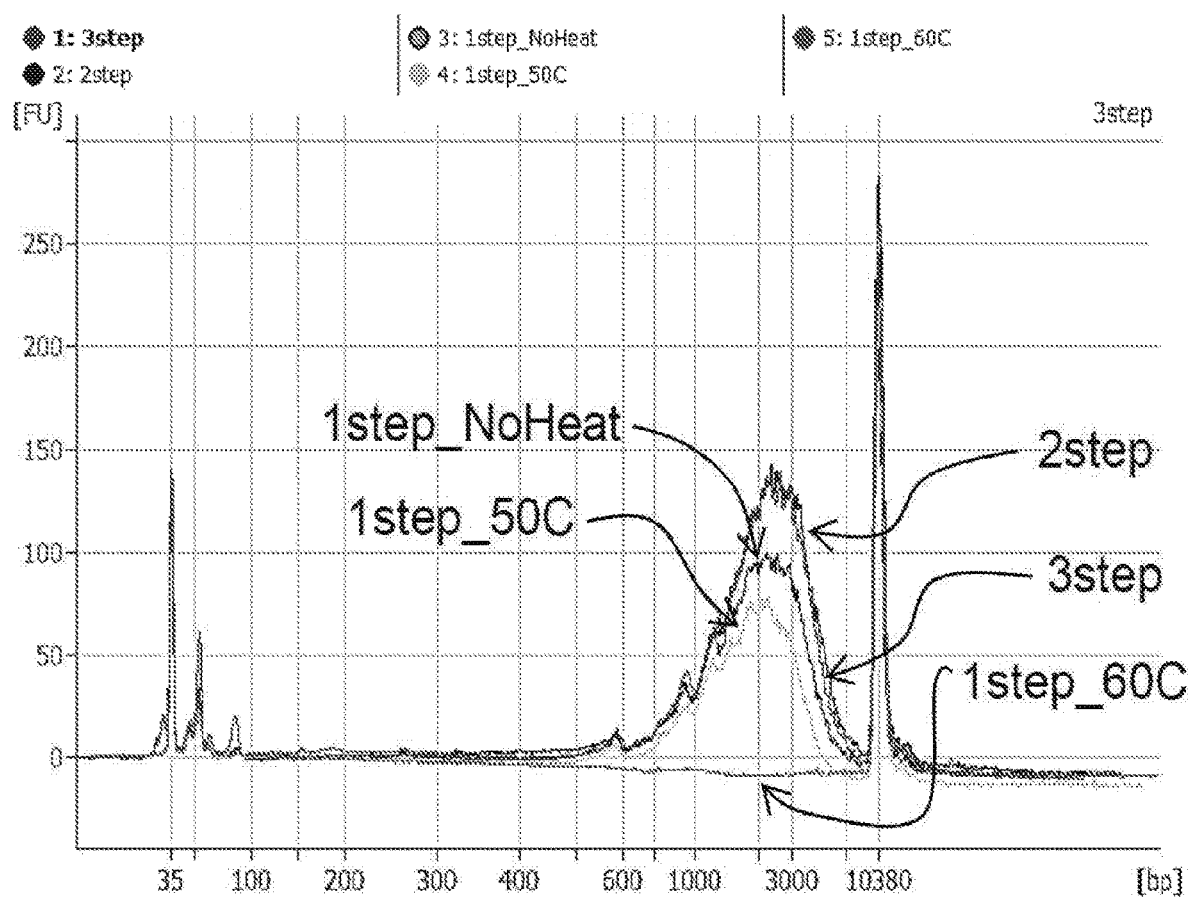

FIG. 19

Sequencing metrics comparing SMART-Seq v4 and SMART-Seq HT kits

| RNA source | | 10 pg Mouse Brain Total RNA | | | | | |
|---|---|---|---|---|---|---|---|
| cDNA synthesis | | SMART-Seq v4 | | | SMART-Seq HT | | |
| Replicate | | A | B | C | A | B | C |
| Yield (ng) | | 7.3 | 8.5 | 9.4 | 9.5 | 9.9 | 9.2 |
| Number of transcripts | FPKM >0.1 | 14,168 | 13,934 | 14,147 | 14,510 | 14,650 | 14,553 |
| | FPKM >1 | 11,455 | 11,267 | 11,349 | 11,582 | 11,670 | 11,454 |
| Average Pearson/Spearman | | 0.97/0.67 | | | 0.97/0.68 | | |
| | | | | 0.96/0.66 | | | |
| Proportion of reads mapped (%): | | | | | | | |
| rRNA | | 0.7 | 0.6 | 0.5 | 1.1 | 1.1 | 1.1 |
| Mitochondria | | 2.8 | 4.2 | 4.1 | 3.7 | 3.8 | 4.2 |
| Genome | | 92.3 | 90.8 | 86.6 | 89.1 | 89.0 | 87.8 |
| Exons | | 74.8 | 72.5 | 69.0 | 67.3 | 67.1 | 65.3 |
| Introns | | 13.3 | 14.1 | 13.3 | 16.9 | 16.9 | 17.4 |
| Intergenic regions | | 4.2 | 4.2 | 4.4 | 4.9 | 5.0 | 5.2 |

FIG. 21

| | Gene GC content representation for SMART-Seq v4 and SMART-Seq HT kits | | | | |
|---|---|---|---|---|---|
| | Number of genes identified (% of total) | | | Total genes identified | |
| | GC content ≤36% | GC content 37-54% | GC content ≥55% | GC content 0-100% | |
| SMART-Seq HT Kit | 272 (2.1) | 11,788 (90.6) | 954 (7.3) | 13,014 | |
| SMART-Seq v4 kit | 280 (2.2) | 11,540 (90.4) | 943 (7.4) | 12,764 | |
| Reference genome | 1,665 (4.7) | 31,916 (89.9) | 1,914 (5.4) | 35,495 | |

FIG. 23

| RNA source | 293T single cells | | | | | |
|---|---|---|---|---|---|---|
| cDNA synthesis | SMART-Seq v4 (n=12) | | | SMART-Seq HT (n=9) | | |
| | | Average | St. dev. | | Average | St. dev. |
| Number of transcripts | FPKM >0.1 | 12,241 | 2,132 | | 12,840 | 2,937 |
| | FPKM >1 | 9,110 | 1,468 | | 9,459 | 1,848 |
| Proportion of reads mapped (%): | | | | | | |
| rRNA | | 0.1 | 0.04 | | 0.3 | 0.1 |
| Mitochondria | | 2.7 | 0.6 | | 4.2 | 1.3 |
| Genome | | 95.1 | 0.6 | | 93.1 | 1.4 |
| Exons | | 87.8 | 1.3 | | 83.1 | 4.0 |
| Introns | | 5.4 | 0.9 | | 7.6 | 2.7 |
| Intergenic regions | | 1.9 | 0.2 | | 2.5 | 0.5 |

Sequencing metrics comparing SMART-Seq v4 and SMART-Seq HT kits

SEQUENCE LISTING

<160> NUMBER OF SEQ ID NOS: 6

<210> SEQ ID NO 1
<211> LENGTH: 20
<212> TYPE: DNA
<213> ORGANISM: Artificial Sequence
<220> FEATURE:
<223> OTHER INFORMATION: synthetic polynucleotide sequence

<400> SEQUENCE: 1

```
aatgatacgg cgaccaccga                                              20

<210> SEQ ID NO 2
<211> LENGTH: 24
<212> TYPE: DNA
<213> ORGANISM: Artificial Sequence
<220> FEATURE:
<223> OTHER INFORMATION: synthetic polynucleotide sequence

<400> SEQUENCE: 2
caagcagaag acggcatacg agat                                         24

<210> SEQ ID NO 3
<211> LENGTH: 33
<212> TYPE: DNA
<213> ORGANISM: Artificial Sequence
<220> FEATURE:
<223> OTHER INFORMATION: synthetic polynucleotide sequence

<400> SEQUENCE: 3
acactctttc cctacacgac gctcttccga tct                               33

<210> SEQ ID NO 4
<211> LENGTH: 34
<212> TYPE: DNA
<213> ORGANISM: Artificial Sequence
<220> FEATURE:
<223> OTHER INFORMATION: synthetic polynucleotide sequence

<400> SEQUENCE: 4
gtgactggag ttcagacgtg tgctcttccg atct                              34

<210> SEQ ID NO 5
<211> LENGTH: 30
<212> TYPE: DNA
<213> ORGANISM: Artificial Sequence
<220> FEATURE:
<223> OTHER INFORMATION: synthetic polynucleotide sequence

<400> SEQUENCE: 5
ccatctcatc cctgcgtgtc tccgactcag                                   30

<210> SEQ ID NO 6
<211> LENGTH: 23
<212> TYPE: DNA
<213> ORGANISM: Artificial Sequence
<220> FEATURE:
<223> OTHER INFORMATION: synthetic polynucleotide sequence

<400> SEQUENCE: 6
cctctctatg ggcagtcggt gat                                          23
```

METHODS OF PRODUCING AMPLIFIED DOUBLE STRANDED DEOXYRIBONUCLEIC ACIDS AND COMPOSITIONS AND KITS FOR USE THEREIN

CROSS REFERENCE TO RELATED APPLICATIONS

Pursuant to 35 U.S.C. § 119(e), this application claims priority to the filing date of the U.S. Provisional Patent Application Ser. No. 62/420,503, filed Nov. 10, 2016; the disclosure of which application is herein incorporated by reference.

INTRODUCTION

Reverse transcription coupled with polymerase chain reaction amplification, also known as RT-PCR, is one of the most powerful RNA detection techniques available to researchers and clinicians alike. RT-PCR is an exemplary process for producing amplified double stranded complementary deoxyribonucleic acids (cDNAs) from a starting sample of RNAs that can be used for various purposes including simple detection and quantification or as the raw material for downstream bio-engineering and bioinformatics endeavors. RT-PCR represents a significant step forward as compared to earlier techniques for RNA exploration including, e.g., Northern blot analysis and RNase protection assays. The advent of RT-PCR allowed for the more rapid detection and/or quantification of RNAs of interest while also allowing researchers to use smaller samples or samples containing smaller quantities of RNA, including quantities as small as those obtained from a single cell. With the further advancement of next generation sequencing technologies, the end result of a RT-PCR reaction, namely a population of amplified cDNAs, can now be quickly and effectively processed for massive amounts of potent scientific data.

Techniques involving the production of double-stranded DNA (dsDNA) products having added stretches of known nucleic acid sequence have proven to be similarly powerful in many biotechnology and biomedical research applications. For example, template switching, which allows for the production of product dsDNA from DNA templates of entirely unknown sequence while attaching regions of known sequence to the produced dsDNA, has been applied to nucleic acid barcoding and library generation in various sequencing approaches.

Given the widespread adoption of these powerful techniques, improvements to dsDNA production, RT-PCR, and related methods, stand to have a huge impact on the pace of research in many realms, especially biomedical technology. Enhancements, such as, reducing protocol length, reducing operator time, reducing opportunities for reaction contamination, increasing reaction specificity and increasing reaction precision, among others, would be immensely valuable.

SUMMARY

Methods of producing an amplified double stranded deoxyribonucleic acid (dsDNA) from a nucleic acid sample are provided. Aspects of the methods include amplifying using a single product nucleic acid primer and a template switch oligonucleotide to produce an amplified dsDNA product. Compositions and kits for use in performing the methods are also provided.

BRIEF DESCRIPTION OF THE FIGURES

FIG. 8 provides a schematic of a template switch oligonucleotide containing a BUMI domain according to an embodiment of the present disclosure described herein.

FIG. 9 provides a schematic of a primer containing a BUMI domain according to an embodiment of the present disclosure described herein.

FIG. 10 provides examples of encoded BUMI domains as described herein.

FIG. 11 provides an example of the capture of a produced dsDNA using a caged capture moiety attached to the template switching oligonucleotide according to one embodiment of the present disclosure.

FIG. 18 demonstrates similar gene body coverage and production of appropriately sized libraries using various reduced-step methods of the present disclosure as compared to a three-step method.

FIG. 19 demonstrates that the SMART-Seq HT Kit provides the same sensitivity and reproducibility as the SMART-Seq v4 kit.

FIG. 21 demonstrates, using the three-step method as a baseline reference, that there is no additional GC content representation bias in the reduced-step method.

FIG. 23 demonstrates that RNA-seq libraries generated from individual cells using SMART-Seq v4 or SMART-Seq HT kits have similar sequencing metrics.

DEFINITIONS

Figure 1:
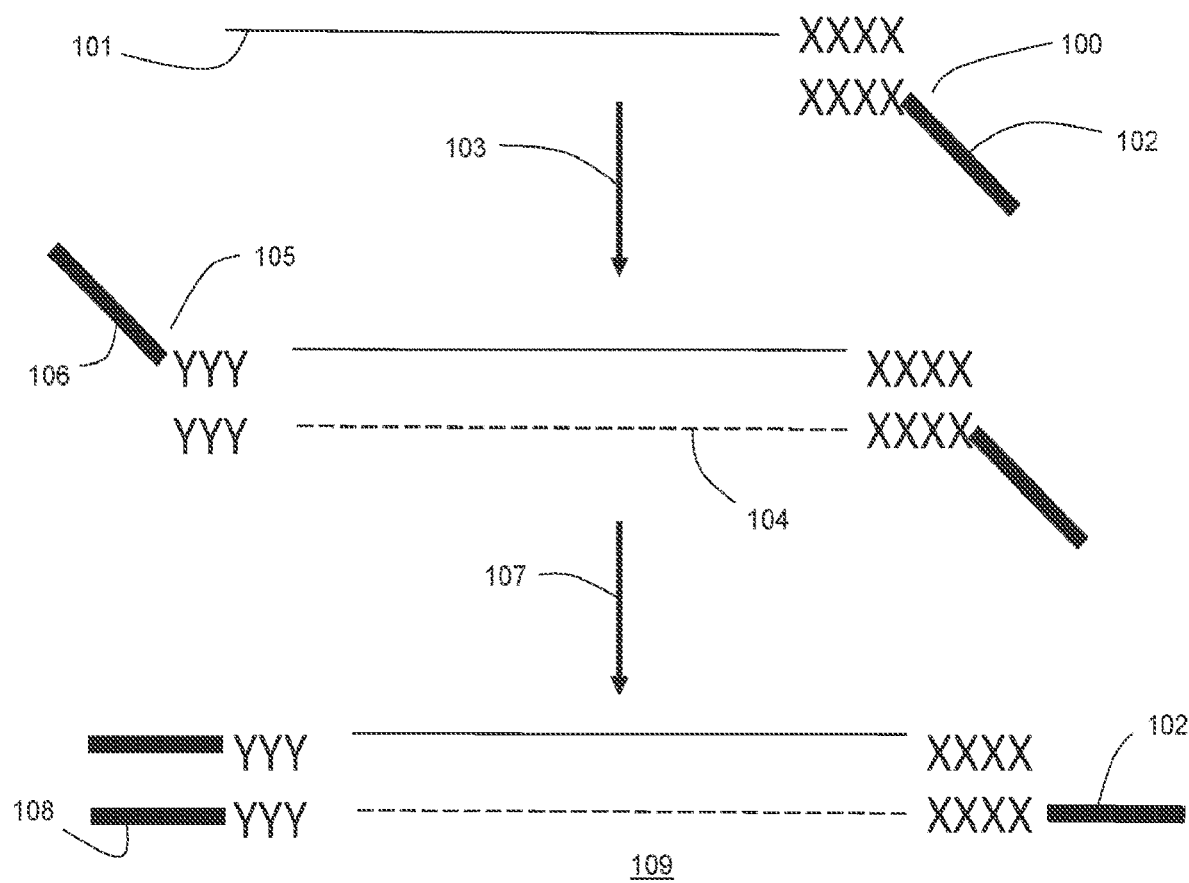
FIG. 1 provides a schematic representation of single product nucleic acid synthesis using template switching.

As used herein, the term "hybridization conditions" means conditions in which a primer, or other polynucleotide, specifically hybridizes to a region of a target nucleic acid with which the primer or other polynucleotide shares some complementarity. Whether a primer specifically hybridizes to a target nucleic acid is determined by such factors as the degree of complementarity between the polymer and the target nucleic acid and the temperature at which the hybridization occurs, which may be informed by the melting temperature ($T_M$) of the primer. The melting temperature refers to the temperature at which half of the primer-target nucleic acid duplexes remain hybridized and half of the duplexes dissociate into single strands. The Tm of a duplex may be experimentally determined or predicted using the following formula Tm=81.5+16.6(log 10[Na+])+0.41 (fraction G+C)−(60/N), where N is the chain length and [Na+] is less than 1 M. See Sambrook and Russell (2001; Molecular Cloning: A Laboratory Manual, 3rd ed., Cold Spring Harbor Press, Cold Spring Harbor N.Y., Ch. 10). Other more advanced models that depend on various parameters may also be used to predict Tm of primer/target duplexes depending on various hybridization conditions. Approaches for achieving specific nucleic acid hybridization may be found in, e.g., Tijssen, Laboratory Techniques in Biochemistry and Molecular Biology-Hybridization with Nucleic Acid Probes, part I, chapter 2, "Overview of principles of hybridization and the strategy of nucleic acid probe assays," Elsevier (1993).

The terms "complementary" and "complementarity" as used herein refer to a nucleotide sequence that base-pairs by non-covalent bonds to all or a region of a target nucleic acid (e.g., a region of the product nucleic acid). In the canonical Watson-Crick base pairing, adenine (A) forms a base pair with thymine (T), as does guanine (G) with cytosine (C) in DNA. In RNA, thymine is replaced by uracil (U). As such, A is complementary to T and G is complementary to C. In RNA, A is complementary to U and vice versa. Typically, "complementary" refers to a nucleotide sequence that is at least partially complementary. The term "complementary" may also encompass duplexes that are fully complementary such that every nucleotide in one strand is complementary to every nucleotide in the other strand in corresponding positions. In certain cases, a nucleotide sequence may be partially complementary to a target, in which not all nucleotides are complementary to every nucleotide in the target nucleic acid in all the corresponding positions. For example, a primer may be perfectly (i.e., 100%) complementary to the target nucleic acid, or the primer and the target nucleic acid may share some degree of complementarity that is less than perfect (e.g., 70%, 75%, 85%, 90%, 95%, 99%).

The percent identity of two nucleotide sequences can be determined by aligning the sequences for optimal comparison purposes (e.g., gaps can be introduced in the sequence of a first sequence for optimal alignment). The nucleotides at corresponding positions are then compared, and the percent identity between the two sequences is a function of the number of identical positions shared by the sequences (i.e., % identity=# of identical positions/total # of positions× 100). When a position in one sequence is occupied by the same nucleotide as the corresponding position in the other sequence, then the molecules are identical at that position. A non-limiting example of such a mathematical algorithm is described in Karlin et al., Proc. Natl. Acad. Sci. USA 90:5873-5877 (1993). Such an algorithm is incorporated into the NBLAST and XBLAST programs (version 2.0) as described in Altschul et al., Nucleic Acids Res. 25:389-3402 (1997). When utilizing BLAST and Gapped BLAST programs, the default parameters of the respective programs (e.g., NBLAST) can be used. In one aspect, parameters for sequence comparison can be set at score=100, wordlength=12, or can be varied (e.g., wordlength=5 or wordlength=20).

A domain refers to a stretch or length of a nucleic acid made up of a plurality of nucleotides, where the stretch or length provides a defined function to the nucleic acid. Examples of domains include Barcoded Unique Molecular Identifier (BUMI) domains, primer binding domains, hybridization domains, barcode domains (such as source barcode domains), unique molecular identifier (UMI) domains, Next Generation Sequencing (NGS) adaptor domains, NGS indexing domains, etc. While the length of a given domain may vary, in some instances the length ranges from 2 to 100 nt, such as 5 to 50 nt, e.g., 5 to 30 nt.

As described in greater detail below, BUMI domains are domains that include at least a portion of a BUMI tag. A given BUMI domain may include a complete BUMI tag, and be coextensive with a BUMI tag. In other instances, a BUMI domain may include a portion of a BUMI tag. In either of these instances, a BUMI domain may further include a BUMI encoding component, which provides the coding information for a BUMI tag or portion thereof that is present in the BUMI Domain.

DETAILED DESCRIPTION

Methods of producing an amplified double stranded deoxyribonucleic acid (dsDNA) from a nucleic acid sample are provided. Aspects of the methods include amplifying using a single product nucleic acid primer and a template switch oligonucleotide to produce an amplified dsDNA product. Compositions and kits for use in performing the methods are also provided.

Before the methods of the present disclosure are described in greater detail, it is to be understood that the methods are not limited to particular embodiments described, as such may, of course, vary. It is also to be understood that the terminology used herein is for the purpose of describing particular embodiments only, and is not intended to be limiting, since the scope of the methods will be limited only by the appended claims.

Where a range of values is provided, it is understood that each intervening value, to the tenth of the unit of the lower limit unless the context clearly dictates otherwise, between the upper and lower limit of that range and any other stated or intervening value in that stated range, is encompassed within the methods. The upper and lower limits of these smaller ranges may independently be included in the smaller ranges and are also encompassed within the methods, subject to any specifically excluded limit in the stated range. Where the stated range includes one or both of the limits, ranges excluding either or both of those included limits are also included in the methods.

Certain ranges are presented herein with numerical values being preceded by the term "about." The term "about" is used herein to provide literal support for the exact number that it precedes, as well as a number that is near to or approximately the number that the term precedes. In determining whether a number is near to or approximately a specifically recited number, the near or approximating unrecited number may be a number which, in the context in which it is presented, provides the substantial equivalent of the specifically recited number.

Unless defined otherwise, all technical and scientific terms used herein have the same meaning as commonly understood by one of ordinary skill in the art to which the methods belong. Although any methods similar or equivalent to those described herein can also be used in the practice or testing of the methods, representative illustrative methods and materials are now described.

All publications and patents cited in this specification are herein incorporated by reference as if each individual publication or patent were specifically and individually indicated to be incorporated by reference and are incorporated herein by reference to disclose and describe the methods and/or materials in connection with which the publications are cited. The citation of any publication is for its disclosure prior to the filing date and should not be construed as an admission that the present methods are not entitled to antedate such publication by virtue of prior invention. Further, the dates of publication provided may be different from the actual publication dates which may need to be independently confirmed.

It is noted that, as used herein and in the appended claims, the singular forms "a", "an", and "the" include plural referents unless the context clearly dictates otherwise.

It is further noted that the claims may be drafted to exclude any optional element. As such, this statement is intended to serve as antecedent basis for use of such exclusive terminology as "solely," "only" and the like in connection with the recitation of claim elements, or use of a "negative" limitation.

It is appreciated that certain features of the methods, which are, for clarity, described in the context of separate embodiments, may also be provided in combination in a single embodiment. Conversely, various features of the methods, which are, for brevity, described in the context of a single embodiment, may also be provided separately or in any suitable sub-combination. All combinations of the embodiments are specifically embraced by the present invention and are disclosed herein just as if each and every combination was individually and explicitly disclosed, to the extent that such combinations embrace operable processes and/or devices/systems/kits. In addition, all sub-combinations listed in the embodiments describing such variables are also specifically embraced by the present methods and are disclosed herein just as if each and every such sub-combination was individually and explicitly disclosed herein.

As will be apparent to those of skill in the art upon reading this disclosure, each of the individual embodiments described and illustrated herein has discrete components and features which may be readily separated from or combined with the features of any of the other several embodiments without departing from the scope or spirit of the present methods. Any recited method can be carried out in the order of events recited or in any other order which is logically possible.

Methods

As summarized above, aspects of the present disclosure include producing an amplified double stranded deoxyribonucleic acid (dsDNA). The present methods include amplifying from a template nucleic acid using a single product nucleic acid primer and a template switch oligonucleotide. In some instances, such primers used in amplifying from the single product nucleic acid may be the same primers used in producing the single product nucleic acid, e.g., in a reverse transcription reaction from a nucleic acid template. As used herein, the terms "reverse transcription" and "reverse transcription reaction" will generally refer to any reaction where a reverse transcriptase is used in a nucleic acid synthesis reaction regardless of the nature of the nucleic acid template being transcribed (e.g., regardless of whether a DNA or RNA template is processed by the reverse transcriptase to synthesize a nucleic acid complementary to the template).

By "amplified dsDNA" is meant a population of double stranded DNA copies of a single stranded single product nucleic acid. "Single product nucleic acids" will vary and may include e.g., a single stranded first strand cDNA produced from a ribonucleic acid (RNA) template or a first single stranded DNA (ssDNA) strand produced from a DNA template. Accordingly, the single product nucleic acid may be produced from a DNA-template or a non-DNA template, e.g., a RNA template. The degree of amplification, and thus the size of the produced population of dsDNA copies, will vary but in some instances is 5× amplification or more, where e.g., "5× amplification or more" refers to the production of 5 or more dsDNAs from each single product nucleic acid molecule. The degree of amplification achieved may exceed 5× amplification and may include, but is not limited to, e.g., 10× amplification or more, 100× amplification or more, 1000× amplification or more, 10,000× amplification or more, 100,000× amplification or more, 1,000,000× amplification or more, etc.

Measures of the degree of amplification need not necessarily be exact and may, e.g., be based on the average or the approximate average of a sample, where e.g., 10× amplification refers to the production of 10 dsDNAs or approximately 10 dsDNAs on average from each single product nucleic acid molecule. In some instances, the degree of amplification and/or the size of the produced population of dsDNA copies may be indirectly quantified, e.g., where the amount of DNA present in the reaction following amplification is measured and the degree of amplification is extrapolated therefrom. In some instances, the degree of amplification and/or the size of the produced population of dsDNA copies may be directly quantified, e.g., by directly measuring the number of produced dsDNA copies using any convenient approach including e.g., quantitative sequencing methods or Bioanalyzer (e.g., Agilent Bioanalyzer).

In general, amplification, as used herein, will not refer to the production of single product nucleic acid, e.g., from a template nucleic acid. Amplification will generally include the production of more than a small number of copies, e.g., more than a single copy, of dsDNA from a single product nucleic acid, including but not limited to e.g., more than 2 copies, more than 3 copies, more than 4 copies, more than 5 copies, more than 10 copies, more than 15 copies, more than 20 copies, more than 30 copies, more than 100 copies, more than 1,000 copies, more than 10,000 copies, more than 100,000 copies, more than $10^6$ copies, more than $10^7$ copies, more than $10^8$ copies, etc. Amplification, according to the herein described methods, may be exponential or approximately exponential.

The present methods may make use of a template switch oligonucleotide in the amplification process. A template switch oligonucleotide is an oligonucleotide utilized in a template switching reaction, including the production of a single product nucleic acid from a template nucleic acid, e.g., reverse transcription of a RNA template or reverse transcription of a DNA template. As such, production of a single product nucleic acid may utilize template switching and the ability of certain nucleic acid polymerases to "template switch" i.e., use a first nucleic acid strand as a template for polymerization, and then switch to a second template nucleic acid strand (which may be referred to as a "template switch nucleic acid" or an "acceptor template") while continuing the polymerization reaction. The result is the synthesis of a hybrid nucleic acid strand with a 5' region complementary to the first template nucleic acid strand and a 3' region complementary to the template switch nucleic acid. The methods of the present disclosure may make use of a template switch oligonucleotide in production of a single product nucleic acid by template switching and the template switch oligonucleotide may be further utilized in amplification of the single product nucleic acid.

Turning to FIG. 1, a schematized example of a template switching reaction is depicted. In the embodiment shown, a single product nucleic acid primer (100) hybridizes to a template nucleic acid (101) through complementary sequence (represented by "XXXX") shared by the single product nucleic acid primer and the template. The single product nucleic acid primer may, but need not necessarily, include a region of additional sequence (102) that is not complementary to the template (e.g., non-templated). Following annealing of the single product nucleic acid primer to the template, reverse transcription (103) proceeds, through the use of a reverse transcriptase, to generate a single product nucleic acid strand (104) that is complementary to the template. The reverse transcriptase, having terminal transferase activity, transfers non-templated nucleotides to the generated single product nucleic acid (represented by "YYY") and a template switching oligonucleotide (105) hybridizes to the non-templated nucleotides of the single product nucleic acid by a sequence of complementary nucleotides (also represented by "YYY" and also referred to herein as a 3' hybridization domain) present on the template switch oligonucleotide. The template switch oligonucleotide includes additional sequence (106) that does not hybridize to the non-templated nucleotides. Template switching occurs (107), wherein the reverse transcriptase switches from the template to utilize the template switching oligonucleotide as a second template, transcribing the additional sequence (106) to generate its complement (108). The now fully generated single product nucleic acid strand (109) includes the complete sequence of the single product nucleic acid primer, including any additional sequence (102), if present, that did not hybridize to the template, the complementary sequence of the template and the complementary sequence of the template switch oligonucleotide. Methods and reagents related to template switching are also described in U.S. Pat. No. 9,410,173; the disclosure of which is incorporated herein by reference in its entirety.

In some instances, the process of template switching may be limited to the production of the first strand and e.g., template switching may not occur during amplification even though the amplification reaction makes use of the template switching oligonucleotide. For example, following an initial template switching reaction during which a polymerase switches from a first nucleic acid template to the template switch oligonucleotide, e.g., as used to produce a single product nucleic acid, template switching may no longer occur when the template switch oligonucleotide is further utilized for subsequent amplification. Accordingly, in some instances, template switching does not occur when utilizing a template switch oligonucleotide in the amplification portion of a reaction, including e.g., during the amplification of a single product nucleic acid to produce amplified dsDNA product.

The subject methods may include combining, in a reaction mixture, those reaction components necessary for amplification or those reaction components necessary for both single product nucleic acid strand synthesis as well as amplification. For example, the subject methods may include combining a reverse transcriptase and an amplification polymerase in a single reaction mixture and performing both reverse transcription and amplification in the reaction mixture. Components, including e.g., those described herein, as combined in a single reaction mixture may be added, e.g., by a user, to the reaction mixture or may be provided, e.g., to a user, pre-combined in the reaction mixture.

The present methods include those having a limited number of steps. The number of "steps" used in a particular method or protocol may be determined in various ways and may, in some instances, refer to the addition or combining of components to a reaction mixture. For example, in some instances, a "three-step" protocol may include three rounds or incidences of adding one or more components to a reaction mixture, a "two-step" protocol may include two rounds or incidences of adding one or more components to a reaction mixture and a "one-step" protocol may include only one round or incidence of adding one or more components to a reaction mixture. In some instances, a temperature change may be performed between steps of adding components to a reaction mixture. For example, a reaction mixture may be preheated, and following the preheating, a second step that includes adding additional components to the reaction mixture may be performed prior to further reaction processes.

Reaction processes may be performed before, during, between or after the step(s) of a protocol having a limited number of steps. For example, in some instances, a reaction mixture may be heated before, during, between or after the step(s) of a protocol. In some instances, a reaction mixture may be subjected to one or more temperatures, temperature changes, or a thermocycling procedure before, during, between or after the step(s) of a protocol. Such, reaction processes, e.g., those that do not include adding additional components to the reaction mixture, do not constitute a method "step" as they are referred to herein regarding methods and protocols having a limited number of steps. For example, a "one-step" method where one or more components are added to a reaction mixture in a single round of "combining" and the reaction mixture is subjected to various temperature changes of a thermocycling process, the individual temperature changes are not considered "steps" as defined herein. Similarly, in a "two-step" method where one or more components are added to a reaction mixture in two separate rounds of "combining" and the reaction mixture is subjected to one or more temperature changes between the rounds of reagent addition, the one or more temperature changes between the component addition steps are not considered "steps" as defined herein.

Accordingly, the methods described herein may be performed in a limited number of steps including two steps or one step. For example, in some instances, a method described herein represents a two-step method of amplification of dsDNA. In some instances, a method described herein presents a two-step method of reverse transcription and amplification of dsDNA from template nucleic acid. In some instances, a method described herein represents a one-step method of amplification of dsDNA. In some instances, a method described herein presents a one-step method of reverse transcription and amplification of dsDNA from template nucleic acid.

Figure 2:
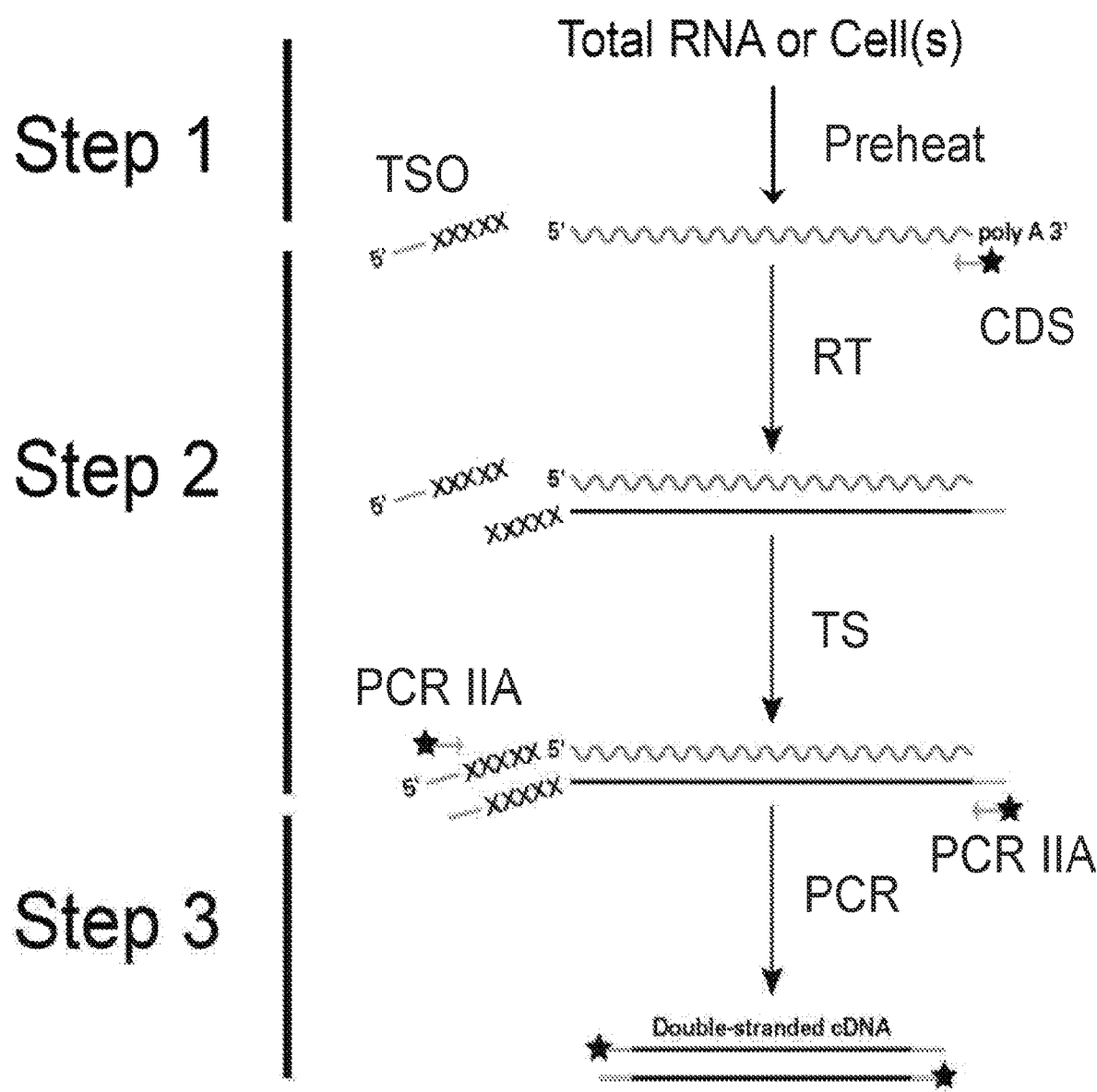
FIG. 2 provides a schematic representation of a three-step reverse transcription polymerase chain reaction (RT-PCR) protocol.

Reverse transcription polymerase chain reaction (RT-PCR) amplification methods may be performed in three steps. For example, as depicted in FIG. 2, in a first step, sample (e.g., total RNA or cells) present in a reaction vessel may be pre-heated. In some instances, one or more additional reagents may or may not be added before the subject pre-heating step, including but not limited to, e.g., RNase inhibitor, reverse transcription (RT) primer and buffer (e.g., sample lysis buffer). In some instances, one or more of such additional reagents may be added following pre-heating. In a second step, reagents necessary for RT may be added, including e.g., reverse transcriptase, RNase inhibitor, etc., and RT may be subsequently performed. In some instances, this second step may further include template-switching ("TS"), as depicted, the reagents for which may be added during and/or before this step. Next, in a third step, PCR amplification reagents may be added, including e.g., DNA polymerase, amplification primers (e.g., PCR IIA primer as depicted), etc., and PCR may be carried out. The result of this three-step process may be a double-stranded cDNA or a library thereof that may, e.g., depending on the configuration of the oligonucleotides/primers employed, include a non-templated sequence (including e.g., sequencing adapters, barcode sequence, etc.).

Figure 3:
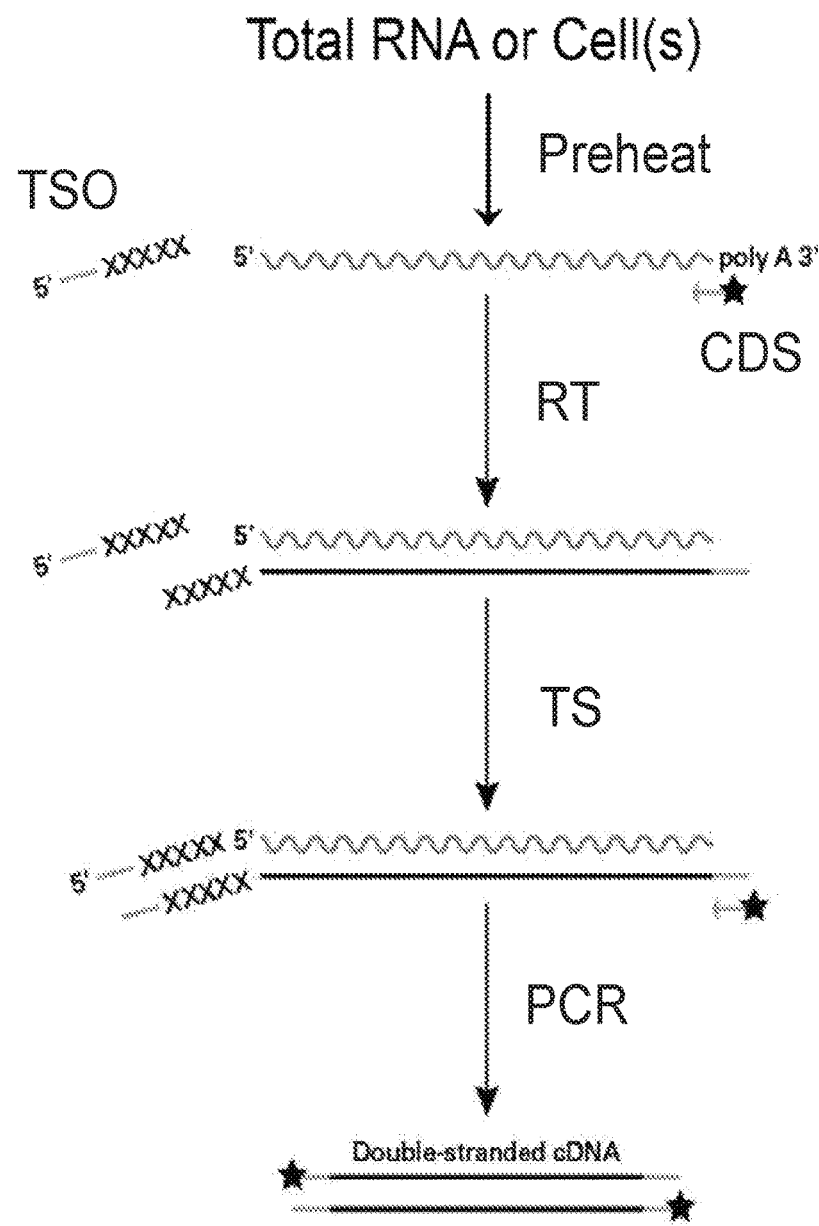
FIG. 3 provides a schematic representation of a two-step RT-PCR protocol according to one embodiment of the present disclosure.

In some embodiments of the present methods, a RT-PCR may be performed in two steps, e.g., as depicted in FIG. 3. In the first step of such a two-step method, sample (e.g., total RNA or cells) present in a reaction vessel may be pre-heated. Such a step may also include the addition of additional reagents such as, e.g., RNase inhibitor, buffer (e.g., lysis buffer), and the first strand primer (depicted as "CDS" in FIG. 3). In some embodiments of a two-step method, besides RNA of the sample, first strand primer may also be present prior to preheating. In some embodiments, of a two-step method a template switching oligonucleotide utilized in downstream steps may not be present in the reaction mixture during preheating. Next, in step two, components for both RT and PCR amplification are added to the reaction mixture, including but not limited to, e.g., reverse transcriptase, DNA polymerase, RNase inhibitor, template switch oligonucleotide (depicted at "TSO"), dNTPs, reaction buffer, etc., and RT-PCR, in some instances with template-switching ("TS"), is carried out. In some instances, a DNA polymerase that is inactive under RT reaction conditions but becomes active under amplification conditions, or at denaturation temperature, may be employed, including e.g., a hot-start DNA polymerase. The result of this two-step process may be a double-stranded cDNA or a library thereof that may, e.g., depending on the configuration of the oligonucleotides/primers employed, include a non-templated sequence (including, e.g., sequencing adapters, barcode sequence, etc.).

In the above embodiments, purification may or may not be performed. For example, in some instances, in the above embodiments no purification, e.g., of the intermediate product produced in step one, is performed. Methods of the instant disclosure may, but need not necessarily, exclude purification of reaction products (either intermediate or final). As such, in some instances, a step or processes before, during, between or after a step of a method as described herein may exclude purification. Accordingly, methods described herein may exclude purification from individual steps or from the method entirely. Excluding purification may allow for one or more reagents involved in a preceding process of the reaction mixture to be present and involved in a subsequent process. For example, a component of a RT reaction may, owing to an absence of purification, be present and involved in a later reaction, such as e.g., a PCR amplification reaction. This configuration is in comparison to where purification is employed, e.g., to remove one or more components from a reaction mixture that were employed in an initial reaction (e.g., an RT reaction) such that the one or more reagents are not present and thus not involved in a subsequent reaction (e.g., PCR amplification). Accordingly, in some instances, the absence of purification between successive reactions of a herein described method may allow for one or more components to play multiple roles in multiple different reactions of the method.

Alternatively, methods described herein may include one or more purifications, within individual steps or within the method as a whole. In some instances, methods of the instant disclosure may, but need not necessarily, include purification of reaction products (either intermediate or final). As such, in some instances, a step or processes before, during, between or after a step of a method as described herein may include a purification.

Figure 4:
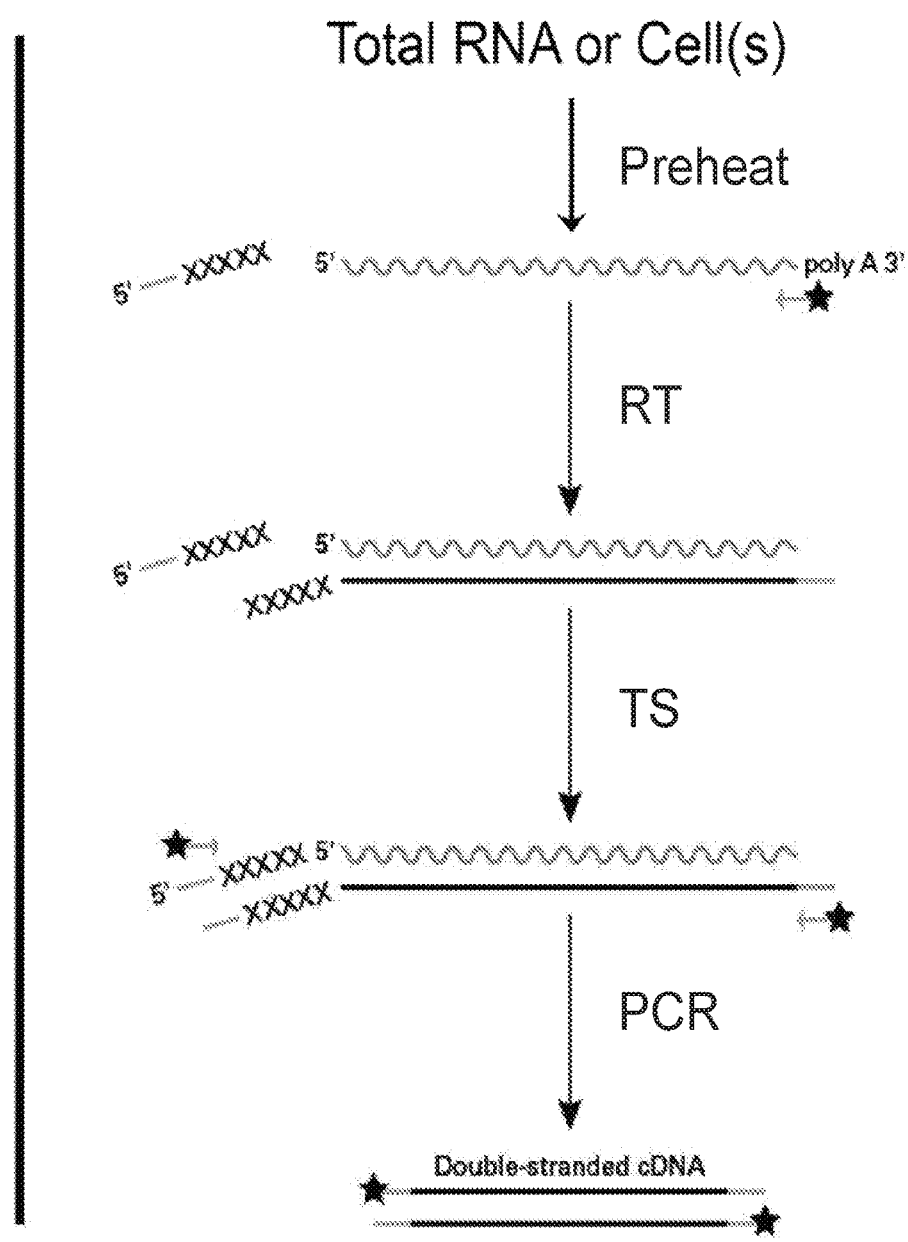
FIG. 4 provides a schematic representation of a one-step RT-PCR protocol according to one embodiment of the present disclosure.

In some embodiments of the present methods, a RT-PCR may be performed in one step, e.g., as depicted in FIG. 4. In the sole step of such a method, all of the components used in the RT reaction and the PCR amplification may be added at one instance (i.e., no other components are added at additional times or points in the reaction) such components may include but are not limited to e.g., the sample (e.g., cells or total RNA), the first strand primer (depicted with a "star" in FIG. 4), reverse transcriptase, DNA polymerase, RNase inhibitor, template switch oligonucleotide ("TSO"), dNTPs, reaction buffer, etc. In some embodiments, a sample employed in a one-step method may be a purified RNA sample. The oligonucleotides/primers added in the first step, i.e., the first strand primer and the template-switch oligonucleotide, may be utilized in the PCR amplification reaction. As such, the same oligonucleotides/primers used in generating the single product nucleic acid may be employed in amplifying the generated single product nucleic acid to produce an amplified product dsDNA (e.g., a double-stranded cDNA, as depicted). Following the combination of all necessary components in the sole step of the method, the reaction mixture may proceed through various reaction conditions including pre-heating reaction conditions, RT reaction conditions, template-switching ("TS") reaction conditions and PCR reaction conditions. In some instances, a one-step method may exclude pre-heating conditions, such that the reaction mixture is not preheated prior to starting the one step RT-PCR reaction.

In some instances, where a one-step method employs preheating conditions, such conditions may include incubation at a temperature of 50° C. or less to 70° C. or above, including but not limited to, e.g., 50° C. to 75° C., 55° C. to 75° C., 60° C. to 75° C., 65° C. to 75° C., 70° C. to 75° C., 50° C. to 70° C., 55° C. to 70° C., 60° C. to 70° C., 65° C. to 70° C., 50° C., 55° C., 60° C., 65° C., 70° C., 72° C., 75° C., less than 70° C., less than 65° C., less than 60° C., etc. The length of the incubation may vary and may range from 1 min. to 5 min. or more, including but not limited to e.g., 1 to 5 min., 1 to 3 min., 1 min., 2 min., 3 min., 4 min., 5 min., etc. In some instances, following incubation at preheating conditions, the reaction may be cooled, e.g., by placing the reaction on ice, including e.g., where the reaction is kept at cooling conditions (e.g., on ice) for some period of time, including but not limited to e.g., 1 min. or more, e.g., 1 to 2 min., 1 to 3 min., 1 min., 2 min., 3 min., etc.

Figure 5:
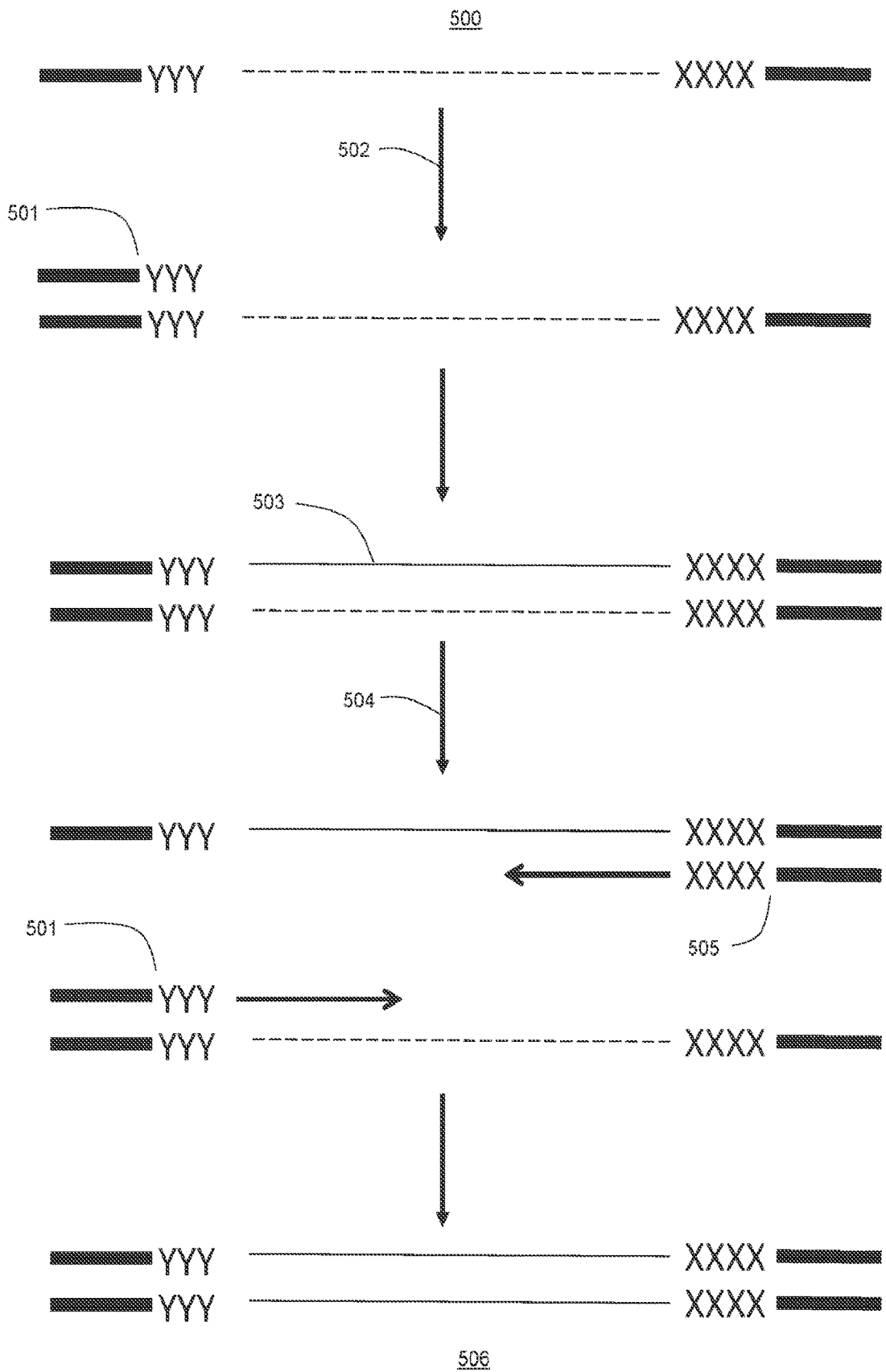
FIG. 5 depicts amplification of a single product nucleic acid using a template switch oligonucleotide and a single product nucleic acid primer according to one embodiment of the present disclosure.

As summarized above, the present methods may include the use of a template switch oligonucleotide and a first strand primer in the amplification of the first strand to generate a product double stranded nucleic acid. In some instances, the reaction utilized to produce the product double stranded nucleic acid may be a single product nucleic acid synthesis reaction utilizing template switching. Referring now to FIG. 5, starting from a single product nucleic acid (500), generated essentially as described in FIG. 1, the template switch oligonucleotide (501) is hybridized (502) to the single product nucleic acid and an amplification polymerase extends from the template switch oligonucleotide to generate a strand (503) that is complementary to the single product nucleic acid. Subsequent amplification (504) may proceed through rounds of annealing and extending the template switch oligonucleotide (501) and the first strand primer (505) (also referred to herein as the "RT primer" and the "CDS" primer, i.e., cDNA synthesis primer) to the generated strands, ultimately generating amplified dsDNA (506).

Figure 6:
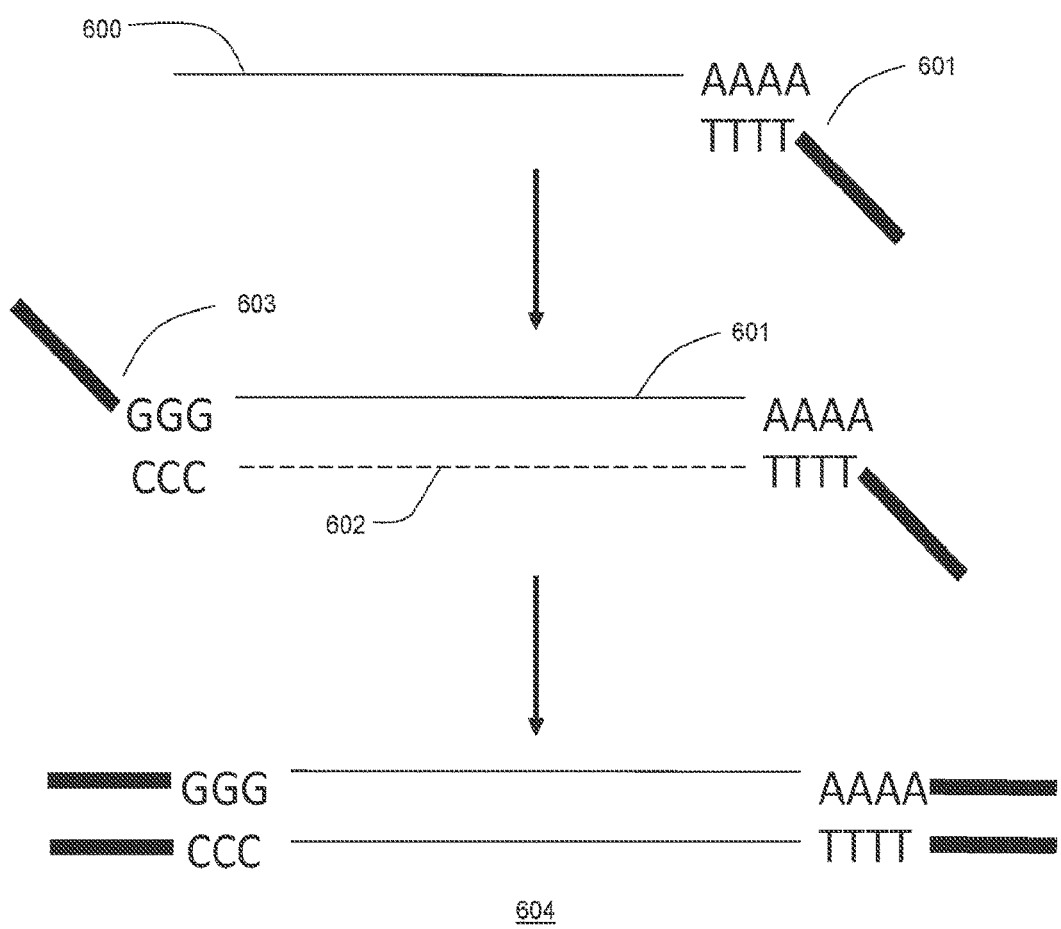
FIG. 6 depicts reverse transcription and amplification protocol from a mRNA template using a template switch oligonucleotide and a first strand cDNA primer according to one embodiment of the present disclosure.

In one embodiment, as depicted in FIG. 6, the present methods may be carried out to amplify a template mRNA (600) having a poly-A tail, using a poly-dT (also referred to as oligo(dT)) single product nucleic acid primer (601) to generate a single product nucleic acid (602) complementary to the template mRNA (601). Subsequent amplification may be carried out using a template switch oligonucleotide (603) and the single product nucleic acid primer (601), essentially as described above, to generate an amplified dsDNA product (604).

In some instances, the present methods may be carried out to amplify a template nucleic acid having a tail sequence using a single product nucleic acid primer having a sequence that is complementary to the tail sequence. The term "tail sequence", as used herein, generally refers to a polynucleotide stretch present on the 3' end of the template nucleic acid made up of a single nucleotide species (e.g., A, C, G, T, etc.). A poly(A) tail of a mRNA template is one non-limiting example of a tail sequence. Further, a poly(T) sequence present on the 3' end of a DNA template is another non-limiting example of a tail sequence. Accordingly, examples of tail sequences that may be present on a subject template nucleic acid include but are not limited to e.g., a poly(A) tail, a poly(C) tail, a poly(G) tail, a poly(T) tail, and the like. Tail sequences may range in size from less than 10 nt to 300 nt or more, including but not limited to e.g., 10 to 300 nt, 10 to 200 nt, 10 to 150 nt, 10 to 100 nt, 10 to 90 nt, 10 to 80 nt, 10 to 70 nt, 10 to 60 nt, 10 to 50 nt, 10 to 40 nt, 10 to 30 nt, 10 to 20 nt, 20 to 300 nt, 20 to 200 nt, 20 to 150 nt, 20 to 100 nt, 20 to 90 nt, 20 to 80 nt, 20 to 70 nt, 20 to 60 nt, 20 to 50 nt, 20 to 40 nt, 20 to 30 nt, 15 nt, 16 nt, 18 nt, 20 nt, etc. Where a template nucleic acid contains a tail sequence, the single product nucleic acid primer utilized in the subject methods may contain a sequence complementary to the tail sequence to which the primer hybridizes and primes elongation of the single product nucleic acid. Useful sequences complementary to the tail sequence present on a single product nucleic acid primer will vary and may include but are not limited to e.g., a poly(dA) sequence, a poly(dC) sequence, a poly(dG) sequence, a poly(dT) sequence, and the like.

Tail sequences present on template nucleic acids may be naturally occurring (e.g., in the case of the poly(A) tail of an mRNA template) or may be artificially or synthetically produced. For example, in some instances, a tail sequence may be added to a nucleic acid template, e.g., a DNA template, in a tailing reaction. Tailing reactions will vary and may include, e.g., where the tail sequence is added to the template through an enzymatic process. Useful enzymes for tailing a subject nucleic acid template include but are not limited to e.g., terminal transferase (e.g., Terminal Deoxynucleotidyl Transferase, RNA-specific nucleotidyl transferases, and the like). The nucleotide specie of the tailing sequence may be controlled as desired, e.g., by making available in a tailing reaction utilizing a terminal transferase only the desired species of dNTP (e.g., only dATP, only dCTP, only dGTP or only dTTP). In some instances, a "dNTP tailing mix" is used in a tailing reaction where such a mix contains only one species of dNTP. In some instances, a nucleic acid template may be prepared for a tailing reaction e.g., by removal of a 3' phosphate (dephosphorylation) present on the nucleic acid template. Any convenient and appropriate phosphatase may be employed for such purposes including but not limited to e.g., Alkaline Phosphatase (e.g., Shrimp Alkaline Phosphatase and derivative thereof), and the like.

In some instances, the subject methods may include performing a tailing reaction to add a tailing sequence to a template nucleic acid, e.g., by contacting a template nucleic acid with a terminal transferase in the presence of a species of dNTP under conditions sufficient to produce the template having the tail sequence (i.e., a tailed template). The rate of addition of dNTPs—and thus the length of tail sequence—is a function of the ratio of 3' ends to the dNTP concentration, and also which dNTP is used. The terminal transferase reaction is carried out at a temperature at which the terminal transferase is active, such as between 30° C. and 50° C., including 37° C. The dNTPs in the terminal transferase reaction may be present at a final concentration of from 0.01 mM to 1 mM, such as from 0.05 mM to 0.5 mm, including 0.1 mM. The template nucleic acid may be present in the terminal transferase reaction at a concentration of from 0.05 to 500 pmol, such as from 0.5 to 50 pmol, including 1 to 25 pmol, e.g., 5 pmol. A terminal transferase buffer solution and any other useful components (e.g., a metal cofactor such as Co, or the like) may also be included in the terminal transferase reaction, e.g., as a separate solution (e.g., buffer) or as part of a "dNTP tailing mix". The terminal transferase reaction results in the addition of nucleotides at the 3' end of the nucleic acid template and the resulting tailed-template nucleic acid may then be utilized in further steps of the reaction according to the subject methods.

In some embodiments of the subject methods, during amplification of the dsDNA no other primers (which term will also refer to oligonucleotides used to prime an extension reaction) besides the template switch oligonucleotide and the single product nucleic acid primer may be present. Put another way, amplification may proceed using only the template switch oligonucleotide and the single product nucleic acid primer. Accordingly, the present methods of amplifying may be performed in the absence of any additional amplification primers (i.e., no primers are used for amplification besides the template switch oligonucleotide and the single product nucleic acid primer). Accordingly, the subject reaction mixtures utilized in the herein described methods may exclude the presence of any amplification primers in addition to the template switch oligonucleotide and the single product nucleic acid primer (i.e., additional amplification primers may not be added to or otherwise used in amplifying the dsDNA according to embodiments of the present methods).

By "amplification primers", is generally meant primers utilized in an amplification (e.g., PCR amplification), including e.g., those primers typically added (e.g., before the reaction is begun or during the reaction) to an RT-PCR reaction to amplify following first strand synthesis. Conventionally, amplification primers are present in an RT-PCR reaction in addition to first strand synthesis primer(s) and the amplification primers are used separately from the first strand synthesis primer(s) to PCR amplify the generated first strand cDNA. Amplification primers may sometimes be referred to as "second strand synthesis primer(s)", "second strand primer(s)", "PCR primers", "a forward primer", "a reverse primer", "a universal amplification primer", etc., and may sometimes be described as present in a "multiplex primer mix". Even when present during first strand synthesis and/or template switching reactions (e.g., when added at the start of an RT-PCR reaction) amplification primer will generally not be involved in single product nucleic acid synthesis and/or template switching.

Accordingly, in embodiments of the instant methods, amplifying is performed in the absence of one or more amplification primers. In some embodiments, one or more amplification primers are not present (i.e., are absent) from the reaction mixture such that the reaction mixture does not contain amplification primers. In other words, in some embodiments, the reaction mixture may not contain any primers that are not also involved in single product nucleic acid synthesis and/or template switching.

The subject methods may include combining a reverse transcriptase, a single product nucleic acid primer, a template switch oligonucleotide and an amplification polymerase with a template nucleic acid into a reaction mixture. The reaction mixture may contain other components used in reverse transcription and/or PCR, including essential and nonessential components including but not limited to e.g., deoxyribonucleotide triphosphates (dNTPs), buffer, etc.

As noted above, the subject methods include combining a template switch oligonucleotide into the reaction mixture and amplifying using the template switch oligonucleotide. By "template switch oligonucleotide" is meant an oligonucleotide template to which a polymerase switches from an initial template (e.g., template nucleic acid (e.g., a RNA template or a DNA template)) during a nucleic acid polymerization reaction. In this regard, the template may be referred to as a "donor template" and the template switch oligonucleotide may be referred to as an "acceptor template." As used herein, an "oligonucleotide" is a single-stranded multimer of nucleotides from 2 to 500 nucleotides, e.g., 2 to 200 nucleotides. Oligonucleotides may be synthetic or may be made enzymatically, and, in some embodiments, are 10 to 50 nucleotides in length. Oligonucleotides may contain ribonucleotide monomers (i.e., may be oligoribonucleotides or "RNA oligonucleotides") or deoxyribonucleotide monomers (i.e., may be oligodeoxyribonucleotides or "DNA oligonucleotides"). Oligonucleotides may be 10 to 20, 21 to 30, 31 to 40, 41 to 50, 51 to 60, 61 to 70, 71 to 80, 80 to 100, 100 to 150 or 150 to 200, up to 500 or more nucleotides in length, for example.

Reaction mixtures of the subject methods may include the template switch oligonucleotide at a concentration sufficient to readily permit template switching of the polymerase from the template to the template switch oligonucleotide, at a concentration sufficient to amplify the single product nucleic acid using the template switch oligonucleotide or at a concentration sufficient to readily permit template switching and to amplify the single product nucleic acid. For example, the template switch oligonucleotide may be added to the reaction mixture at a final concentration of from 0.01 to 100 µM, such as from 0.1 to 10 µM, such as from 0.5 to 5 µM, including 1 to 2 µM (e.g., 1.2 µM).

The template switch oligonucleotide may include one or more nucleotides (or analogs thereof) that are modified or otherwise non-naturally occurring. For example, the template switch oligonucleotide may include one or more nucleotide analogs (e.g., LNA, FANA, 2'-O-Me RNA, 2'-fluoro RNA, or the like), linkage modifications (e.g., phosphorothioates, 3'-3' and 5'-5' reversed linkages), 5' and/or 3' end modifications (e.g., 5' and/or 3' amino, biotin, DIG, phosphate, thiol, dyes, quenchers, etc.), one or more fluorescently labeled nucleotides, or any other feature that provides a desired functionality to the template switch oligonucleotide.

In certain aspects, the template switch oligonucleotide includes a 3' hybridization domain. The 3' hybridization domain may vary in length, and in some instances ranges from 2 to 10 nts in length, such as 3 to 7 nts in length. The 3' hybridization domain of a template switch oligonucleotide may include a sequence complementary to a non-templated sequence added to a single product nucleic acid. Non-templated sequences, described in more detail below, generally refer to those sequences that do not correspond to and are not templated by a template, e.g., a RNA template or a DNA template. Where present in the 3' hybridization domain of a template switch oligonucleotide, non-templated sequences may encompass the entire 3' hybridization domain or a portion thereof. In some instances, a non-templated sequence may include or consist of a hetero-polynucleotide, where such a hetero-polynucleotide may vary in length from 2 to 10 nts in length, such as 3 to 7 nts in length, including 3 nts. In some instances, a non-templated sequence may include or consist of a homo-polynucleotide, where such a homo-polynucleotide may vary in length from 2 to 10 nts in length, such as 3 to 7 nts in length, including 3 nts.

According to some embodiments, the polymerase (e.g., a reverse transcriptase such as MMLV RT) combined into the reaction mixture has terminal transferase activity such that a homonucleotide stretch (e.g., a homo-trinucleotide, such as C—C—C) may be added to the 3' end of a nascent strand, and the 3' hybridization domain of the template switch oligonucleotide includes a homonucleotide stretch (e.g., a homo-trinucleotide, such as G-G-G) complementary to that of the 3' end of the nascent strand. In other aspects, when the polymerase having terminal transferase activity adds a nucleotide stretch to the 3' end of the nascent strand (e.g., a trinucleotide stretch), the 3' hybridization domain of the template switch oligonucleotide includes a hetero-trinucleotide comprises a nucleotide comprising cytosine and a nucleotide comprising guanine (e.g., an r(C/G)$_3$ oligonucleotide), which hetero-trinucleotide stretch of the template switch oligonucleotide is complementary to the 3' end of the nascent strand. Examples of 3' hybridization domains and template switch oligonucleotides are further described in U.S. Pat. No. 5,962,272, the disclosure of which is herein incorporated by reference.

According to some embodiments, the template switch oligonucleotide includes a modification that prevents the polymerase from switching from the template switch oligonucleotide to a different template nucleic acid after synthesizing the compliment of the 5' end of the template switch oligonucleotide (e.g., a 5' adapter sequence of the template switch oligonucleotide). Useful modifications include, but are not limited to, an abasic lesion (e.g., a tetrahydrofuran derivative), a nucleotide adduct, an iso-nucleotide base (e.g., isocytosine, isoguanine, and/or the like), and any combination thereof.

In some instances, a template switch oligonucleotide may include a 5' adapter sequence (e.g., a defined nucleotide sequence 5' of the 3' hybridization domain of the template switch oligonucleotide), the 5' adapter sequence may serve various purposes in downstream applications. In some instances, the 5' adapter sequence may serve as a primer binding site for further amplification or, e.g., nested amplification or suppression amplification, of the amplified dsDNA.

As summarized above, the present methods include the use of a first strand primer, e.g., a single product nucleic acid primer, in an amplification reaction of the single product nucleic acid to generate an amplified dsDNA. In some instances, the reaction utilized to produce the product double stranded nucleic acid may be a first strand cDNA synthesis reaction utilizing template switching and the first strand primer. A single product nucleic acid primer utilized in amplifying from a single product nucleic acid may be the same primer utilized in generating the single product nucleic acid, e.g., from a RNA template or a DNA template.

A single product nucleic acid primer, also referred to as a single product nucleic acid synthesis primer (e.g., a first strand cDNA synthesis primer) or a first strand primer, includes a template binding domain. For example, the nucleic acid may include a first (e.g., 3') domain that is configured to hybridize to a template nucleic acid, e.g., mRNA, a ssDNA, etc., and may or may not include one or more additional domains which may be viewed as a second (e.g., 5') domain that does not hybridize to the template nucleic acid, e.g., a non-template sequence domain as described in more detail below. The sequence of the template binding domain may be independently defined or arbitrary. In certain aspects, the template binding domain has a defined sequence, e.g., poly dT or gene specific sequence. In other aspects, the template binding domain has an arbitrary sequence (e.g., a random sequence, such as a random hexamer sequence). While the length of the template binding domain may vary, in some instances the length of this domain ranges from 5 to 50 nts, such as 6 to 25 nts, e.g., 6 to 20 nts.

The single product nucleic acid primer may include one or more nucleotides (or analogs thereof) that are modified or otherwise non-naturally occurring. For example, the single product nucleic acid primer may include one or more nucleotide analogs (e.g., LNA, FANA, 2'-O-Me RNA, 2'-fluoro RNA, or the like), linkage modifications (e.g., phosphorothioates, 3'-3' and 5'-5' reversed linkages), 5' and/or 3' end modifications (e.g., 5' and/or 3' amino, biotin, DIG, phosphate, thiol, dyes, quenchers, etc.), one or more fluorescently labeled nucleotides, or any other feature that provides a desired functionality to the single product nucleic acid primer.

In some instances, a single product nucleic acid primer may include a 5' adapter sequence (e.g., a defined nucleotide sequence 5' of the 3' hybridization domain of the single product nucleic acid primer), the 5' adapter sequence may serve various purposes in downstream applications. In some instances, the 5' adapter sequence may serve as a primer binding site for further amplification or, e.g., nested amplification or suppression amplification, of the amplified dsDNA.

In some instances, one or more of the primers (including e.g., single product nucleic acid primers, template switch oligonucleotides, etc.) utilized in the subject methods may include two or more domains. For example, the primer may include a first (e.g., 3') domain that hybridizes to a template and a second (e.g., 5') domain that does not hybridize to a template. The sequence of the first and second domains may be independently defined or arbitrary. In certain aspects, the first domain has a defined sequence and the sequence of the second domain is defined or arbitrary. In other aspects, the first domain has an arbitrary sequence (e.g., a random sequence, such as a random hexamer sequence) and the sequence of the second domain is defined or arbitrary. In some instances, the sequences of both domains are defined. Where a primer (including e.g., single product nucleic acid primers, template switch oligonucleotides, etc.) utilized in the subject methods includes two or more domains, one or more of the domains may include a non-templated sequence as described below.

The methods of the present disclosure include combining one or more polymerases into the reaction mixture, including e.g., an amplification polymerase, a reverse transcriptase, an amplification polymerase and a reverse transcriptase, etc. A variety of polymerases may be employed when practicing the subject methods.

In some instances, a polymerase combined into the reaction mixture is capable of template switching, where the polymerase uses a first nucleic acid strand as a template for polymerization, and then switches to the 3' end of a second template nucleic acid strand to continue the same polymerization reaction. In some instances, the polymerase capable of template switching is a reverse transcriptase. Reverse transcriptases capable of template-switching that find use in practicing the subject methods include, but are not limited to, retroviral reverse transcriptase, retrotransposon reverse transcriptase, retroplasmid reverse transcriptases, retron reverse transcriptases, bacterial reverse transcriptases, group II intron-derived reverse transcriptase, and mutants, variants derivatives, or functional fragments thereof, e.g., RNase H minus or RNase H reduced enzymes. For example, the reverse transcriptase may be a Moloney Murine Leukemia Virus reverse transcriptase (MMLV RT) or a *Bombyx mori* reverse transcriptase (e.g., *Bombyx mori* R2 non-LTR element reverse transcriptase). Polymerases capable of template switching that find use in practicing the subject methods are commercially available and include SMARTScribe™ reverse transcriptase and PrimeScript™ reverse transcriptase available from Clontech Laboratories, Inc. (Mountain View, Calif.).

In addition to a template switching capability, the polymerase may include other useful functionalities. For example, the polymerase may have terminal transferase activity, where the polymerase is capable of catalyzing the addition of deoxyribonucleotides to the 3' hydroxyl terminus of a RNA or DNA molecule. In certain aspects, when the polymerase reaches the 5' end of the template, the polymerase is capable of incorporating one or more additional nucleotides at the 3' end of the nascent strand not encoded by the template. For example, when the polymerase has terminal transferase activity, the polymerase may be capable of incorporating 1, 2, 3, 4, 5, 6, 7, 8, 9, 10 or more additional nucleotides at the 3' end of the nascent strand. All of the nucleotides may be the same (e.g., creating a homonucleotide stretch at the 3' end of the nascent strand) or one or more of the nucleotides may be different from the other(s) (e.g., creating a heteronucleotide stretch at the 3' end of the nascent strand). In certain aspects, the terminal transferase activity of the polymerase results in the addition of a homonucleotide stretch of 2, 3, 4, 5, 6, 7, 8, 9, 10 or more of the same nucleotides (e.g., all dCTP, all dGTP, all dATP, or all dTTP). For example, according to one embodiment, the polymerase is an MMLV reverse transcriptase (MMLV RT). MMLV RT incorporates additional nucleotides (predominantly dCTP, e.g., three dCTPs) at the 3' end of the nascent strand. As described in greater detail elsewhere herein, these additional nucleotides may be useful for enabling hybridization between a 3' hybridization domain of a template switch oligonucleotide and the 3' end of the nascent strand, e.g., to facilitate template switching by the polymerase from the template to the template switch oligonucleotide.

Reverse transcriptase utilized in the subject methods may, in some instances, be a thermo-sensitive polymerase, i.e., a polymerase that is not thermostable. Such thermo-sensitive polymerases may become inactive at a temperature above their active temperature range. For example, in some instances, a thermos-sensitive polymerase may become inactive or demonstrate significantly reduced activity after being exposed to temperatures of 75° or higher, 80° or higher, 85° or higher, 90° or higher or 95° or higher.

Where a reverse transcriptase is employed, it may be combined into the reaction mixture such that the final concentration of the reverse transcriptase is sufficient to produce a desired amount of the RT reaction product, e.g., a desired amount of a single product nucleic acid. In certain aspects, the reverse transcriptase (e.g., an MMLV RT, a *Bombyx mori* RT, etc.) is present in the reaction mixture at a final concentration of from 0.1 to 200 units/µL (U/µL), such as from 0.5 to 100 U/µL, such as from 1 to 50 U/µL, including from 5 to 25 U/µL, e.g., 20 U/µL.

The methods of the present disclosure include the use of an amplification polymerase, e.g., for use in amplifying from a single product nucleic acid using a template switch oligonucleotide and a single product nucleic acid primer to generate an amplified dsDNA product. Any convenient amplification polymerase may be employed including but not limited to DNA polymerases including thermostable polymerases. Useful amplification polymerases include e.g., Taq DNA polymerases, Pfu DNA polymerases, derivatives thereof and the like. In some instances, the amplification polymerase may be a hot start polymerase including but not limited to e.g., a hot start Taq DNA polymerase, a hot start Pfu DNA polymerase, and the like.

Hot start polymerases will vary, and may include e.g., a polymerase present in a complex with a polymerase binding agent that directly associates with the polymerase to prevent or inhibit its processivity, i.e., prevent the polymerase from polymerizing nucleic acid. Polymerase binding agents will vary and may include e.g., antibodies, aptamers, and the like, that specifically bind the polymerase preventing its activity. In a "hot start" reaction, heating the reaction may be employed to dissociate the polymerase binding agent(s) from the polymerase, allowing the polymerase to polymerize nucleic acid. Hot start polymerases may also be thermostable.

The amplification polymerase is combined into the reaction mixture such that the final concentration of the amplification polymerase is sufficient to produce a desired amount of the product nucleic acid, e.g., a desired amount of product amplified dsDNA. In certain aspects, the amplification polymerase (e.g., a thermostable DNA polymerase, a hot start DNA polymerase, etc.) is present in the reaction mixture at a final concentration of from 0.1 to 200 units/µL (U/µL), such as from 0.5 to 100 U/µL, such as from 1 to 50 U/µL, including from 5 to 25 U/µL, e.g., 20 U/µL.

As described above, the subject methods may include combining dNTPs into a reaction mixture. In certain aspects, each of the four naturally-occurring dNTPs (dATP, dGTP, dCTP and dTTP) are added to the reaction mixture. For example, dATP, dGTP, dCTP and dTTP may be added to the reaction mixture such that the final concentration of each dNTP is from 0.01 to 100 mM, such as from 0.1 to 10 mM, including 0.5 to 5 mM (e.g., 1 mM). In some instances, one or more types of nucleotide added to the reaction mixture may be a non-naturally occurring nucleotide, e.g., a modified nucleotide having a binding or other moiety (e.g., a fluorescent moiety) attached thereto, a nucleotide analog, or any other type of non-naturally occurring nucleotide that finds use in the subject methods or a downstream application of interest.

Reaction mixtures may be subjected to various temperatures to drive various aspects of the reaction including but not limited to e.g., denaturing/melting of nucleic acids, hybridization/annealing of nucleic acids, polymerase-mediated elongation/extension, etc. Temperatures at which the various processes are performed may be referred to according to the process occurring including e.g., melting temperature, annealing temperature, elongation temperature, etc. The optimal temperatures for such processes will vary, e.g., depending on the polymerase used, depending on characteristics of the nucleic acids, etc. Optimal temperatures for particular polymerases, including reverse transcriptases and amplification polymerases, may be readily obtained from reference texts. Optimal temperatures related to nucleic acids, e.g., annealing and melting temperatures may be readily calculated based on known characteristics of the subject nucleic acid including e.g., overall length, hybridization length, percent G/C content, secondary structure prediction, etc.

Once the amplified dsDNA product is produced, the methods may include inputting the product directly into one or more downstream applications of interest (e.g., cloning, sequencing, etc.). In other aspects, the methods may include using the product as dsDNA inserts, e.g., into a vector, for cloning and/or library construction.

Template Nucleic Acids

Template nucleic acids may be present in a template nucleic acid composition (e.g., a defined composition) or a biological sample (e.g., a sample obtained from or containing a living organism and/or living cells). Biological samples containing template nucleic acids may be prepared, by any convenient means, to render the nucleic acids of the sample available to components of the herein described methods (e.g., primers, oligonucleotides, etc.). Preparing biological samples containing template nucleic acids may include but is not limited to e.g., homogenizing the sample, lysing one or more cell types of the sample, enriching the sample for desired nucleic acids, removing one or more components present in the sample (e.g., proteins, lipids, contaminating nucleic acids), performing nucleic acid isolation to isolate the template nucleic acids, etc.

Template nucleic acids of the subject disclosure may contain a plurality of distinct template nucleic acids of differing sequence. Template nucleic acids (e.g., a template RNA, a template DNA, or the like) may be polymers of any length. While the length of the polymers may vary, in some instances the polymers are 10 nts or longer, 20 nts or longer, 50 nts or longer, 100 nts or longer, 500 nts or longer, 1000 nts or longer, 2000 nts or longer, 3000 nts or longer, 4000 nts or longer, 5000 nts or longer or more nts. In certain aspects, template nucleic acids are polymers, where the number of bases on a polymer may vary, and in some instances is 10 nts or less, 20 nts or less, 50 nts or less, 100 nts or less, 500 nts or less, 1000 nts or less, 2000 nts or less, 3000 nts or less, 4000 nts or less, or 5000 nts or less, 10,000 nts or less, 25,000 nts or less, 50,000 nts or less, 75,000 nts or less, 100,000 nts or less.

According to certain embodiments, the template nucleic acids are template ribonucleic acids (template RNA). Template RNAs may be any type of RNA (or sub-type thereof) including, but not limited to, a messenger RNA (mRNA), a microRNA (miRNA), a small interfering RNA (siRNA), a transacting small interfering RNA (ta-siRNA), a natural small interfering RNA (nat-siRNA), a ribosomal RNA (rRNA), a transfer RNA (tRNA), a small nucleolar RNA (snoRNA), a small nuclear RNA (snRNA), a long non-coding RNA (lncRNA), a non-coding RNA (ncRNA), a transfer-messenger RNA (tmRNA), a precursor messenger RNA (pre-mRNA), a small Cajal body-specific RNA (scaRNA), a piwi-interacting RNA (piRNA), an endoribonuclease-prepared siRNA (esiRNA), a small temporal RNA (stRNA), a signal recognition RNA, a telomere RNA, a ribozyme, or any combination of RNA types thereof or subtypes thereof.

According to certain embodiments, the template nucleic acids are template deoxyribonucleic acids (template DNA). Template DNAs may be any type of DNA (or sub-type thereof) including, but not limited to, genomic DNA (e.g., prokaryotic genomic DNA (e.g., bacterial genomic DNA, archaea genomic DNA, etc.), eukaryotic genomic DNA (e.g., plant genomic DNA, fungi genomic DNA, animal genomic DNA (e.g., mammalian genomic DNA (e.g., human genomic DNA, rodent genomic DNA (e.g., mouse, rat, etc.), etc.), insect genomic DNA (e.g., *drosophila*), amphibian genomic DNA (e.g., *Xenopus*), etc.)), viral genomic DNA, mitochondrial DNA, or any combination of DNA types thereof or subtypes thereof.

The number of distinct template nucleic acids of differing sequence in a given template nucleic acid composition may vary. While the number of distinct template nucleic acids in a given template nucleic acid composition may vary, in some instances the number of distinct template nucleic acids in a given template nucleic acid composition ranges from 1 to $10^8$, such as 1 to $10^7$, including 1 to $10^5$.

The template nucleic acid composition employed in such methods may be any suitable nucleic acid sample. The nucleic acid sample that includes the template nucleic acid may be combined into the reaction mixture in an amount sufficient for producing the product nucleic acid. According to one embodiment, the nucleic acid sample is combined into the reaction mixture such that the final concentration of nucleic acid in the reaction mixture is from 1 fg/μL to 10 μg/μL, such as from 1 μg/μL to 5 μg/μL, such as from 0.001 μg/μL to 2.5 μg/μL, such as from 0.005 μg/μL to 1 μg/μL, such as from 0.01 μg/μL to 0.5 μg/μL, including from 0.1 μg/μL to 0.25 μg/μL. In certain aspects, the nucleic acid sample that includes the template nucleic acid is isolated from a single cell, e.g., as described in greater detail below. In other aspects, the nucleic acid sample that includes the template nucleic acid is isolated from 2, 3, 4, 5, 6, 7, 8, 9, 10 or more, 20 or more, 50 or more, 100 or more, or 500 or more cells. According to certain embodiments, the nucleic acid sample that includes the template nucleic acid is isolated from 500 or less, 100 or less, 50 or less, 20 or less, 10 or less, 9, 8, 7, 6, 5, 4, 3, or 2 cells.

The template nucleic acid may be present in any nucleic acid sample of interest, including but not limited to, a nucleic acid sample isolated from a single cell, a plurality of cells (e.g., cultured cells), a tissue, an organ, or an organism (e.g., bacteria, yeast, or the like). In certain aspects, the nucleic acid sample is isolated from a cell(s), tissue, organ, and/or the like of a mammal (e.g., a human, a rodent (e.g., a mouse), or any other mammal of interest). In other aspects, the nucleic acid sample is isolated from a source other than a mammal, such as bacteria, yeast, insects (e.g., *drosophila*), amphibians (e.g., frogs (e.g., *Xenopus*)), viruses, plants, or any other non-mammalian nucleic acid sample source.

Approaches, reagents and kits for isolating nucleic acids from such sources are known in the art. For example, kits for isolating nucleic acids from a source of interest—such as the NucleoSpin®, NucleoMag® and NucleoBond® genomic DNA or RNA isolation kits by Clontech Laboratories, Inc. (Mountain View, Calif.)—are commercially available. In certain aspects, the nucleic acid is isolated from a fixed biological sample, e.g., formalin-fixed, paraffin-embedded (FFPE) tissue. Nucleic acids from FFPE tissue may be isolated using commercially available kits—such as the NucleoSpin® FFPE DNA or RNA isolation kits by Clontech Laboratories, Inc. (Mountain View, Calif.).

Non-Templated Sequences and Non-Template Sequences

The terms "non-templated sequence" and "non-template sequence" generally refer to those sequences involved in the subject method that do not correspond to the template (e.g., are not present in the templates, do not have a complementary sequence in the template or are unlikely to be present in or have a complementary sequence in the template). Non-templated sequences are those that are not templated by a template, e.g., a RNA or DNA template, thus they may be added during an elongation reaction in the absence of corresponding template, e.g., nucleotides added by a polymerase having non-template directed terminal transferase activity. Non-template and non-templated sequence may, but not exclusively, refer to those sequences present on a primer or template switch oligonucleotide that do not hybridize to the template (such sequences may, in some instances, be referred to as non-hybridizing sequence. Non-templated sequence will vary, in both size and composition. In some instances, non-templated sequence, e.g., non-templated sequence present on a template switch oligonucleotide or a single product nucleic acid primer, may range from 10 nt to 1000 nt or more including but not limited to e.g., 10 nt to 900 nt, 10 nt to 800 nt, 10 nt to 700 nt, 10 nt to 600 nt, 10 nt to 500 nt, 10 nt to 400 nt, 10 nt to 300 nt, 10 nt to 200 nt, 10 nt to 100 nt, 10 nt to 90 nt, 10 nt to 80 nt, 10 nt to 70 nt, 10 nt to 60 nt, 10 nt to 50 nt, 10 nt to 40 nt, 10 nt to 30 nt, 10 nt to 20 nt, etc.

In some instances, a non-templated sequence, as noted above, may be included in the 3' hybridization domain of a template switch oligonucleotide. When present in the 3' hybridization domain of a template switch oligonucleotide, a non-templated sequence may include or consist of a hetero-polynucleotide, where such a hetero-polynucleotide may vary in length from 2 to 10 nts in length, such as 3 to 7 nts in length, including 3 nts. In some instances, a non-templated sequence present in the 3' hybridization domain of a template switch oligonucleotide may include or consist of a homo-polynucleotide, where such a homo-polynucleotide may vary in length from 2 to 10 nts in length, such as 3 to 7 nts in length, including 3 nts.

Non-templated sequences present on a template switch oligonucleotide or a primer, e.g., a single product nucleic acid primer, may be present at the 5' end of the template switch oligonucleotide or primer and may, in such instances, be referred to as a 5' non-templated sequence. In the subject methods of amplification, in some instances, only one of the template switch oligonucleotide or single product nucleic acid primer may include a non-templated sequence (e.g., a 5' non-templated sequence). In the subject methods of amplification, in some instances, both the template switch oligonucleotide and the single product nucleic acid primer include a non-templated sequence (e.g., a 5' non-templated sequence). Where both the template switch oligonucleotide and the single product nucleic acid primer include a non-templated sequence, the non-templated sequences may be the same or different. In some instances, both the template switch oligonucleotide and the single product nucleic acid primer may have the same 5' non-templated sequence.

In some instances, non-templated sequence, including e.g., 5' non-templated sequence, may include one or more restriction endonuclease recognition sites. In some instances, following amplification, the one or more restriction endonuclease recognition sites may be incorporated into the amplified dsDNA allowing manipulation of the amplified dsDNA, e.g., cleaving the amplified dsDNA at the one or more incorporated restriction endonuclease recognition sites.

In some instances, non-templated sequence, including e.g., 5' non-templated sequence, may include one or more primer binding sites. In some instances, following amplification, the one or more primer binding sites may be incorporated into the amplified dsDNA allowing further amplification of the amplified dsDNA, including e.g., amplifying a portion of the amplified dsDNA using the one or more primer binding sites including e.g., through nested PCR of the amplified dsDNA using the one or more primer binding sites.

Useful primer binding sites will vary widely depending on the desired complexity of the primer binding site and the corresponding primer. In some instances, useful primer binding sites include those having complementarity to a II A primer (e.g., as available from Takara Bio USA, Inc., Mountain View, Calif.). According to one embodiment, the template switch oligonucleotide includes a non-template sequence that includes a II A primer binding site. According to one embodiment, the single product nucleic acid primer includes a non-template sequence that includes a II A primer binding site. According to one embodiment, both the template switch oligonucleotide and the single product nucleic acid primer include a non-template sequence that includes a II A primer binding site.

In some instances, non-templated sequence, including e.g., 5' non-templated sequence, may include one or more barcode sequences, In some instances, such barcode sequences may be or may include a unique molecular identifier (UMI) domain and/or a barcoded unique molecular identifier (BUMI) domain, described in detail below. In some instances, one or more barcode sequences of a non-templated sequence may provide for retrospective identification of the source of an amplified dsDNA, e.g., following a sequencing reaction where the barcode is sequenced. For example, in some instances, a non-templated sequence that includes a barcode specific for the source (e.g., sample, well, cell, etc.) of the template is incorporated during the amplifying. Such source identifying barcodes may be referred to herein as a "source barcode sequence" and such sequences may vary and may be assigned a term based on the source that is identified by the barcode. Source barcodes may include e.g., a sample barcode sequence that retrospectively identifies the sample from which the template was derived, a well barcode sequence that retrospectively identifies the well (e.g., of a multi-well plate) from which the template was derived, a droplet barcode sequence that retrospectively identifies the droplet from which the template was derived, a cell barcode sequence that retrospectively identifies the cell (e.g., of a multi-cellular sample) from which the template was derived, etc. Barcodes may find use in various procedures including e.g., where nucleic acids are pooled following barcoding, e.g., prior to sequencing.

In some instances, a non-templated sequence, e.g., present on a template switch oligonucleotide and/or a single product nucleic acid primer, includes a sequencing platform adapter construct. By "sequencing platform adapter construct" is meant a nucleic acid construct that includes at least a portion of a nucleic acid domain (e.g., a sequencing platform adapter nucleic acid sequence) or complement thereof utilized by a sequencing platform of interest, such as a sequencing platform provided by Illumina® (e.g., the HiSeq™, MiSeq™ and/or Genome Analyzer™ sequencing systems); Ion Torrent™ (e.g., the Ion PGM™ and/or Ion Proton™ sequencing systems); Pacific Biosciences (e.g., the PACBIO RS II sequencing system); Life Technologies™ (e.g., a SOLiD sequencing system); Roche (e.g., the 454 GS FLX+ and/or GS Junior sequencing systems); or any other sequencing platform of interest.

In certain aspects, a non-templated sequence includes a sequencing platform adapter construct that includes a nucleic acid domain that is a domain (e.g., a "capture site" or "capture sequence") that specifically binds to a surface-attached sequencing platform oligonucleotide (e.g., the P5 or P7 oligonucleotides attached to the surface of a flow cell in an Illumina® sequencing system); a sequencing primer binding domain (e.g., a domain to which the Read 1 or Read 2 primers of the Illumina® platform may bind). The sequencing platform adapter constructs may include nucleic acid domains (e.g., "sequencing adapters") of any length and sequence suitable for the sequencing platform of interest. In certain aspects, the nucleic acid domains are from 4 to 200 nts in length. For example, the nucleic acid domains may be from 4 to 100 nts in length, such as from 6 to 75, from 8 to 50, or from 10 to 40 nts in length. According to certain embodiments, the sequencing platform adapter construct includes a nucleic acid domain that is from 2 to 8 nts in length, such as from 9 to 15, from 16-22, from 23-29, or from 30-36 nts in length.

The nucleic acid domains may have a length and sequence that enables a polynucleotide (e.g., an oligonucleotide) employed by the sequencing platform of interest to specifically bind to the nucleic acid domain, e.g., for solid phase amplification and/or sequencing by synthesis of the cDNA insert flanked by the nucleic acid domains. Example nucleic acid domains include the P5 (5'-AATGATACGGCGAC-CACCGA-3') (SEQ ID NO:1), P7 (5'-CAAGCAGAA-GACGGCATACGAGAT-3') (SEQ ID NO:2), Read 1 primer (5'-ACACTCTTTCCCTACACGACGCTCTTCCGATCT-3') (SEQ ID NO:3) and Read 2 primer (5'-GTGACTG-GAGTTCAGACGTGTGCTCTTCCGATCT-3') (SEQ ID NO:4) domains employed on the Illumina®-based sequencing platforms. Other example nucleic acid domains include the A adapter (5'-CCATCTCATCCCTGCGTGT-CTCCGACTCAG-3') (SEQ ID NO:5) and P1 adapter (5'-CCTCTCTATGGGCAGTCGGTGAT-3') (SEQ ID NO:6) domains employed on the Ion Torrent™-based sequencing platforms.

The nucleotide sequences of non-templated sequence domains useful for sequencing on a sequencing platform of interest may vary and/or change over time. Adapter sequences are typically provided by the manufacturer of the sequencing platform (e.g., in technical documents provided with the sequencing system and/or available on the manufacturer's website). Based on such information, the sequence of the sequencing platform adapter construct of the non-templated sequence (e.g., a template switch oligonucleotide and/or a single product nucleic acid primer, and/or the like) may be designed to include all or a portion of one or more nucleic acid domains in a configuration that enables sequencing the nucleic acid insert (corresponding to the template nucleic acid) on the platform of interest. Sequencing platform adaptor constructs that may be included in a non-templated sequence as well as other nucleic acid reagents described herein, are further described in U.S. patent application Ser. No. 14/478,978 published as US 2015-0111789 A1, the disclosure of which is herein incorporated by reference.

Non-templated sequence may be added, e.g., to a template switch oligonucleotide, a single product nucleic acid primer, an amplified product dsDNA, etc., by a variety of means. For example, as noted above, non-templated sequence may be added through the action of a polymerase with terminal transferase activity. Non-templated sequence, e.g., present on a primer or oligonucleotide, may be incorporated into a product nucleic acid during an amplification reaction. In some instances, non-templated nucleic acid sequence may be directly attached to a nucleic acid, e.g., to a primer or oligonucleotide prior to amplification, to a product nucleic acid following amplification, etc. Methods of directly attaching a non-templated sequence to a target nucleic acid will vary and may include but are not limited to e.g., ligation, chemical synthesis/linking, enzymatic nucleotide addition (e.g., by a polymerase with terminal transferase activity), and the like.

In some instances, the methods may include attaching sequencing platform adapter constructs to ends of a product nucleic acid or a derivative thereof (such as amplified dsDNA as described above), e.g., in those embodiments where the single product nucleic acid primer and template switch oligonucleotides do not include such adaptor constructs. The adapter constructs attached to the ends of the product nucleic acid or a derivative thereof may include any sequence elements useful in a downstream sequencing application, including any of the elements described above with respect to the optional sequencing platform adapter constructs of the template switch oligonucleotide and/or single product nucleic acid synthesis primer. For example, the adapter constructs attached to the ends of the product nucleic acid or a derivative thereof may include a nucleic acid domain or complement thereof selected from the group consisting of: a domain that specifically binds to a surface-attached sequencing platform oligonucleotide, a sequencing primer binding domain, a barcode domain, a barcode sequencing primer binding domain, a molecular identification domain, and combinations thereof.

According to certain embodiments, the sequencing platform adapter constructs attached to ends of the product nucleic acid or a derivative thereof are present on a single nucleic acid molecule. In certain aspects, when the sequencing platform adapter constructs are present on a single molecule, attaching the constructs to the product nucleic acid or a derivative thereof produces a circular nucleic acid that includes the product nucleic acid or a derivative thereof and the sequencing platform adapter constructs. Such embodiments find use in a variety of applications, e.g., where it is desirable to join multiple nucleic acid sequence elements on a single nucleic acid. As just one example, when it is desirable to clone the product nucleic acid or a derivative thereof into a vector (e.g., a cloning vector, an expression vector, a viral vector, or any other vector type of interest). As such, when the sequencing platform adapter constructs attached to ends of the product nucleic acid or a derivative thereof are present on a single nucleic acid molecule, the single nucleic acid molecule may further include vector elements of interest, including but not limited to, a selectable marker (e.g., a genetic element that confers on a host organism resistance to a selection agent); a reporter gene (e.g., a gene that encodes a fluorescent protein (e.g., GFP, RFP, or the like), beta-galactosidase, beta-glucuronidase, chloramphenicol acetyltransferase (CAT), or any other useful reporter gene); a promoter (e.g., a T7, T3, or other promoter); an origin of replication (e.g., oriC); a multiple cloning site, or any combination of such elements.

As summarized above, embodiments of the subject methods include attaching sequencing platform adapter constructs to the ends of the product nucleic acid or a derivative thereof. By "derivative" of the product nucleic acid is meant a modified form of the product nucleic acid and/or a nucleic acid generated from the product nucleic acid. One example of a modified form of the product nucleic acid is a single or double stranded nucleic acid produced by treating the product nucleic acid with an enzyme (e.g., such as a nuclease (e.g., a restriction endonuclease, exonuclease, RNase, or the like), uracil-N-glycosylase (UDG), a uracil-specific excision reagent, and/or the like), a chemical that modifies one or more nucleotides of the product nucleic acid, or any other agent that makes a desired modification to one or more nucleotides of the product nucleic acid.

In certain aspects, one or both ends of the amplified nucleic acids, e.g., amplified dsDNA, or derivatives thereof include a recognition site for a restriction enzyme, and modifying the ends of the double-stranded product nucleic acid derivative includes contacting a restriction enzyme with its recognition site, such that the restriction enzyme cleaves (or "digests") the end. The cleaved end may be a blunt end or a "sticky" end, and attaching the sequencing platform adapter construct may include ligating the construct to the blunt or sticky end. According to certain embodiments, one or more restriction enzyme recognition sites are engineered into the product nucleic acid (e.g., by selection and inclusion of such a recognition site in the template switch oligonucleotide, a first-strand synthesis primer, or both) to facilitate attachment (e.g., ligation) of the sequencing platform adapter constructs to the treated ends of the product nucleic acid or a double-stranded derivative thereof.

Attachment of the sequencing platform adapter constructs may be achieved using any suitable approach. In certain aspects the adapter constructs are attached to the ends of the product nucleic acid or a derivative thereof using an approach that is the same or similar to "seamless" cloning strategies. Seamless strategies eliminate one or more rounds of restriction enzyme analysis and digestion, DNA end-repair, dephosphorylation, ligation, enzyme inactivation and clean-up, and the corresponding loss of nucleic acid material. Seamless attachment strategies of interest include: the In-Fusion® cloning systems available from Takara Bio USA, Inc. (Mountain View, Calif.), SLIC (sequence and ligase independent cloning) as described in Li & Elledge (2007) *Nature Methods* 4:251-256; Gibson assembly as described in Gibson et al. (2009) *Nature Methods* 6:343-345; CPEC (circular polymerase extension cloning) as described in Quan & Tian (2009) *PLoS ONE* 4(7): e6441; SLiCE (seamless ligation cloning extract) as described in Zhang et al. (2012) *Nucleic Acids Research* 40(8): e55, and the GeneArt® seamless cloning technology by Life Technologies (Carlsbad, Calif.). According to certain embodiments, the adapter constructs are attached to the ends of the product nucleic acid or a derivative thereof using Gibson assembly, which enables efficient attachment of nucleic acids in a single tube isothermal reaction regardless of fragment length or end compatibility. According to this approach, an exonuclease creates single-stranded 3' overhangs that facilitate the annealing of fragments that share complementarity at one end (overlap region), a polymerase fills in (or "repairs") gaps within each annealed fragment, and a DNA ligase seals nicks in the assembled DNA. The result is a double-stranded fully sealed DNA molecule that can serve as input material for a downstream application of interest, e.g., sequencing using a sequencing platform of interest (with or without amplification prior to sequencing).

Any suitable approach may be employed for providing additional nucleic acid sequencing domains to a product nucleic acid or derivative thereof having less than all of the useful or necessary sequencing domains for a sequencing platform of interest. For example, the product nucleic acid or derivative thereof could be amplified using PCR primers having adapter sequences at their 5' ends (e.g., 5' of the region of the primers complementary to the product nucleic acid or derivative thereof), such that the amplicons include the adapter sequences in the original product nucleic acid as well as the adapter sequences in the primers, in any desired configuration. Other approaches, including those based on seamless cloning strategies, restriction digestion/ligation, or the like may be employed.

BUMI Domains

As noted above, in some instances, method of the instant disclosure may employ non-templated nucleic acid sequences that include a barcoded unique molecular identifier (BUMI) domain. For example, non-templated sequences, including non-templated sequences attached to a primer or a template switch oligonucleotide, may include a BUMI domain. In some instances, one or nucleic acids that include a BUMI domain may be ligated or otherwise attached to a nucleic acid described herein, including but not limited to e.g., a template nucleic acid, a single product nucleic acid, an amplified dsDNA product, and the like.

A BUMI domain is a region or subsequence of a nucleic acid that includes a BUMI tag or portion thereof. A BUMI tag is made up of a series of interspersed barcode and unique molecular identifier (UMI) bases. By interspersed is meant that the bases which are barcode bases (i.e., the bases that collectively make up the barcode component of a BUMI tag) are distributed or positioned among UMI bases (i.e., the bases that collectively make up the UMI domain of a BUMI tag). As such, a given BUMI tag or portion thereof that is present in a BUMI domain is one that includes at least one UMI base positioned adjacent to at least one barcode base, where in those instances in which the BUMI tag is made up of 3 or more bases, at least two bases of a first type (e.g., UMI or barcode) may be separated by at least one base of another type (e.g., UMI or barcode). The length of a given BUMI tag may vary, ranging in some instances from 2 to 200 nts, such as 3 to 100 nts, including 4 to 50 nts, where in some instances the length ranges from 5 to 25 nts, e.g., 6 to 20 nts, where specific lengths of interest include, but are not limited to: 6, 7, 8, 9, 10, 11, 12, 13, 14, 15, and 16 nts.

In a given BUMI tag, the number of barcode bases may vary, ranging in some instances from 1 to 20, such as 1 to 10, e.g., 1 to 6. The number of contiguous barcode bases in a given BUMI tag may also vary, ranging in some instances from 1 to 10, such as 1 to 5, e.g., 1 to 3. In a given BUMI tag, the number of UMI bases may also vary, ranging in some instances from 1 to 20, such as 1 to 12, including 1 to 10, e.g., 1 to 6. The number of contiguous UMI bases in a given BUMI tag may also vary, ranging in some instances from 1 to 10, such as 1 to 5, e.g., 1 to 3. In addition, the pattern and ratio of barcode and UMI bases can be varied. In some instances, contiguous placement of barcode bases is avoided so as to reduce the probability of a BUMI tag having a spurious homology to a primer. Other examples of the pattern of barcode and UMI bases include: (a) one barcode base followed by two UMI bases, with this pattern repeated throughout the length of the BUMI tag; (b) one barcode base followed by one UMI base, then by one barcode base and two UMI bases, and this unit of five bases repeated for a total of two or more five-base units, followed by a barcode base and then a UMI base at the end of the BUMI tag; etc. A large number of such variations in the pattern of barcode and UMI bases can be constructed. BUMI tags may be made up of naturally occurring or non-naturally occurring bases, as desired. As such, BUMI tags may be made up solely of naturally occurring bases, e.g., adenine, guanine, thymine and cytosine. Alternatively, BUMI tags can also incorporate one or more modified nucleotides and nucleotide analogs that are capable of acting as templates for polymerase enzymes, such as methylated nucleotides, biotinylated nucleotides (for example, biotin-11-dUTP or 5-(bio-AC-AP3)dCTP), nucleotides modified with dyes or haptens, boron-modified nucleotides (2'-deoxynucleoside 5'-alpha-[P-borano]-triphosphates), ferrocene-labeled analogs of dTTP (for example, 5-(3-ferrocenecarboxamidopropenyl-1) 2'-deoxyuridine 5'-triphosphate (Fc1-dUTP)), among others. Accordingly, BUMI tags can incorporate one or more of modified nucleotides and nucleotide analogs (e.g., LNA, FANA, 2'-O-Me RNA, 2'-fluoro RNA, or the like), linkage modifications (e.g., phosphorothioates, 3'-3' and 5'-5' reversed linkages), 5' and/or 3' end modifications (e.g., 5' and/or 3' amino, biotin, DIG, phosphate, thiol, dyes, quenchers, etc.), one or more fluorescently labeled nts, or any other feature that provides a desired functionality. Use of modified nucleotides in BUMI tags can allow PCR products incorporating such tags to be detected by differences in electrophoretic mobility, by fluorescence, by antibody binding, and/or by enzymatic activity, in addition to detection using hybridization and/or sequencing methods.

The sequence of BUMI tags may vary, as desired. In some instances, the first base to be sequenced (e.g., 5' most nucleotide) of a BUMI is a UMI base. This configuration increases complexity of sequencing reads, yielding improved results in some downstream applications. A given BUMI tag can include Hamming distances and can be error-correcting. BUMIs can be configured so that they may be used for error correction in certain downstream applications. BUMIs can be configured for determining SNP confidence (e.g., confidence that an observed SNP is true and not a PCR error that was propagated through amplification). In some instances, a BUMI tag may include an error in one or more barcode bases that can be corrected. Knowing the error rate of the barcode bases in a BUMI tag can be informative of the error rate of the UMI bases in the same BUMI tag because the locations are much closer than in a traditional barcode-UMI orientation.

Figure 7A:
FIG. 7A-7D provide illustrations of various types of BUMI domains.
Figure 7B:
Figure 7C:
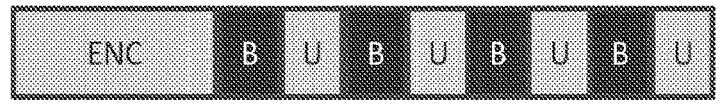
Figure 7D:

FIGS. 7A to 7D provide illustrations of different types of BUMI domains, e.g., that in some instances may be included in the non-templated sequence of a nucleic acid, e.g., a primer or template switch oligonucleotide of the present methods. In FIG. 7A, the illustrated BUMI domain is coincident or fully made up of a BUMI tag, such that the BUMI tag, illustrated as a series of B and U nucleotides, is the same length as the BUMI domain. In FIG. 7B, the BUMI domain includes only a portion of a BUMI tag, as illustrated by the four-nucleotide BUBU sequence. Also shown is one or more additional nucleotide sub-sequences (indicated by the black bar), which may have any desired sequence and may vary in length as desired, where this sub-sequence ranges in some instances from 1 to 10 nts, such as 2 to 8 nts, e.g., 3 to 6 nts, in length. FIG. 7C illustrates a BUMI domain that includes a full BUMI tag, e.g., as shown in FIG. 7A, coupled to a BUMI encoding component (designated ENC), where this component of the BUMI domain is described in greater detail below. FIG. 7D illustrates a BUMI domain that includes an encoding component and a partial BUMI tag.

In some instances, a nucleic acid composition (i.e., a plurality of individual nucleic acid molecules of a particular type, where each of the individual nucleic acids may be the same or different depending on the context) may be combined with or amplified using a plurality of distinct BUMI domain containing nucleic acids that differ from each other at least with respect to the UMI portion of the BUMI tag or portion thereof present in the BUMI domain. As used herein, the term "distinct BUMI domain containing nucleic acids" may, in some instances, refer to a primer or template switch oligonucleotide that includes a BUMI domain. Accordingly, a BUMI domain may be appended to the amplification product of a reaction, e.g., by amplifying with a primer and/or a template switch oligonucleotide having a BUMI domain.

In some instances, combining a nucleic acid composition with a plurality of distinct BUMI domain containing nucleic acids facilitates the attachment of the BUMI domain containing nucleic acids to the individual nucleic acid molecules of the composition, e.g., through ligation or other method of attachment. For example, BUMI domain containing nucleic acids can be combined with a nucleic acid composition containing a plurality of different templates (e.g., RNA templates, DNA templates) or single product nucleic acids facilitating the attachment of the BUMI domain containing nucleic acids to the individual molecules of the plurality of templates or single product nucleic acids.

The number of unique combinations of the UMI portion of the BUMI tags or portions thereof of the BUMI domains can vary, and in some instances the number is 50 or more, e.g., 250 or more, including 500 or more, where in some instances the number is 1,000 or more, 5,000 or more, 10,000 or more, 50,000 or more, 100,000 or more, 250,000 or more, 500,000 or more, 1,000,000 or more, including 5,000,000 or more, such as 50,000,000 or more, including 100,000,000 or more, including 1,000,000,000 or more, wherein in some instances the number is 100,000,000 or less, such as 1,000,000 or less, such as 750,000 or less, including 500,000 or less. The number of unique combinations of the UMI portions of the BUMI tags or portions thereof of the BUMI domains can be a function of the number of UMI nucleotides of the BUMI tag. For example, if there are 10 UMI nucleotides in a BUMI TAG (e.g., dispersed through a BUMI among barcode nucleotides, e.g., as described above), then there are $4^{10}$ possible unique combinations of UMI nucleotides. Among the BUMI tags or portions thereof of the BUMI domains of such compositions, in some instances the differing BUMI tags or portions thereof of the composition have common barcode bases and different UMI nucleotides. In other words, the identity and position of each of the barcode bases in the differing BUMI tags or portions thereof of the BUMI domains is identical, but the identity of each of the UMI bases is different among 2 or more BUMI tags or portions thereof of BUMI domain-containing nucleic acids of the composition. For a given application, sets of BUMI tags can be chosen so that the barcode portion of each tag in the set has an equal C-G to A-T ratio, and thus eliminates differences in melting temperature between the BUMI tags. The set of BUMI tags may also be selected so that there is a minimum of three nucleotide differences between the barcode portion of each tag, thereby requiring a triple nucleotide sequence substitution before a molecule originating from one BUMI tagged sample becomes mis-identified as originating from a different sample.

As indicated above, a BUMI domain-containing nucleic acid may vary, e.g., with respect to either the BUMI domain component (which may include a complete BUMI tag or a portion thereof, where these tags or portions thereof may be encoded) or the other component(s) of the nucleic acid, such as primer binding domains, template switch domains, etc. Examples of different types of BUMI domain-containing nucleic acids are now reviewed in greater detail.

In some instances, a template switch oligonucleotide may include a BUMI domain, e.g., as described above. A BUMI domain containing template switch oligonucleotide may include a template switch domain and a BUMI domain, e.g., as described above (which may include a BUMI tag or portion thereof, and may or may not be encoded, e.g., as described in greater detail below). In some instances, a template switch domain may be or may include a 3' hybridization domain, as described above. The template switch domain may be positioned 3' of the BUMI domain (and any other domain of the template switch oligonucleotide).

An illustration of a template switch oligonucleotide having a BUMI domain is provided in FIG. 8. As shown in FIG. 8, the template switch oligonucleotide (800) includes a 3' hybridization, i.e., template switch, domain (801), optionally a 5' additional non-templated sequence domain (802) and a BUMI domain, e.g., as illustrated in FIG. 7A, having a BUMI tag (803) positioned between these two flanking domains, such that the BUMI domain is flanked by the template switch domain and the 5' additional non-templated sequence domain.

In some instances, a BUMI domain, e.g., as included in a primer or template switch oligonucleotide, may include a portion of a BUMI tag, where BUMI tag portions may also be referred to as split BUMIs. As the BUMI domains of the nucleic acids of these embodiments only include a portion of a BUMI tag, they do not include a complete BUMI tag. The portions of the BUMI tags of these embodiments include a percentage of the total number of nts of a BUMI tag of which they are a portion, where the percentage of nts in a given BUMI tag portion may vary, ranging in some instances from 10 to 95%, such as 15 to 75%, e.g., 40 to 60%, including 45 to 65%, wherein in some instances the percentage may be 50%, such that the BUMI tag portion is one half of a complete BUMI tag.

Nucleic acids that include BUMI domains having a portion of a BUMI tag find use in a variety of applications where it is desirable to split a BUMI tag among different nucleic acids. Having a long BUMI tag completely on one nucleic acid, e.g., a single product nucleic acid primer, a template switch oligonucleotide (TSO), etc., may interfere with one or more aspects of a given application or protocol, e.g., first strand synthesis, template switching efficiency, etc., and or result in more difficult reagent, e.g., primer, TSO, etc., synthesis. Splitting a BUMI tag among disparate nucleic acid reagents employed in a given protocol, e.g., a single product nucleic acid synthesis primer and a TSO allows for shorter BUMI domains to be used on each nucleic acid reagent while maintaining the diversity that accompanies a longer UMI. When using split BUMI tags in such embodiments, all portions of the BUMI tag, e.g., both halves of a BUMI tag, are sequenced to allow reconstruction of the full BUMI tag. Where desired, computer implemented algorithms may be employed to identify the barcode and UMI portions of each part of the split BUMI and thereby reconstruct the full BUMI tag.

As summarized above, in some instances, a primer such as a single product nucleic acid primer may include a BUMI domain. For example, FIG. 9 provides an illustration of a single product nucleic acid primer (900) that includes a BUMI domain, where e.g., in some instances the BUMI domain includes a portion of a BUMI tag. As illustrated, the nucleic acid (900) includes three domains, i.e., a BUMI domain (901) that, in the instant example includes a portion of a BUMI tag, a template binding domain (902) that hybridizes to a template nucleic acid and, optionally, an additional non-template sequence (NTS) domain (903) that does not hybridize to the template nucleic acid. The sequence of the first and second domains (i.e., the non-BUMI domains) may be independently defined or arbitrary. In certain aspects, the template binding domain (902) has a defined sequence (e.g., an oligo-dT sequence or an template-specific sequence) or an arbitrary sequence (e.g., a random sequence, such as a random hexamer sequence) and the sequence of the additional NTS domain (903) is defined.

In some instances, nucleic acids, e.g., primer and/or template switch oligonucleotides, may include an encoded BUMI domain. Encoded BUMI domains include a BUMI tag component, which may have a complete BUMI tag or portion thereof, e.g., as described above, and an encoding component that provides information about the order of the interspersed barcode and UMI nts in the BUMI tag component. As the encoding component provides information about the order of the interspersed barcode and UMI nts, it can be viewed as a scheme code that identifies the order of the barcode and UMI nts in the BUMI tag or BUMI tag portion. Accordingly, the sequence of the encoding component is used to determine which bases in the BUMI tag or portion thereof are barcode nts and which are UMI nts, such that the position of barcode nts and UMI nts in the BUMI tag can be determined from the encoding domain. Encoded BUMI domains find use in applications where great diversity of UMIs but shorter length of BUMI tags is desired. Longer UMIs provide greater diversity of unique sequences and allow for unique labeling of increased number of molecules. However, in some instances longer sequences are not desirable as they can lead to, for example, lower template switching efficiency or other complications. Encoded BUMI domains as described herein allow one to maintain diversity within a given population that is comparable to longer UMIs using BUMIs that are shorter. In this way, a pool of BUMIs can be shorter in length but still maintain diversity.

The encoding component of an encoded BUMI tag or portion thereof of a BUMI domain may vary in length, ranging in some instances from 1 to 10 nts, e.g., 1 to 5 nts, including 2 to 4 nts in length. The position of the encoding component may vary as desired, wherein some instances the encoding component is positioned 5' of the BUMI tag component and in other instances the encoding component is 3' of the BUMI tag component. The encoding component may or may not be separated from the BUMI tag component by an intervening base or sequence of bases. If present, such an intervening domain may vary in length, ranging in some instances from 1 to 3 nts, such as 1 to 2 nts.

FIG. 10 provides examples of encoded BUMI domains, where the encoded BUMI domain includes an encoding component and a BUMI tag component. In the encoded BUMI domains of FIG. 10, the encoding domains are 3 nts long, where each three base long encoding domain identifies a unique 8 nt long BUMI tag.

Encoded BUMI domains may be employed as any nucleic acid reagent of a given protocol, as desired. As such, encoded BUMI domains may be employed in nucleic acid primers, template switch oligonucleotides, etc., such as described above, where the encoded BUMI domains may include a complete BUMI tag or portion of a BUMI tag, e.g., as described above. In applications where encoded BUMI domains are employed, the sequence of the encoding component is employed to decode the BUMI tag component. Where desired, computer implemented algorithms may be employed to decode the encoding component, e.g., by identifying the pattern of barcode and UMI bases in the BUMI tag component, and therefore identify the barcode and UMI portions of the BUMI tag component (which may be complete BUMI tag or portion thereof, such as described above).

In some instances, a composition made up of a plurality of distinct BUMI domain-containing nucleic acids, e.g., where the distinct BUMI domains are or are not attached to primer (e.g., a single product nucleic acid primer) or a template switch oligonucleotide, may be employed in the subject methods, e.g., added to one or more of the herein described reaction mixtures. Distinct BUMI domain-containing nucleic acids making up a given plurality of such compositions are of differing sequence, at least with respect to their BUMI domains, and more specifically their UMI nts of the BUMI tags or portions thereof of their BUMI domains. As such, the plurality includes a number of distinct nucleic acids having differing BUMI tags or portions thereof of their BUMI domains. In some instances, the differing BUMI tags or portions thereof have common barcode nts and different UMI nts. In such instances, the identity and location of each of barcode nts of the BUMI tag or portion thereof of the BUMI domain is the same, i.e., is identical, among the differing BUMI tags or portions of thereof of the BUMI domains in the plurality, while the identity of the UMI nts at the remaining UMI locations of the BUMI tags or portions thereof vary, such that in any two distinct nucleic acids of the plurality, the identity, e.g., A, G, C or T, of at least one UMI nt at at least one UMI position of the BUMI tag or portion thereof of the BUMI domain is not the same, i.e., is not identical. The number of distinct BUMI domain-containing nucleic acids in a given composition may vary, and in some instances the number is 50 or more, e.g., 250 or more, including 500 or more, where in some instances the number is 1,000 or more, 5,000 or more, 10,000 or more, 50,000 or more, 100,000 or more, 250,000 or more, 500,000 or more, 1,000,000 or more, including 5,000,000 or more, including 100,000,000 or more, including 1,000,000,000 or more, wherein in some instances the number is 100,000,000 or less, such as 1,000,000 or less, such as 750,000 or less, including 500,000 or less.

Additional Method Parameters

The reaction mixture components are combined under conditions sufficient to produce a double stranded nucleic acid complex comprising a template nucleic acid and the template switch oligonucleotide hybridized to adjacent regions of a single product nucleic acid. Amplification is performed from the single product nucleic acid using the template switch oligonucleotide and the first stand cDNA primer under conditions sufficient to produce an amplified dsDNA.

By "conditions sufficient to produce a double stranded nucleic acid complex" is meant reaction conditions that permit the relevant nucleic acids in the reaction to interact (e.g., hybridize) with one another in the desired manner. Achieving suitable reaction conditions may include selecting reaction mixture components, concentrations thereof, and a reaction temperature to create an environment in which the relevant nucleic acids hybridize with one another in a sequence specific manner. For example, in addition to a template nucleic acid, a template switch oligonucleotide and a single product nucleic acid, the reaction mixture may include buffer components that establish an appropriate pH, salt concentration (e.g., KCl concentration), etc. Conditions sufficient to produce a double stranded nucleic acid complex may include those conditions appropriate for hybridization, also referred to as "hybridization conditions".

By "under conditions sufficient to produce an amplified dsDNA" is meant reaction conditions that permit polymerase-mediated extension of an end of a nucleic acid strand hybridized to a template. Suitable reaction conditions may include those that permit amplification polymerase-mediated extension, reverse transcriptase-mediated extension or both amplification polymerase-mediated and reverse transcriptase-mediated extension. Conditions sufficient to produce an amplified dsDNA may include conditions sufficient to produce the single product nucleic acid and one or more steps of a reaction may be performed under such conditions. Where reaction processes do not require reverse transcription (i.e., where a single product nucleic acid is provided to the reaction mixture) suitable reaction conditions need not be configured for both reverse transcription and amplification. Where a template nucleic acid (e.g., a DNA or a non-DNA template (e.g., a RNA template)) used to produce a single product nucleic acid is the starting material and the reaction is a one-step reaction, suitable reaction conditions will generally be those that permit both reverse transcription and PCR amplification.

Conditions sufficient to produce a single product nucleic acid may further include reaction conditions that permit template switching of a polymerase to the template switch oligonucleotide and continuation of the extension reaction to the 5' end of the template switch oligonucleotide.

Achieving suitable reaction conditions may include selecting reaction mixture components, concentrations thereof, and a reaction temperature to create an environment in which one or more polymerases are active and/or the relevant nucleic acids in the reaction interact (e.g., hybridize) with one another in the desired manner. In some instances, suitable reaction conditions may be configured such that two different polymerases are active including e.g., an amplification polymerase and a reverse transcriptase. In suitable reaction conditions, in addition to a template, one or more polymerases, a single product nucleic acid primer, a template switch oligonucleotide and dNTPs, the reaction mixture may include buffer components that establish an appropriate pH, salt concentration (e.g., KCl concentration), metal cofactor concentration (e.g., $Mg^{2+}$ or $Mn^{2+}$ concentration), and the like, for the extension reaction(s) and/or template switching to occur. Other components may be included, such as one or more nuclease inhibitors (e.g., an RNase inhibitor and/or a DNase inhibitor), one or more additives for facilitating amplification/replication of GC rich sequences (e.g., GC-Melt™ reagent (Clontech Laboratories, Inc. (Mountain View, Calif.)), betaine, DMSO, ethylene glycol, 1,2-propanediol, or combinations thereof), one or more molecular crowding agents (e.g., polyethylene glycol, or the like), one or more enzyme-stabilizing components (e.g., DTT present at a final concentration ranging from 1 to 10 mM (e.g., 5 mM)), and/or any other reaction mixture components useful for facilitating polymerase-mediated extension reactions and/or template-switching.

One or more reaction mixtures may have a pH suitable for a primer extension reaction and/or template-switching. In certain embodiments, the pH of the reaction mixture ranges from 5 to 9, such as from 7 to 9, including from 8 to 9, e.g., 8 to 8.5. In some instances, the reaction mixture includes a pH adjusting agent. pH adjusting agents of interest include, but are not limited to, sodium hydroxide, hydrochloric acid, phosphoric acid buffer solution, citric acid buffer solution, and the like. For example, the pH of the reaction mixture can be adjusted to the desired range by adding an appropriate amount of the pH adjusting agent.

The temperature range suitable for primer extension reactions may vary according to factors such as the particular polymerase employed, the melting temperatures of any primers employed, etc. In some instances, a reverse transcriptase (e.g., an MMLV reverse transcriptase) may be employed and the reaction mixture conditions sufficient for reverse transcriptase-mediated extension of a hybridized primer include bringing the reaction mixture to a temperature ranging from 4° C. to 72° C., such as from 16° C. to 70° C., e.g., 37° C. to 50° C., such as 40° C. to 45° C., including 42° C.

In some instances, the methods described herein may include denaturing the template, e.g., by subjecting a reaction mixture containing the template, e.g., RNA or DNA template, to a temperature sufficient to denature secondary structure of the template. Depending on the context, denaturing may take place before or after one or more reaction components have been added to the reaction mixture and, in some instances, is performed prior to the start of transcription, e.g., reverse transcription to generate the single product nucleic acid. Useful denaturing temperatures will vary and may range from less than 50° C. to more than 100° C., including but not limited to e.g., 50° C. or more, 55° C. or more, 65° C. or more, 70° C. or more, 72° C. or more, 75° C. or more, 80° C. or more, 85° C. or more, 90° C. or more, 95° C. or more, etc.

In some instances, the amplification reaction may be performed in the presence of one or more nucleic acid detection reagents, e.g., DNA dyes including fluorescent DNA dyes such as e.g., DAPI, Hoechst, PI, DRAQS, SYBR Green, LC Green, Eva Green, BEBO, BOXTO, SYTO9, and the like. Nucleic acid detection reagents, as referred to herein, include free DNA dyes, such as those listed above, as well as probe bound DNA dyes including but not limited to TaqMan probes, Molecular Beacons probes, Scorpions probes, Light-Up probes, and the like. In some instances, one or more nucleic acid detection reagents may be added to a reaction mixture and amplification may be performed, according to the methods described herein, such that the one or more nucleic acid detection reagents may be used to detect the presence of or monitor the production of amplified product dsDNA. As such, detecting the presence of the amplified dsDNA or quantifying the amount of amplified dsDNA may be based on the nucleic acid detection reagent. In some instances, amplification methods, as described herein may include quantitative PCR.

In some instances, e.g., where the amplification reaction is performed in an appropriate reaction vessel or a droplet, detection and/or quantification of the amplified dsDNA based on the nucleic acid detection reagent may be used in rapidly screening and/or sorting the amplification reactions. For example, a plurality of amplification reactions may be performed in a plurality of reaction vessels (e.g., multiple wells of a multi-well plate) in the presence of a nucleic acid detection reagent and the production of the amplified dsDNA may be performed based on the nucleic acid detection reagent to rapidly screen the wells (e.g., using a plate reader or similar device) and detect successful amplification reactions. In some instances, a plurality of amplification reactions may be performed in a plurality of droplets in the presence of a nucleic acid detection reagent and the droplets may be sorted (e.g., using a flow cytometer, using a microfluidic-based droplet sorter, etc.) based on the nucleic acid detection reagent.

In some instances, a specific nucleic acid detection reagent (e.g., a labeled probe specific for a particular nucleic acid sequence) may be employed for detecting the presence of a particular target sequence in the amplified product dsDNA. Such a probe may be added before, during or after the amplification reaction and may involve subjecting the reaction mixture to hybridizing conditions to hybridize a labeled probe to the amplified dsDNA. Useful probes may include but are not limited to e.g., fluorescence in situ hybridization (FISH) probes (e.g., DNA FISH probes, Riboprobes, LNA FISH probes, and the like). Labeled probes useful in detecting a specific target sequence will be complementary to the target sequence and when hybridized to the amplified dsDNA, may indicate the presence of the target sequence in the amplified dsDNA. In some instances, e.g., where the amplification reaction is performed in an appropriate reaction vessel or a droplet, detection and/or quantification of a target sequence in the amplified dsDNA based on the a labeled probe may be used in rapidly screening and/or sorting the amplification reactions, e.g., as described above regarding nucleic acid detection reagents.

In some instances, methods of the present disclosure may include isolating and/or purifying the amplified dsDNA product, including where the purifying is performed after, including only after, the amplification reaction has been performed (i.e., no intermediate component of the amplification reaction is purified). Any convenient method of purification may be employed including but not limited to e.g., nucleic acid precipitation (i.e., alcohol precipitation), gel purification, etc.

In some instances, a solid support (e.g., a bead, a plate, etc.) may be utilized in the present methods. For example, in some instances, a single product nucleic acid primer may be attached to a solid support and used in an amplification reaction, as described herein. In some instances, a template switch oligonucleotide may be attached to a solid support and used in an amplification reaction, as described herein. Solid support attached single product nucleic acid primer and/or template switch oligonucleotide may be utilized in isolating the amplified dsDNA, e.g., by collecting the bead during or after the reaction while the support-attached nucleotide is hybridized to one or more components or intermediates of the reaction. Any convenient method of collecting support-attached nucleic acids may be employed including but not limited to e.g., magnetic separation, density/centrifuge/gravity based separation, filtration based separation, molecular binding based separation, fluorescence based separation (i.e., based on fluorescence of the solid support), etc.

Nucleic acids, e.g., template switch oligonucleotides and/or single product nucleic acid primers, may be synthesized directly on the solid support or may be chemically attached or "captured". For example, in some instances, one or more nucleic acids of the subject methods, e.g., template switch oligonucleotides and/or single product nucleic acid primers, may include a caged capture moiety (e.g., caged biotin, caged fluorescein, etc.) that, when uncaged, binds the nucleic acid to a corresponding binding partner (e.g., anti-biotin antibody, avidin, streptavidin, NEUTRAVIDIN®, an anti-fluorescein antibody, etc.). present on the solid support. The amplification reaction may be performed such that the caged capture moiety is incorporated into the amplified dsDNA product allowing attachment of the amplified dsDNA product to a solid support by uncaging the capture moiety under conditions sufficient for the uncaged capture moiety to bind its binding partner present on the solid support. Methods and reagents useful in caged capture of nucleic acid include but are not limited to e.g., those described in U.S. Pat. No. 7,947,477; the disclosure of which is incorporated herein by reference in its entirety.

A non-limiting example a caged capture moiety attached to the template switch oligonucleotide is depicted in FIG. 11. As depicted, a produced dsDNA (1100), e.g., as schematized in FIG. 5, further includes a caged capture moiety (1101). Prior to uncaging (1102), the caged capture moiety does not bind its corresponding binding partner (1103) attached to a solid support, which in the instant example is represented by a bead (1104). Following uncaging (1105), the uncaged capture moiety (1101) is free to bind its corresponding binding partner (1103), thus facilitating capture of the produced dsDNA (1100).

Single Cells, Reaction Vessels and Droplets

Reaction vessels into which the reaction mixtures and components thereof may be added and within which the reactions of the subject methods may take place will vary. Useful reaction vessels include but are not limited to e.g., tubes (e.g., single tubes, multi-tube strips, etc.), wells (e.g., of a multi-well plate (e.g., a 96-well plate, 384 well plate, or a plate with any number of wells such as 2000, 4000, 6000, or 10000 or more). Multi-well plates may be independent or may be part of a chip and/or device. Multi-well plates may be independent or may be part of a chip and/or device.

In certain embodiments, a reaction vessel employed may be a well or wells of a multi-well device. The present disclosure is not limited by the type of multi-well devices (e.g., plates or chips) employed. In some instances, such devices have a plurality of wells that contain, or are dimensioned to contain, liquid (e.g., liquid that is trapped in the wells such that gravity alone cannot make the liquid flow out of the wells). One exemplary chip is the 5184-well SMART-CHIP™ sold by WAFERGEN™ (WaferGen Biosystems, Inc.). Other exemplary chips are provided in U.S. Pat. Nos. 8,252,581; 7,833,709; and 7,547,556, all of which are herein incorporated by reference in their entireties including, for example, for the teaching of chips, wells, thermocycling conditions, and associated reagents used therein). Other exemplary chips include the OPENARRAY™ plates used in the QUANTSTUDIO™ real-time PCR system (sold by Applied Biosystems). Another exemplary multi-well device is a 96-well or 384-well plate.

In some instances, reaction mixtures and components thereof may be added to the reactions of the subject methods in a liquid droplet (e.g., a water-oil emulsion droplet), e.g., as described in more detail below. Whereas the droplets may serve the purpose of individual reaction vessels, the droplets (or emulsion containing droplets) will generally be housed in a suitable container such as, e.g., a tube or well or microfluidic channel. Amplification reactions performed in droplets may be sorted, e.g., based on fluorescence (e.g., from nucleic acid detection reagent or labeled probe), using a fluorescence based droplet sorter. Useful fluorescence based droplet sorters will vary and may include e.g., a flow cytometers, microfluidic-based droplet sorters, and the like. In some instances, reaction mixtures and components thereof may be added to the reactions of the subject methods using a multi sample nanodispenser. The dispenser may be able to dispense multiple reactions at a time and may dispense multiple volumes into the reactions (e.g., may dispense 35 nL, 50 nL, 75 nL, etc).

In some instances, emulsion PCR may be employed. For emulsion PCR, an emulsion PCR reaction (e.g., in a droplet, droplet microreactor) is created with a "water in oil" mix to generate thousands or millions of micron-sized aqueous compartments. Sources of nucleic acids (e.g., cells, nucleic acid libraries, optionally coupled to solid supports, e.g., beads) are mixed in a limiting dilution prior to emulsification or directly into the emulsion mix. The combination of compartment size and limiting dilution of the nucleic acid sources is used to generate compartments containing, on average, just one source of nucleic acid (e.g., cell, or sample nucleic acid(s), such as cellular nucleic acid—e.g., RNA or DNA combined with a solid support, such that the nucleic acids may be stably associated with the solid support (e.g., bead) etc.). Depending on the size of the aqueous compartments generated during the emulsification step, up to $3 \times 10^9$ individual amplification reactions per μl can be conducted simultaneously in the same container, e.g., tube, well or other suitable container. The average size of a compartment in an emulsion ranges from sub-micron in diameter to over a 100 microns, depending on the emulsification conditions.

As indicated above, in protocols that include a pooling step, the pooling step can be performed after or before amplification to produce a dsDNA product, e.g., from a single cell, from a droplet, etc. As such, in certain embodiments of the methods described herein, cells are obtained from a tissue of interest and a single-cell suspension is obtained. A single cell is placed in one well of a multi-well plate, or other suitable container, such as a microfluidic chamber or tube. The cells are lysed and reaction mixture is added directly to the lysates, e.g., without additional purification. In yet other embodiments, cells are obtained from a tissue of interest and a single-cell suspension is obtained. A single cell is placed in one well of a multi-well plate or other suitable container. The cells are lysed and reaction mix is added directly to the lysates, e.g., without additional purification. The amplified dsDNA samples may or may not be pooled and, in some instances, may then be sequenced to produce reads. This may allow identification of genes that are expressed in each single cell.

In some instances, the methods may include the step of obtaining single cells. Obtaining single cells may be done according to any convenient protocol. A single cell suspension can be obtained using standard methods known in the art including, for example, enzymatically using trypsin or papain to digest proteins connecting cells in tissue samples or releasing adherent cells in culture, or mechanically separating cells in a sample. Single cells can be placed in any suitable reaction vessel in which single cells can be treated individually. For example a 96-well plate, 384 well plate, or a plate with any number of wells such as 2000, 4000, 6000, or 10000 or more. The multi-well plate can be part of a chip and/or device. The present disclosure is not limited by the number of wells in the multi-well plate. In various embodiments, the total number of wells on the plate is from 100 to 200,000, or from 5000 to 10,000. In other embodiments the plate comprises smaller chips, each of which includes 5,000 to 20,000 wells. For example, a square chip may include 125 by 125 nanowells, with a diameter of 0.1 mm.

In certain embodiments of the methods described herein, droplets are obtained and a single droplet is sorted into one well of a multi-well plate, or other suitable container, such as a microfluidic chamber or tube. The reaction mixture may be added directly to the droplet, e.g., without additional purification. The amplified dsDNA samples may or may not be pooled and, in some instances, may then be sequenced to produce reads. This may allow identification of nucleic acids representing genes or expressed nucleic acids contained within a single droplet.

In some instances, the methods may include the step of obtaining single droplets. Obtaining droplets cells may be done according to any convenient protocol, including e.g., mechanically sorting droplets (e.g., utilizing a fluorescence based sorter (e.g., a flow cytometer or microfluidic-based sorter). Single droplets can be placed in any suitable reaction vessel in which single droplets can be treated individually. For example a 96-well plate, 384 well plate, or a plate with any number of wells such as 2000, 4000, 6000, or 10000 or more. The multi-well plate can be part of a chip and/or device. The present disclosure is not limited by the number of wells in the multi-well plate. In various embodiments, the total number of wells on the plate is from 100 to 200,000, or from 5000 to 10,000. In other embodiments the plate comprises smaller chips, each of which includes 5,000 to 20,000 wells. For example, a square chip may include 125 by 125 nanowells, with a diameter of 0.1 mm.

The wells (e.g., nanowells) in the multi-well plates may be fabricated in any convenient size, shape or volume. The well may be 100 μm to 1 mm in length, 100 μm to 1 mm in width, and 100 μm to 1 mm in depth. In various embodiments, each nanowell has an aspect ratio (ratio of depth to width) of from 1 to 4. In one embodiment, each nanowell has an aspect ratio of 2. The transverse sectional area may be circular, elliptical, oval, conical, rectangular, triangular, polyhedral, or in any other shape. The transverse area at any given depth of the well may also vary in size and shape.

In certain embodiments, the wells have a volume of from 0.1 nl to 1 μl. The nanowell may have a volume of 1 μl or less, such as 500 nl or less. The volume may be 200 nl or less, such as 100 nl or less. In an embodiment, the volume of the nanowell is 100 nl. Where desired, the nanowell can be fabricated to increase the surface area to volume ratio, thereby facilitating heat transfer through the unit, which can reduce the ramp time of a thermal cycle. The cavity of each well (e.g., nanowell) may take a variety of configurations. For instance, the cavity within a well may be divided by linear or curved walls to form separate but adjacent compartments, or by circular walls to form inner and outer annular compartments.

The wells can be designed such that a single well includes a single cell or a single droplet. An individual cell or droplet may also be isolated in any other suitable container, e.g., microfluidic chamber, droplet, nanowell, tube, etc. Any convenient method for manipulating single cells or droplets may be employed, where such methods include fluorescence activated cell sorting (FACS), robotic device injection, gravity flow, or micromanipulation and the use of semi-automated cell pickers (e.g. the Quixell™ cell transfer system from Stoelting Co.), etc. In some instances, single cells or droplets can be deposited in wells of a plate according to Poisson statistics (e.g., such that approximately 10%, 20%, 30% or 40% or more of the wells contain a single cell or droplet—which number can be defined by adjusting the number of cells or droplets in a given unit volume of fluid that is to be dispensed into the containers). In some instances, a suitable reaction vessel comprises a droplet (e.g., a microdroplet). Individual cells or droplets can, for example, be individually selected based on features detectable by microscopic observation, such as location, morphology, the presence of a reporter gene (e.g., expression), the presence of a bound antibody (e.g., antibody labelling), FISH, the presence of an RNA (e.g., intracellular RNA labelling), or qPCR.

Following obtainment of single cells, e.g., as described above, DNA or RNA (e.g., mRNA) can be released from the cells by lysing the cells. Lysis can be achieved by, for example, heating or freeze-thaw of the cells, or by the use of detergents or other chemical methods, or by a combination of these. However, any suitable lysis method can be used. In some instances, a mild lysis procedure can advantageously be used to prevent the release of nuclear chromatin, thereby avoiding genomic contamination of a cDNA library, and to minimize degradation of mRNA. For example, heating the cells at 72° C. for 2 minutes in the presence of Tween-20 is sufficient to lyse the cells while resulting in no detectable genomic contamination from nuclear chromatin. Alternatively, cells can be heated to 65° C. for 10 minutes in water (Esumi et al., Neurosci Res 60(4):439-51 (2008)); or 70° C. for 90 seconds in PCR buffer II (Applied Biosystems) supplemented with 0.5% NP-40 (Kurimoto et al., Nucleic Acids Res 34(5):e42 (2006)); or lysis can be achieved with a protease such as Proteinase K or by the use of chaotropic salts such as guanidine isothiocyanate (U.S. Publication No. 2007/0281313). In some instances, a lysis procedure may preferentially enrich for DNA from single cells, including e.g., where RNase is utilized.

Synthesis of single product nucleic acid from template nucleic acid in the methods described herein can be performed directly on cell lysates, such that a reaction mix for reverse transcription is added directly to cell lysates. Alternatively, nucleic acid template can be purified after its release from cells. This can help to reduce contamination of nucleic acid species that may be undesired in a particular protocol including e.g., mitochondrial and ribosomal nucleic acid contamination. Desired nucleic acid purification (e.g., DNA purification, mRNA purification) can be achieved by any method known in the art, for example, by binding the desired nucleic acid to a solid phase. Commonly used purification methods include paramagnetic beads (e.g. Dynabeads). Alternatively, specific contaminants, such as ribosomal RNA can be selectively removed using affinity purification, degradation of the contaminating nucleic acid (e.g., using a RiboGone™ (Takara Bio USA Inc., Mountain View, Calif.) and those methods described in U.S. Pat. No. 9,428,794 and U.S. Patent Application Pub. No. US 2015/0225773 A1; the disclosures of which are incorporated herein by reference in their entirety), combinations thereof, and the like.

Where desired, a given single cell or droplet workflow may include a pooling step where a nucleic acid product composition, e.g., made up of synthesized single product nucleic acids or synthesized dsDNAs, is combined or pooled with the nucleic acid product compositions obtained from one or more additional cells or droplets. The number of different nucleic acid product compositions produced from different cells or droplets that are combined or pooled in such embodiments may vary, where the number ranges in some instances from 2 to 50, such as 3 to 25, including 4 to 20 or 10,000, or more.

Libraries

In certain embodiments, the subject methods may be used to generate a library of amplified nucleic acids of interest (e.g., an amplified dsDNA library, an amplified cDNA library, etc.). Such libraries may find use in a variety of different applications.

In some instances, the subject methods may be used to generate a library of amplified nucleic acids for downstream sequencing on a sequencing platform of interest (e.g., a sequencing platform provided by Illumina®, Ion Torrent™, Pacific Biosciences, Life Technologies™, Roche, or the like). For example, the described methods may be performed to amplify a plurality of different nucleic acids in a nucleic acid sample of interest, such that product dsDNAs corresponding to at least a portion of the plurality of different nucleic acids are generated. Sequencing platform adapter constructs may then be attached to the ends of these amplified product dsDNAs or derivatives thereof, according to any convenient strategy. After attachment of the adapter constructs, these nucleic acid species may be inputted directly for sequencing on a sequencing platform of interest or the amplified nucleic acids may be further processed prior to sequencing.

According to certain embodiments, the subject methods are used to generate an amplified cDNA library corresponding to polyadenylated or non-polyadenylated RNAs for downstream sequencing on an Illumina®-based sequencing system. In one embodiment, microRNAs, including e.g., microRNAs that have been artificially polyadenylated, are used as templates in a template switch polymerization and amplification reaction as described herein. The amplified product nucleic acids may be used for adapter construct attachment and subsequent sequencing. In such embodiments, the number of distinct nucleic acids of differing sequence in the library may vary, and in some instances may range from 2 to 100,000 (e.g., from 30,000 to 100,000), such as from 50 to 25,000, from 100 to 10,000, or from 150 to 5,000, e.g., from 200 to 1000.

In some instances, amplified nucleic acids are produced from a plurality of template nucleic acids obtained from a single cell to generate a single cell amplified nucleic acid library. Such single cell libraries may then be employed in further downstream applications, such as sequencing applications. As used herein, a "single cell" refers to one cell. Single cells useful as the source of template RNAs and/or in generating single cell libraries of amplified nucleic acids can be obtained from a tissue of interest, or from a biopsy, blood sample, or cell culture. Additionally, cells from specific organs, tissues, tumors, neoplasms, or the like can be obtained and used in the methods described herein. Furthermore, cells from any population can be used in the subject methods, such as a population of prokaryotic or eukaryotic single celled organisms including bacteria or yeast.

Produced libraries, whether single-cell or multi-cell libraries, of amplified dsDNA product, produced according to the methods described herein, may be further utilized in a variety of ways. For example, in some instances, the individual components of a subject library may be cloned, e.g., into one or more vectors, to generate a vector library, including e.g., an expression vector library, a sequencing library, etc. In some instances, the library as a whole or a substantial portion thereof may be directly used in a sequencing protocol, including e.g., a next generation sequencing (NGS) protocol.

In certain aspects, the methods of the present disclosure further include subjecting a NGS library to an NGS protocol. The protocol may be carried out on any suitable NGS sequencing platform. NGS sequencing platforms of interest include, but are not limited to, a sequencing platform provided by Illumina® (e.g., the HiSeq™ MiSeq™ and/or NextSeq™ sequencing systems); Ion Torrent™ (e.g., the Ion PGM™ and/or Ion Proton™ sequencing systems); Pacific Biosciences (e.g., the PACBIO RS II Sequel sequencing system); Life Technologies™ (e.g., a SOLiD sequencing system); Roche (e.g., the 454 GS FLX+ and/or GS Junior sequencing systems); or any other sequencing platform of interest. The NGS protocol will vary depending on the particular NGS sequencing system employed. Detailed protocols for sequencing an NGS library, e.g., which may include further amplification (e.g., solid-phase amplification), sequencing the amplicons, and analyzing the sequencing data are available from the manufacturer of the NGS sequencing system employed.

Compositions

Aspects of the invention also include compositions, e.g., as described above. The subject compositions may include, e.g., one or more of any of the reaction mixture components described above with respect to the subject methods. For example, the compositions may include one or more of a template nucleic acid (e.g., a template RNA, a template DNA, etc.), an amplification polymerase (e.g., a thermostable polymerase, etc.), a reverse transcriptase (e.g., a reverse transcriptase capable of template-switching, etc.), a template switch oligonucleotide, dNTPs, a salt, a metal cofactor, one or more nuclease inhibitors (e.g., an RNase inhibitor), one or more enzyme-stabilizing components (e.g., DTT), or any other desired reaction mixture component(s), where the nucleic acid reagents, e.g., primers, template switch oligonucleotides, etc., may include one or more nucleic acid domains not directly utilized in the RT and amplification reactions described above including but not limited to e.g., a non-templated domain (e.g., a primer binding domain, a barcode domain, a restriction enzyme recognition site domain, a BUMI domain, etc.).

The subject compositions may be present in any suitable environment. According to one embodiment, the composition is present in a reaction tube (e.g., a 0.2 mL tube, a 0.6 mL tube, a 1.5 mL tube, or the like) or a well or microfluidic chamber or droplet or other suitable container. In certain aspects, the composition is present in two or more (e.g., a plurality of) reaction tubes or wells (e.g., a plate, such as a 96-well plate, a multi-well plate, e.g., containing about 1000, 5000, or 10,000 or more wells). The tubes and/or plates may be made of any suitable material, e.g., polypropylene, or the like, PDMS, or aluminum. The containers may also be treated to reduce adsorption of nucleic acids to the walls of the container. In certain aspects, the tubes and/or plates in which the composition is present provide for efficient heat transfer to the composition (e.g., when placed in a heat block, water bath, thermocycler, and/or the like), so that the temperature of the composition may be altered within a short period of time, e.g., as necessary for a particular enzymatic reaction to occur. According to certain embodiments, the composition is present in a thin-walled polypropylene tube, or a plate having thin-walled polypropylene wells or materials such as aluminum having high heat conductance. In some instances, the compositions of the disclosure may be present in droplets. In certain embodiments it may be convenient for the reaction to take place on a solid surface or a bead, in such case, the single product nucleic acid primer and/or template switch oligonucleotide, or one or more other primers, may be attached to the solid support or bead by methods known in the art—such as biotin linkage or by covalent linkage—and reaction allowed to proceed on the support. Alternatively, the oligos may be synthesized directly on the solid support—e.g. as described in Macosko, E Z et. al, Cell 161, 1202-1214, May 21, 2015).

Other suitable environments for the subject compositions include, e.g., a microfluidic chip (e.g., a "lab-on-a-chip device", e.g., a microfluidic device comprising channels and inlets). The composition may be present in an instrument configured to bring the composition to a desired temperature, e.g., a temperature-controlled water bath, heat block, heat block adaptor, or the like. The instrument configured to bring the composition to a desired temperature may be configured to bring the composition to a series of different desired temperatures, each for a suitable period of time (e.g., the instrument may be a thermocycler).

Kits

Aspects of the present disclosure also include kits. The kits may include, e.g., one or more of any of the reaction mixture components described above with respect to the subject methods. For example, the kits may include a template nucleic acid, an amplification polymerase (e.g., a thermostable polymerase, etc.), a reverse transcriptase (e.g., a reverse transcriptase capable of template-switching, etc.), a template switch oligonucleotide, a single product nucleic acid primer, dNTPs, a salt, a metal cofactor, one or more nuclease inhibitors (e.g., an RNase inhibitor and/or a DNase inhibitor), one or more molecular crowding agents (e.g., polyethylene glycol, or the like), one or more enzyme-stabilizing components (e.g., DTT), or any other desired kit component(s).

In some instances, components of the subject kits may be presented as a "cocktail" where, as used herein, a cocktail refers to a collection or combination of two or more different but similar components in a single vessel. Useful cocktails in the subject kits include but are not limited to e.g., "primer cocktails" where the composition of such cocktails may vary and may include e.g., a cocktail of two or more primers including e.g., a single product nucleic acid primer (e.g., CDS primer) and a template switch oligonucleotide. Useful cocktails in the subject kits may also include but are not limited to e.g., "polymerase cocktails" where the composition of such cocktails may vary and may include e.g., a cocktail of two or more polymerases including e.g., an amplification polymerase and a reverse transcriptase.

In certain embodiments, the kits include reagents for isolating DNA or RNA from a nucleic acid source of interest. The reagents may be suitable for isolating nucleic acid samples from a variety of DNA or RNA sources including single cells, cultured cells, tissues, organs, or organisms. The subject kits may include reagents for isolating a nucleic acid sample from a fixed cell, tissue or organ, e.g., formalin-fixed, paraffin-embedded (FFPE) tissue. Such kits may include one or more deparaffinization agents, one or more agents suitable to de-crosslink nucleic acids, and/or the like.

Components of the kits may be present in separate containers, or multiple components may be present in a single container. For example, the template switch oligonucleotide and the single product nucleic acid primer may be provided in the same tube, or may be provided in different tubes. In some instances, the reverse transcriptase and the amplification polymerase may be provided in the same tube, or may be provided in different tubes. In some instances, one or more of the template switch oligonucleotide and the single product nucleic acid primer and the amplification polymerase may be provided in the same tube, or may be provided in different tubes. In some instances, the reverse transcriptase, the amplification polymerase, the single product nucleic acid primer and the template switch oligonucleotide may be provided in the same tube, or may be provided in individual tubes or combinations thereof may be combined into the same tube. In some instances, deoxyribonucleotide triphosphates (dNTPs) may be included in the same tube as the reverse transcriptase, the amplification polymerase, the single product nucleic acid primer or the template switch oligonucleotide or a tube containing some combination of the reverse transcriptase, the amplification polymerase, the single product nucleic acid primer and/or the template switch oligonucleotide.

In addition to the above-mentioned components, a subject kit may further include instructions for using the components of the kit, e.g., to practice the subject methods as described above. In addition, e.g., where the primers and/or oligonucleotides of a kit include a BUMI domain, the kit may further include programming for analysis of results including, e.g., decoding encoded BUMI domains, counting unique molecular species, etc. The instructions and/or analysis programming are generally recorded on a suitable recording medium. The instructions and/or programming may be printed on a substrate, such as paper or plastic, etc. As such, the instructions may be present in the kits as a package insert, in the labeling of the container of the kit or components thereof (i.e., associated with the packaging or sub-packaging) etc. In other embodiments, the instructions are present as an electronic storage data file present on a suitable computer readable storage medium, e.g. CD-ROM, diskette, Hard Disk Drive (HDD) etc. In yet other embodiments, the actual instructions are not present in the kit, but means for obtaining the instructions from a remote source, e.g. via the internet, are provided. An example of this embodiment is a kit that includes a web address where the instructions can be viewed and/or from which the instructions can be downloaded. As with the instructions, this means for obtaining the instructions is recorded on a suitable substrate.

Utility

The subject methods find use in a variety of applications, including those that require amplification of dsDNA product from a starting sample containing a template nucleic acid. The instant methods further find use in those methods where minimal user input and "hands-on time" is desired to achieve an amplified dsDNA product. The shortened protocols of the instant methods (i.e., those requiring only one or two steps, as described above, limit the user interaction with the reaction thus reducing the potential for contamination).

The subject methods may further be employed where reaction efficiency and/or specificity is desired. In some embodiments, the amplification reactions described herein make use of only a single set of primers from single product nucleic acid synthesis through amplification, namely the template switch oligonucleotide and the single product nucleic acid primer. As such the subject reactions reduce primer competition and may, in some instances, increase reaction efficiency and/or specificity.

Applications of the subject methods include medical and research applications where the detection of particular nucleic acid entities, e.g., pathogen RNAs (e.g., viral RNAs, bacterial RNAs, fungal RNA, parasite RNAs, etc.), pathogen DNAs (e.g., viral DNAs, bacterial DNAs, fungal DNAs, parasite DNAs, etc.), microRNAs, mRNAs, disease related DNA or genomic mutations, disease related RNA and/or mutant transcripts, is desired. Applications of the subject methods also include medical and research applications where an entire population of nucleic acids is to be surveyed, including e.g., where nucleic acid diversity is surveyed, where nucleic acid expression levels are surveyed, where nucleic acid copy number is surveyed, etc. The subject methods also find use in biotechnological applications including cloning, expression studies, etc.

Such applications exist in the areas of basic research and diagnostics (e.g., clinical diagnostics) and include, but are not limited to, the generation of sequencing-ready libraries of nucleic acids of interest, suppression PCR, cloning, detection, library amplification, array hybridization, whole genome amplification, and/or the like. The sequencing-ready libraries include adapter sequences that enable sequencing of the library members using any convenient sequencing platform, including: the HiSeq™ MiSeq™ and Genome Analyzer™ sequencing systems from Illumina®; the Ion PGM™ and Ion Proton™ sequencing systems from Ion Torrent™; the PACBIO RS II or Sequel sequencing system from Pacific Biosciences, the SOLiD sequencing systems from Life Technologies™, the 454 GS FLX+ and GS Junior sequencing systems from Roche, or any other convenient sequencing platform. The methods of the present disclosure find use in generating sequencing ready libraries corresponding to any DNA or RNA starting material of interest, e.g., genomic DNA, mRNA, non-polyadenylated RNA (e.g., microRNA). For example, the subject methods may be used to generate sequencing-ready cDNA libraries from non-polyadenylated RNAs, including microRNAs, small RNAs, siRNAs, and/or any other type non-polyadenylated RNAs of interest.

The following examples are offered by way of illustration and not by way of limitation.

EXAMPLES

Example 1: One-Step RT-PCR with Template Switching and Amplification

Current RT-PCR assays use a three-step protocol. The first step is a heat denaturation step that removes secondary structure and anneals the reverse transcription oligo to the template. In the second step, reagents are added for the reverse transcription (RT) reaction, which step generates first strand complementary DNA (cDNA) (i.e., "first strand cDNA synthesis"). In the third step, reagents are added for the PCR amplification, which step generates double-stranded cDNA and amplified copies.

The instant example describes shortened RT-PCR protocols, as compared e.g., to the three-step described above, utilizing template switching and ultimately generating amplified double-stranded cDNA product. The thermo cycling steps and reaction components of a typical three-step RT-PCR protocol utilizing template switching is provided below in Table 1 for reference:

TABLE 1

| Step | | Temp (° C.) | Time | | Reaction Components: | Vol. (µl) |
|---|---|---|---|---|---|---|
| 1 | Preheat | 72 | 3 min. | | RT mix | 20 |
| 2 | RT | 42 | 90 min. | | DNA polymerase | 1 |
| | | 70 | 10 min. | | 2x PCR buffer | 25 |
| 3 | PCR | 95 | 1 min. | | Amplification primer | 1 |
| | | 98 | 10 sec. | 17 cycles | Water | 3 |
| | | 65 | 30 sec. | | | |
| | | 68 | 3 min. | | | |
| | | 72 | 10 min. | | | |

The described shortened protocols utilize the RT oligonucleotide and the template switch oligonucleotide (TSO) as primers for PCR amplification, eliminating the need for amplification primers. Accordingly, a two-step template switching RT-PCR protocol was developed, the thermocycling steps of which are generally described as follows:
1. Preheat at 72° C. for 3 min.
2. RT-PCR: 42° C. for 90 min., 95° C. for 1 min., 17-18 cycles of (98° C. for 10 sec., 65° C. for 15 sec., 68° C. for 3 min.).

A single step template switching RT-PCR protocol was also developed, the thermocycling steps of which are generally described as follows:
1. 42° C. for 90 min., 95° C. for 1 min., 17-18 cycles of (98° C. for 10 sec., 65° C. for 15 sec., 68° C. for 3 min.).

In the instant example, a hot-start DNA amplification polymerase was utilized, which is inactive at 42° C., during the reverse transcription (RT). Thus, heating to 95° C. for 1 min., as above, activates the DNA polymerase for amplification (e.g., by removing the inactivating antibody present on the polymerase). Heating the reaction to 95° C. also serves to inactivate the reverse transcriptase following first strand synthesis.

The shortened protocols do not require the addition of extra primers, buffer(s), or polymerase(s) into the reaction mixture beyond those initially added to the reaction mix (i.e., there is no requirement to add additional components during the reaction (e.g., between starting the reaction and before the final product is produced). The DNA amplification polymerase used in the instant example was also a thermostable polymerase. The following shortened protocols ("Two Step Protocol" (Table 2) and "One Step Protocol" (Table 3)) and associated reaction components were used to amplify double-stranded cDNA from a test template mRNA and compared to the amplification of the same template mRNA achieved using the above provided 3 step protocol.

TABLE 2

Two Step Protocol:

| Step | | Temp (° C.) | Time | | Reaction Components: | Vol. (μl) |
|---|---|---|---|---|---|---|
| 1 | Preheat | 72 | 3 min. | | RT mix | 20 |
| 2 | RT & PCR | 42 | 90 min. | | DNA polymerase | 1 |
| | | 95 | 1 min. | | 2x PCR buffer | 4 |
| | | 98 | 10 sec. | 17 cycles | | |
| | | 65 | 30 sec. | | | |
| | | 68 | 3 min. | | | |
| | | 72 | 10 min. | | | |

TABLE 3

One Step Protocol:

| Step | | Temp (° C.) | Time | | Reaction Components: | Vol. (μl) |
|---|---|---|---|---|---|---|
| 1 | RT & PCR | (50) | (1 min.) | | RT mix | 20 |
| | | 42 | 90 min. | | DNA polymerase | 1 |
| | | 95 | 1 min. | | 2x PCR buffer | 4 |
| | | 98 | 10 sec. | 17 cycles | | |
| | | 65 | 30 sec. | | | |
| | | 68 | 3 min. | | | |
| | | 72 | 10 min. | | | |

Figure 12:
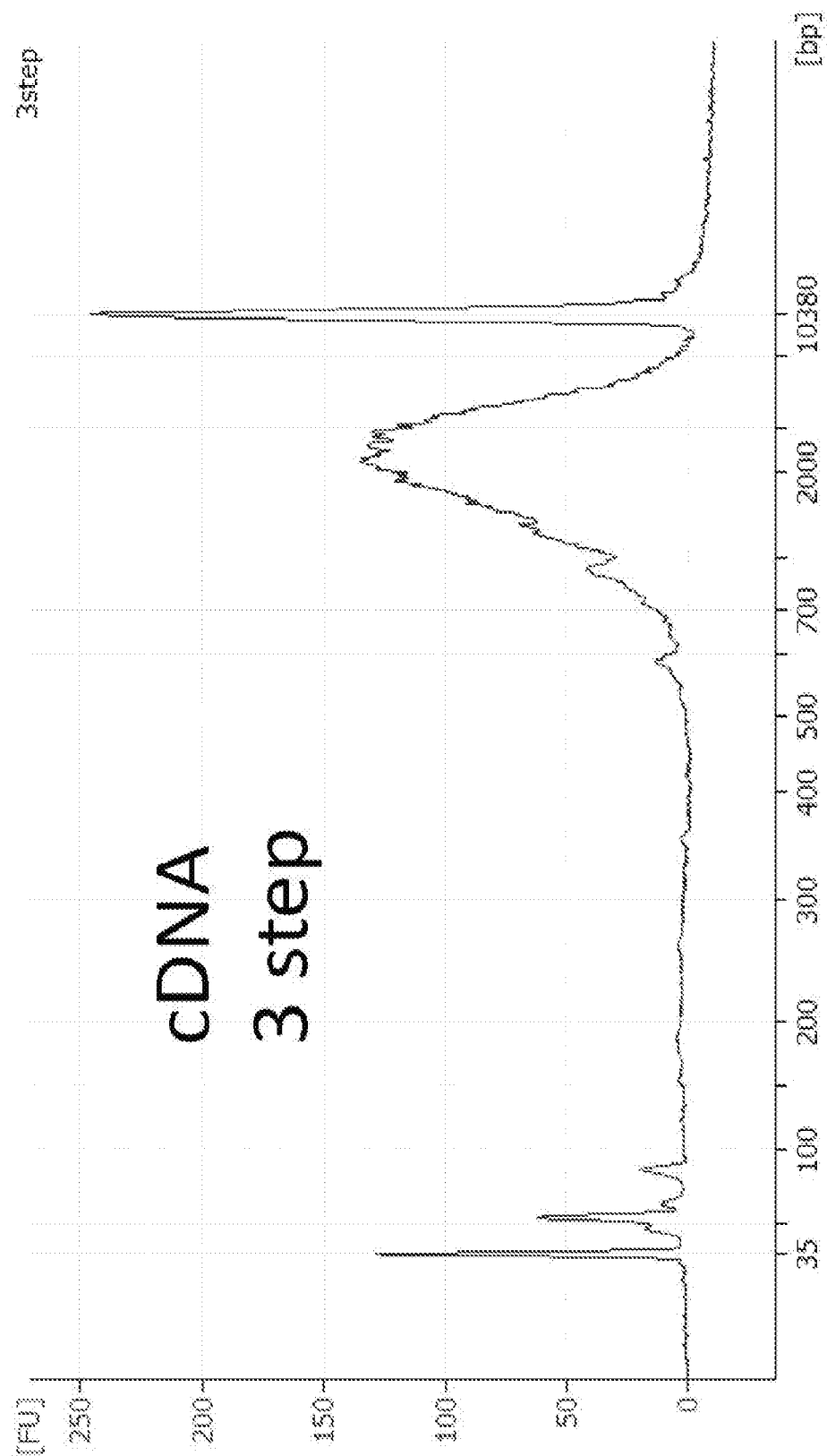
FIG. 12 provides the sequence length distribution of the amplified double-stranded cDNA product of a three-step RT-PCR protocol as described herein.
Figure 13:
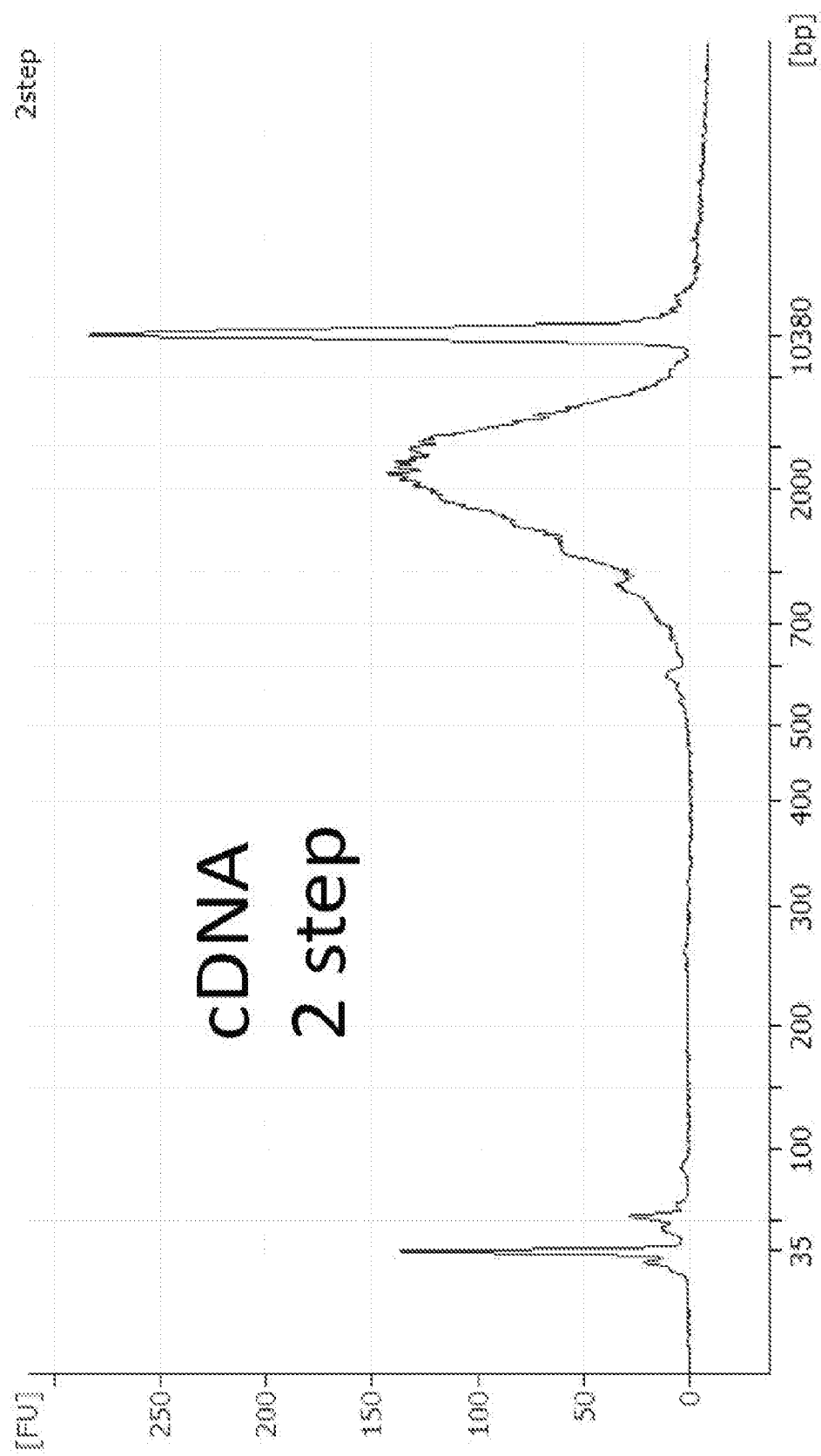
FIG. 13 provides the sequence length distribution of the amplified double-stranded cDNA product of a two-step RT-PCR protocol as described herein.
Figure 14:
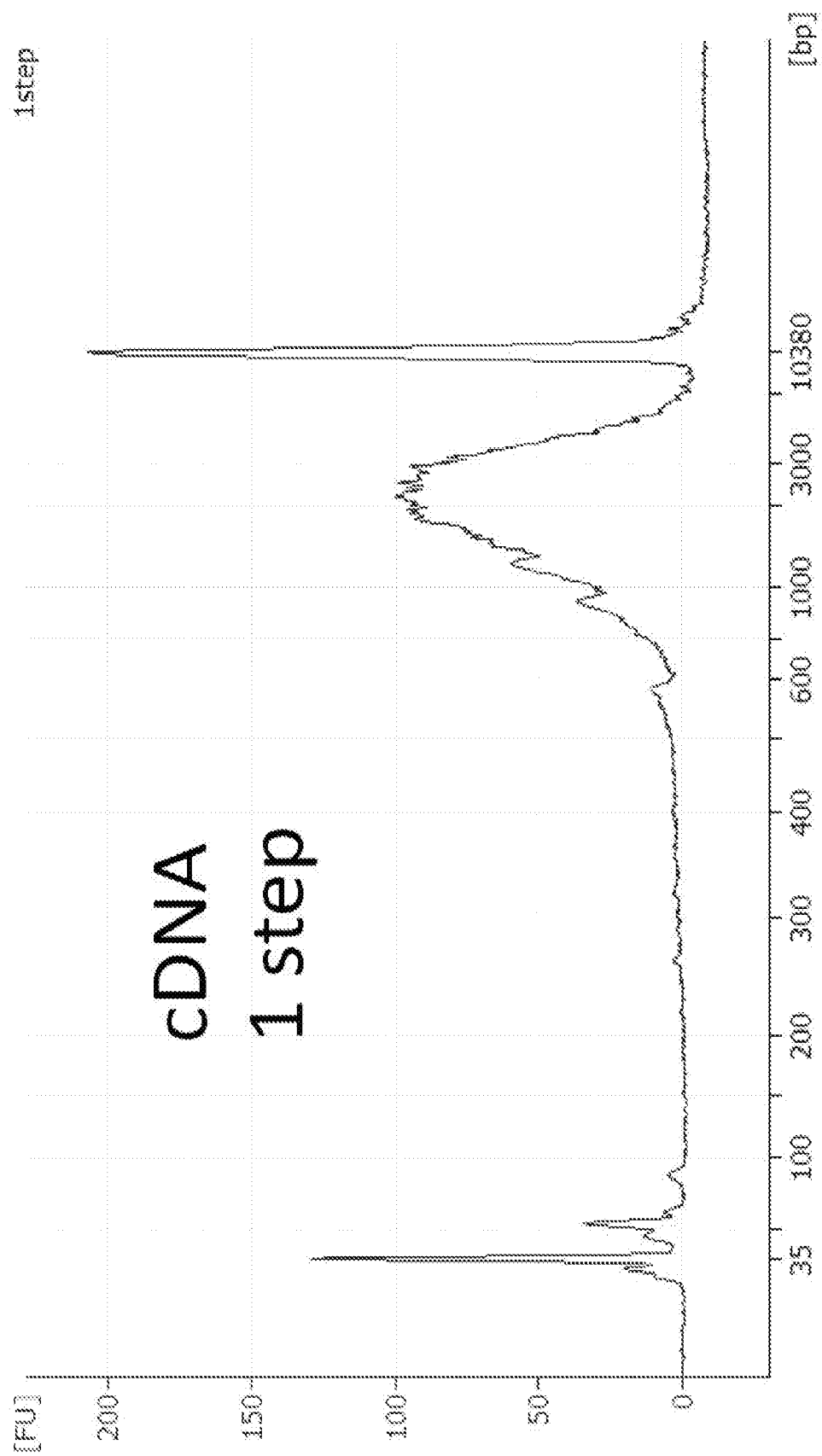
FIG. 14 provides the sequence length distribution of the amplified double-stranded cDNA product of a one-step RT-PCR protocol as described herein.

The sequence length distributions, in relative frequency units (FU) over a range of 35 to 10380 base pairs (bp), for the amplified double-stranded cDNA products of the Three Step (FIG. 12), Two Step (FIG. 13) and One Step (FIG. 14) protocols are provided. These results demonstrate that the shortened protocols do not demonstrate any deficiencies in the production of amplified double-stranded cDNA as compared to a more conventional three step protocol.

The amplified double-stranded cDNA product from each corresponding protocol (Three Step, Two Step and One Step) was further subjected to analysis by Bioanalyzer, CLC Bio bioinformatics, and Star aligner according to conventional methods. The results of these analyses are presented below in Table 4.

TABLE 4

Results:

| | | | 3 step | 2 step | 1 step |
|---|---|---|---|---|---|
| | RNA | | 10 pg Mouse Brain RNA/rxn | | |
| Bioanalyzer | cDNA | Average Size [bp] | 2,372 | 2,503 | 2,141 |
| | | Conc. [pg/μl] | 583.7 | 487 | 565.7 |
| | | Yield [ng] | 7 | 5.8 | 6.8 |
| CLC bio | Input reads | | 4 million paired-reads (2 × 75) | | |
| | Reference genome | | mm 10 | | |
| | Mapped to rRNA | | 0.75% | 1.57% | 2.37% |
| | Mapped to Mito | | 4.71% | 4.04% | 4.55% |
| | Mapped to genome | Exon | 81.6% | 78.8% | 77.2% |
| | | Intron | 14.3% | 16.6% | 17.9% |
| | | Intergenic | 4.1% | 4.6% | 4.9% |
| | FPKM (TE) | >0.1 | 12,996 | 13,704 | 13,821 |
| | | >1 | 10,995 | 11,697 | 11,575 |
| | Pearson correlation | 3 step | | 0.94 | 0.94 |
| | | 2 step | | | 0.95 |
| Star aligner | Mismatch rate | | 0.38% | 0.38% | 0.38% |

The Bioanalyzer analysis demonstrated that the amplified double-stranded cDNA product produced from the shortened protocols have size, concentration and yield characteristics similar to those of product cDNA produced using the longer 3 Step protocol. Furthermore, sequencing and alignment analysis showed that the amplified product cDNA produced in the shortened protocols performed at least as well as the product produced in the longer protocol.

Example 2: Template Switching onto a Bead

In certain reverse transcription methods, e.g., as performed in a droplet or microwell, a user may utilize a solid support, such as a single solid support or a plurality of supports, e.g., bead, to facilitate capture and barcoding of an RNA sample. Often, a bead is used having an attached oligo-dT or gene specific primer that hybridizes with mRNA generally or a specific RNA of interest. The procedure may be configured such that reverse transcription takes place such that template switching occurs onto a separate template switching oligonucleotide that is unbound, i.e., not attached to the solid support, e.g., bead.

Figure 15:
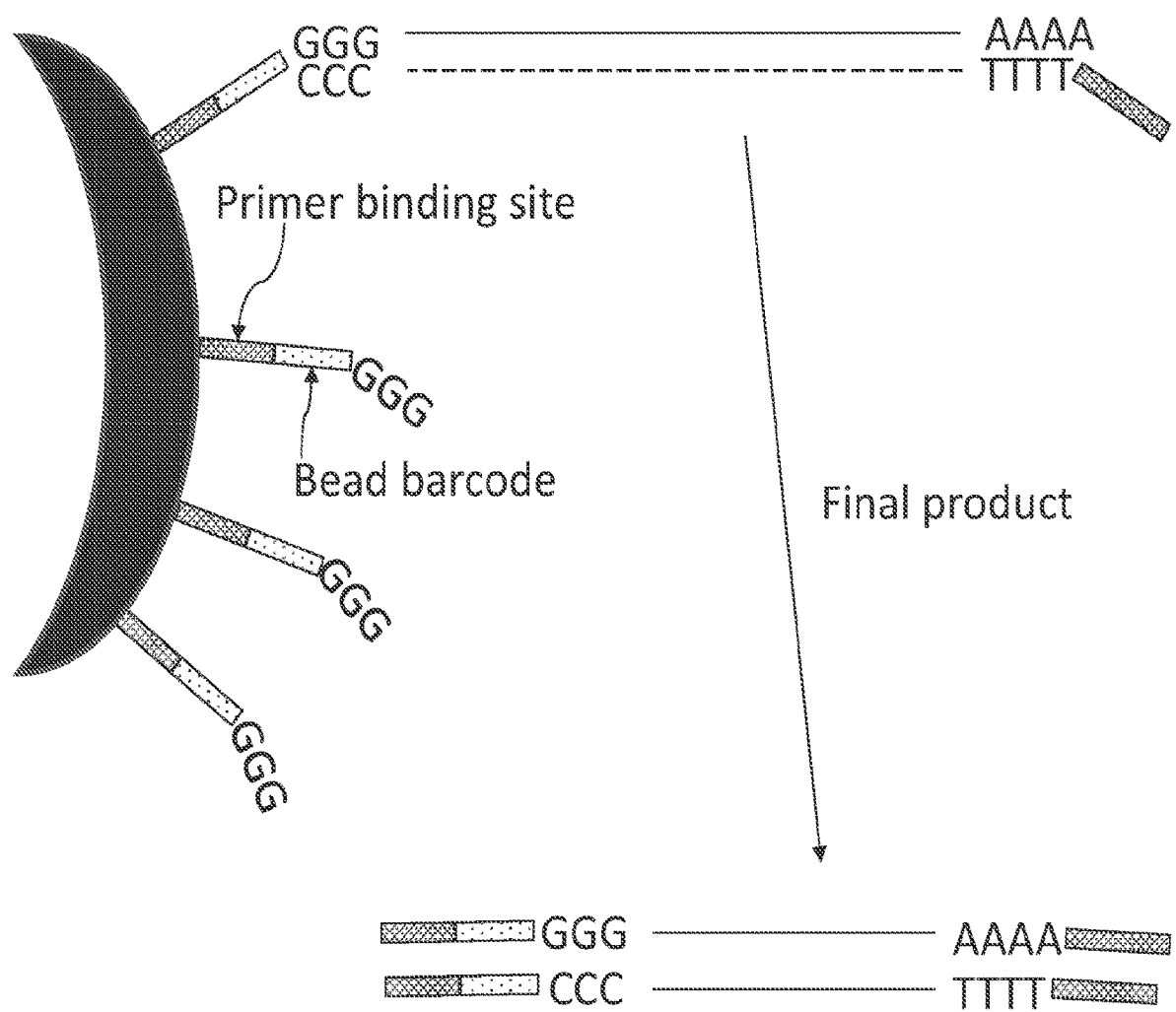
FIG. 15 provides a schematic representation of template switching onto a bead according to one embodiment of the present disclosure.

Presented here is a protocol where template switching occurs onto a bead performed using a template switch oligonucleotide that attached to the bead. For example, as presented in FIG. 15, a template switch oligonucleotide, having a primer binding site and a bead barcode, is attached to a bead. The template switch oligonucleotide includes a tri-nucleotide (GGG) at the end opposite the bead-attached end. The instant examples depicts the use of a poly-dT primer used to reverse transcribe from a poly-A containing mRNA which, upon completion of the reverse transcription, terminal transferase activity of the employed RT preferentially adds non-templated nucleotides that are complementary to the tri-nucleotides at the free end of the template switching oligonucleotide ("CCC" in this example as depicted in FIG. 15). After hybridization of the non-templated nucleotides to the tri-nucleotide end of the template switching oligonucleotide, template switching occurs leading to the addition of the bead barcode and primer binding site sequences to the reverse transcribed strand.

The reverse transcribed strand is then associated with the bead due to continued hybridization with the bead-bound template switching oligonucleotide. At this point, the bead may or may not be utilized for capture of reverse transcribed strand, e.g., by isolating and/or sorting the beads. Amplification, e.g., using a long or a shortened protocol as discussed above, may be employed to generate an amplified final product double stranded cDNA containing the bead barcode and primer binding site sequences of the bead-bound template switching oligonucleotide.

Example 3: Added PCR Primer is not Required for Amplification Following First Strand cDNA Synthesis when TSO and CDS Primers are Present This example demonstrates that the TSO and CDS oligos can act as PCR amplification primers. For this experiment, SMART-Seq v4 Ultra Low Input RNA Kit for Sequencing (Takara Bio USA, Inc.) was used as follows.

First-Strand cDNA Synthesis:
1. 10× Reaction Buffer was prepared by mixing 19 µl of 10× Lysis Buffer and 1 µl of RNase Inhibitor.
2. 1 µl of 10× Reaction Buffer, 1 µl of 3' SMART-Seq CDS Primer IIA, 2 µl of 5 µg/ul Mouse Brain RNA (MBR) and 8.5 µl of Nuclease-Free Water were mixed in 0.2 ml PCR tube.
3. The tube was incubated at 72° C. for 3 minutes and then placed on ice for 2 minutes.
4. 4 µl of 5× Ultra Low First-Strand Buffer, 1 µl of SMART-Seq v4 Oligonucleotide, 0.5 µl of RNase Inhibitor (40 U/µl) and 2 µl of SMARTScribe Reverse Transcriptase were added the tube (Total volume: 20 µl).
5. The tube was placed in a thermal cycler and the following program was run:
    a. 42° C. 90 min
    b. 70° C. 10 min
    c. 4° C. forever Optional Purification of First-Strand cDNA, where employed, was performed as follows:
1. 20 µl of AMPure XP beads were added to 2 tubes.
2. The tubes were mixed by vortexing and incubated at room temperature for 8 minutes.
3. The tubes were placed on a magnetic separation device for a few minutes and then the supernatants were discarded.
4. 200 µl of 80% ethanol was added to the tubes on a magnetic separation device and then carefully pipetted and discarded.
5. Step 4 was repeated once.
6. Once the beads were dried, the cDNAs were eluted into 20 µl of Elution Buffer.

Optional cDNA Amplification, where employed, was performed as follows:
1. 25 µl of 2× SeqAmp PCR Buffer, 1 µl of PCR Primer IIA, 1 µl of SeqAmp DNA Polymerase and 3 µl of Nuclease-Free water were added to first-strand cDNA (Total volume: 50 µl).
2. The tubes were placed in a thermal cycler and the following program was run:
    a. 95° C. 1 min
    b. 98° C. 10 sec
    c. 65° C. 30 sec
    d. 68° C. 3 min
    17 cycles for b.-d.
    e. 72° C. 10 min
    f. 4° C. forever Purification of Amplified cDNA:
1. 50 µl of AMPure XP beads were added to tubes.
2. The tubes were mixed by vortexing and incubated at room temperature for 8 minutes.
3. The tubes were placed on a magnetic separation device for a few minutes and then the supernatants were discarded.
4. 200 µl of 80% ethanol was added to the tubes on a magnetic separation device and then carefully pipetted and discarded.
5. Step 4 was repeated once.
6. Once the beads were dried, the cDNAs were eluted into 17 µl of Elution Buffer.

Figure 16:
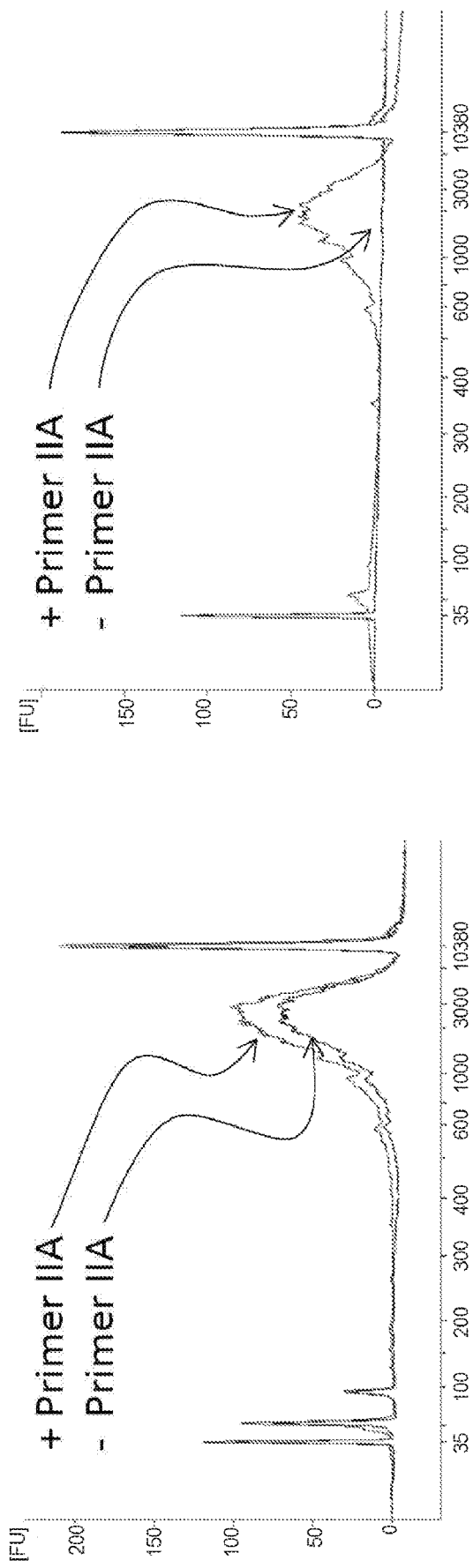
FIG. 16 demonstrates amplification, in the absence of PCR primers, using template switching oligonucleotide and first strand synthesis primer present following an RT reaction.

As shown in the FIG. 16, without the addition of PCR primers (primer IIA) and without purification of the first strand cDNA synthesis reaction (i.e., the RT reaction), a product was still detected having the appropriate size, e.g., as compared to positive control (FIG. 16, left, "+ Primer IIA"), as shown in the Bioanalyzer trace (FIG. 16, left, "—Primer IIA"). In contrast, when the first strand cDNA synthesis reaction was purified, removing the TSO and CDS oligos, no product was produced (FIG. 16, right, "– Primer IIA"), unless PCR primers were also added (FIG. 16, right, "+ Primer IIA"). These representative traces demonstrate that amplification can be performed in the presence of the TSO and CDS oligos even when PCR primers are not included in the reaction. However, when the TSO and CDS oligos are purified out of the reaction, the addition of the IIA amplification primer is necessary to generate an amplification product.

Table 5 below provides the quantification of these results. As shown in the far right column of Table 5, no cDNA product was formed after purification, removing the TSO and CDS oligos, when PCR primer IIA was not added. However, when purification was not performed after RT, leaving the TSO and CDS oligos in the reaction mixture, the amplification products generated in the presence (+) and absence (–) of PCR primer IIA were highly similar.

TABLE 5

| Purification after RT | | – | | + | |
|---|---|---|---|---|---|
| PCR primer IIA | | + | – | + | – |
| cDNA | Avg. Size [bp] | 2,362 | 2,509 | 2,041 | – |
| | Yield [ng] | 6.1 | 5.8 | 4.8 | – |
| rRNA | | 1.1% | 0.9% | 2.2% | |
| Mito | | 4.4% | 4.6% | 6.5% | |
| Genome | Total Exon | 82% | 82% | 81% | |
| | Intron | 14% | 14% | 15% | |
| | Intergenic | 4% | 4% | 4% | |
| # of transcript | >0.1 | 12,769 | 12,807 | 10,554 | |
| | >1 | 10,802 | 10,934 | 8,746 | |
| Pearson | | | 0.95 | 0.93 | |
| | | | | 0.93 | |
| Mismatch rate (STAR) | | 0.40% | 0.41% | 0.39% | |

This example demonstrates that PCR primer is not required for amplification following first strand cDNA synthesis when TSO and CDS primers are present in the reaction mixture. The provided results also show that the amplification product generated in the absence of the PCR primer is similar to the amplification product generated when PCR primer is added.

Figure 17:
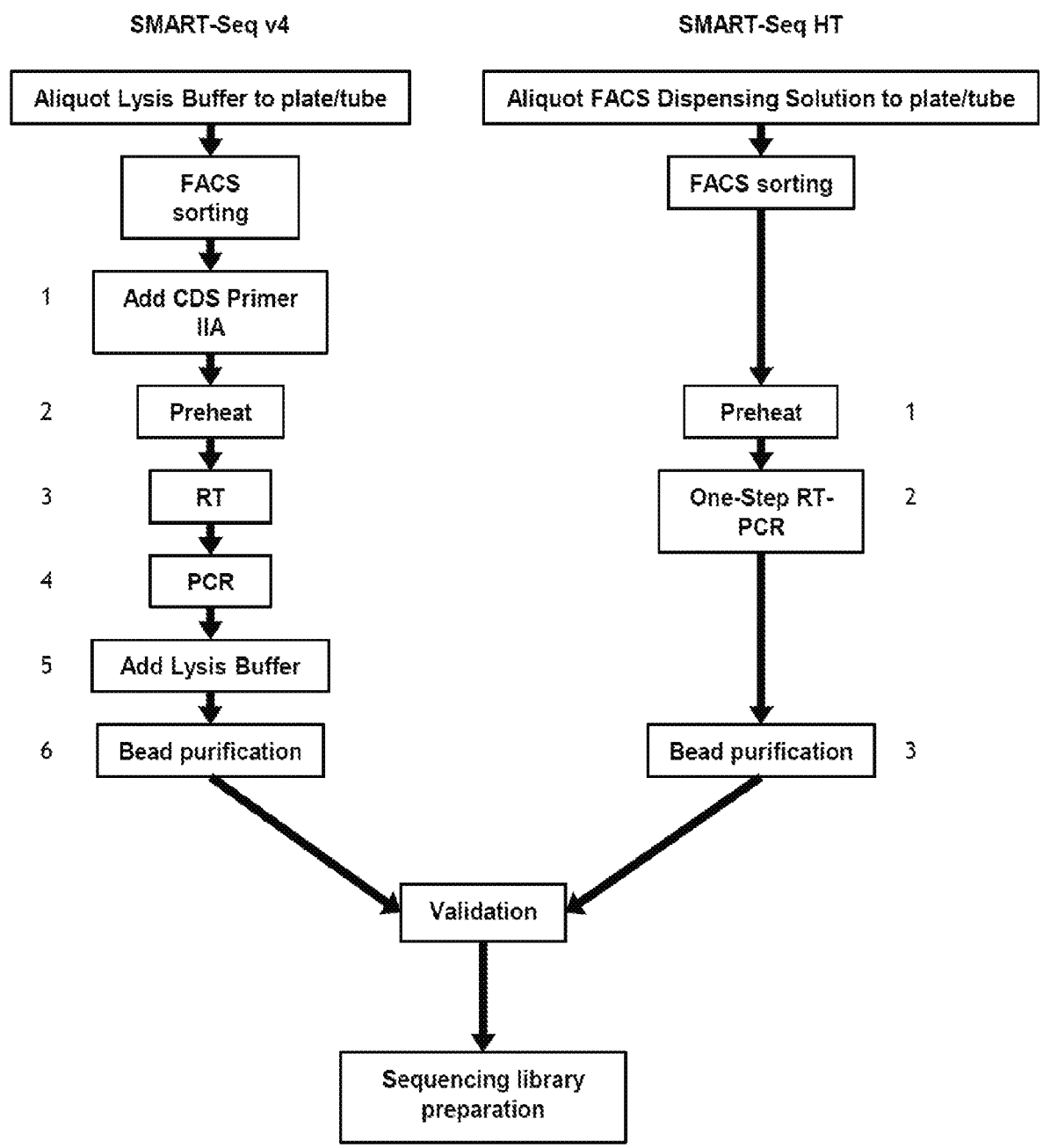
FIG. 17 provides a schematic comparison of SMART-Seq v4 and SMART-Seq HT kit workflows.

Example 4: Comparisons Between Workflows Employing Multi-Step and Single Step RT-PCR Procedures FIG. 17 provides a schematic comparison of the SMART-Seq v4 and SMART-Seq HT kit workflows for sequencing library preparation. The SMART-Seq v4 method (left) was modified to generate a simplified, high-throughput workflow (SMART-Seq HT, right) with minimal hands-on time. Much of the reduction in hands-on time in the SMART-Seq HT workflow is a result of the inclusion of the One-Step RT-PCR procedure, as can be seen in FIG. 17.

The example provided here shows a comparison between the different RTPCR methods of the disclosure. For this example, SMART-Seq v4 Ultra Low Input RNA Kit for Sequencing (Takara Bio USA, Inc.) was used.

3-Step Procedure
Preheat:
1. 10× Reaction Buffer was prepared by mixing 19 μl of 10× Lysis Buffer and 1 μl of RNase Inhibitor.
2. 1 μl of 10× Reaction Buffer, 1 μl of 3' SMART-Seq CDS Primer IIA, 2 μl of 5 μg/ul Mouse Brain RNA (MBR) and 8.5 μl of Nuclease-Free Water were mixed in 0.2 ml PCR tube.
3. The tube was incubated at 72° C. for 3 minutes and then placed on ice for 2 minutes.

First-Strand cDNA Synthesis:
1. 4 μl of 5× Ultra Low First-Strand Buffer, 1 μl of SMART-Seq v4 Oligonucleotide, 0.5 μl of RNase Inhibitor (40 U/μl) and 2 μl of SMARTScribe Reverse Transcriptase were added to the preheated-tube (Total volume: 20 μl).
2. The tube was placed in a thermal cycler and the following program was run:
   a. 42° C. 90 min
   b. 70° C. 10 min
   c. 4° C. forever cDNA Amplification:
1. 25 μl of 2× SeqAmp PCR Buffer, 1 μl of PCR Primer IIA, 1 μl of SeqAmp DNA Polymerase and 3 μl of Nuclease-Free water were added to first-strand cDNA (Total volume: 50 μl).
2. The tubes were placed in a thermal cycler and the following program was run:
   a. 95° C. 1 min
   b. 98° C. 10 sec
   c. 65° C. 30 sec
   d. 68° C. 3 min
   17 cycles for b.-d.
   e. 72° C. 10 min
   f. 4° C. forever 2-Step Procedure
Preheat:
1. 10× Reaction Buffer was prepared by mixing 19 μl of 10× Lysis Buffer and 1 μl of RNase Inhibitor.
2. 1 μl of 10× Reaction Buffer, 1 μl of 3' SMART-Seq CDS Primer IIA, 2 μl of 5 μg/ul Mouse Brain RNA (MBR) and 8.5 μl of Nuclease-Free Water were mixed in 0.2 ml PCR tube.
3. The tube was incubated at 72° C. for 3 minutes and then placed on ice for 2 minutes.

First-Strand cDNA Synthesis Reaction (and the Applied Amplification in a Program):
1. 4 μl of 5× Ultra Low First-Strand Buffer, 1 μl of SMART-Seq v4 Oligonucleotide, 0.5 μl of RNase Inhibitor (40 U/μl), 2 μl of SMARTScribe Reverse Transcriptase, 4 μl of 2× SeqAmp PCR Buffer and 1 μl of SeqAmp DNA Polymerase were added the tube (Total volume: 25 μl).
   a. 42° C. 90 min
   b. 95° C. 1 min
   c. 98° C. 10 sec
   d. 65° C. 30 sec
   e. 68° C. 3 min
   17 cycles for c.-e.
   f. 72° C. 10 min
   g. 4° C. forever 1-Step Procedure
First-Strand cDNA Synthesis (and the Applied Amplification in a Program) with or without a Preheat Step:
1. 10× Reaction Buffer was prepared by mixing 19 μl of 10× Lysis Buffer and 1 μl of RNase Inhibitor.
2. 1 μl of 10× Reaction Buffer, 1 μl of 3' SMART-Seq CDS Primer IIA, 2 μl of 5 μg/ul Mouse Brain RNA (MBR) and 8.5 μl of Nuclease-Free Water were mixed in 0.2 ml PCR tube.
3. 4 μl of 5× Ultra Low First-Strand Buffer, 1 μl of SMART-Seq v4 Oligonucleotide, 0.5 μl of RNase Inhibitor (40 U/μl), 2 μl of SMARTScribe Reverse Transcriptase, 4 μl of 2× SeqAmp PCR Buffer and 1 μl of SeqAmp DNA Polymerase were added the tube (Total volume: 25 μl).
   a. 50° C., 60° C. or 70° C. 1 min or no preheat
   b. 42° C. 90 min
   c. 95° C. 1 min
   d. 98° C. 10 sec
   e. 65° C. 30 sec
   f. 68° C. 3 min
   17 cycles for d.-f.
   g. 72° C. 10 min
   h. 4° C. forever Purification of Amplified cDNA:
1. 50 μl (3-step) or 25 μl (2-step & 1-step) of AMPure XP beads were added to tubes.
2. The tubes were mixed by vortexing and incubated at room temperature for 8 minutes.
3. The tubes were placed on a magnetic separation device for a few minutes and then the supernatants were discarded.
4. 200 μl of 80% ethanol was added to the tubes on a magnetic separation device and then carefully pipetted and discarded.
5. Step 4 was repeated once.
6. Once the beads were dried, the cDNAs were eluted into 17 μl of Elution Buffer.

As shown in Table 6, the 3-step, 2-step, 1-step without a preheat treatment, and 1-step RTPCR with a preheat treatment at 50° C. all showed comparable numbers of transcripts identified, minimal rRNA, high Pearson correlations, and high mapping percentages. The 1-step RTPCR protocols with preheat treatment at 60° C. and 70° C., and 60° C. with cold shock on ice all yielded no results in this example. The 1-step protocol at 50° C. with cold shock on ice did yield a product (as shown), but this product was not sequenced ("NS"). These results demonstrate that 3-step, 2-step and 1-step (without preheating or with preheating at 50° C.) procedures all generate comparable product nucleic acid.

TABLE 6

|  |  | 3step | 2step | 1step NoHeat | 1step 50 C. | 1step 60 C. | 1step 70 C. | 1step 50 C. + on ice | 1step 60 C. + on ice |
|---|---|---|---|---|---|---|---|---|---|
| cDNA | Avg. size [bp] | 2,372 | 2,503 | 2,141 | 1,942 | — | — | 1,859 | — |
|  | Yield [ng] | 7 | 5.8 | 6.8 | 5 | — | — | 5 | — |
| rRNA |  | 0.8% | 1.6% | 2.4% | 1.0% |  |  | NS |  |
| Mito |  | 4.7% | 4.0% | 4.6% | 5.2% |  |  | NS |  |
| Genome | Exon | 82% | 79% | 77% | 78% |  |  | NS |  |
|  | Intron | 14% | 17% | 18% | 17% |  |  | NS |  |
|  | Intergenic | 4% | 5% | 5% | 5% |  |  | NS |  |
| # of transcript | >0.1 | 12,996 | 13,704 | 13,821 | 13,049 |  |  | NS |  |
|  | >1 | 10,995 | 11,697 | 11,575 | 11,017 |  |  | NS |  |
| Pearson | 3step |  | 0.94 | 0.94 | 0.93 |  |  | NS |  |
|  | 2step |  |  | 0.95 | 0.94 |  |  | NS |  |
|  | 1step NoHeat |  |  |  | 0.96 |  |  | NS |  |
| Mismatch rate (STAR) |  | 0.38% | 0.38% | 0.38% | 0.36% |  |  | NS |  |

The product nucleic acids generated using 3-step, 2-step and 1-step procedures were further analyzed for gene body coverage and bioanalyzer sample characteristics. The results of this further analysis are provided in FIG. 18. As can be seen in FIG. 18 (top), gene body coverage (showing 3-step, 2-step, 1-step no heat, and 1-step 50° C.) was similar across all methods which indicates comparably minimal biases between the methods. The bioanalyzer traces (FIG. 18, bottom) show that, in this example, all methods except for the 1-step RTPCR at 60° C., produced appropriate sized libraries.

Further analysis was performed to compare the sensitivity and mappability between SMART-Seq v4 and SMART-Seq HT kits. Specifically, replicate cDNA libraries were generated from 10 µg Mouse Brain Total RNA using the SMART-Seq v4 or the SMART-Seq HT kits. RNA-seq libraries were generated from output cDNA using the Nextera XT DNA Library Preparation Kit and sequenced on an Illumina NextSeq instrument (2×75 bp). Sequences were analyzed after normalizing all the samples to 13 million paired-end reads. The two kits generated similar sequencing metrics, as shown in FIG. 19, with a high mapping rate and comparable number of transcripts identified, in addition to strong Pearson and Spearman correlations. These data indicate that the SMART-Seq HT Kit provides the same sensitivity and reproducibility as the SMART-Seq v4 kit.

Figure 20:
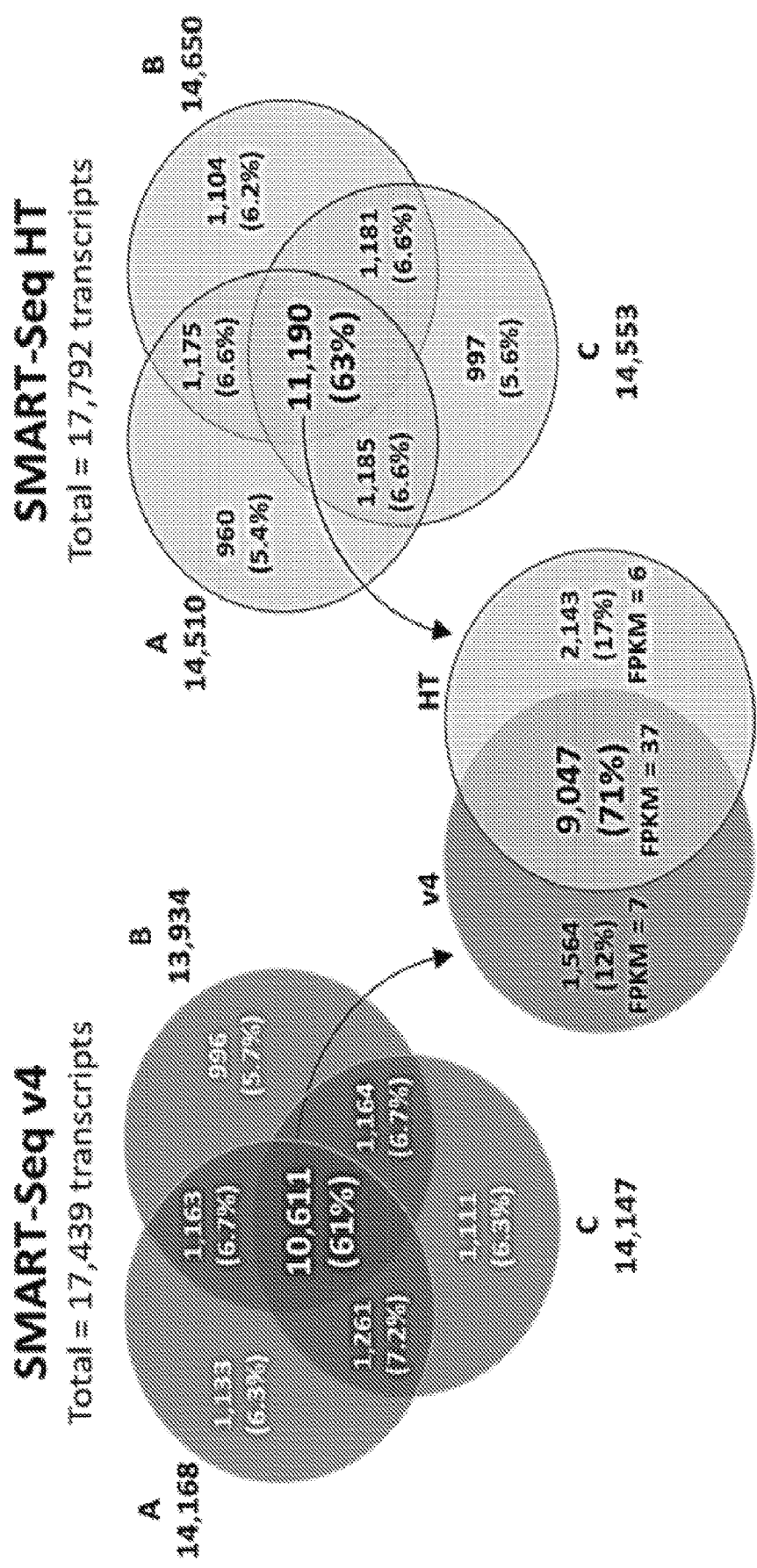
FIG. 20 demonstrates a high correlation in number of transcripts identified for data generated with the SMART-Seq v4 and SMART-Seq HT kits.

Further analysis was performed to compare the number of transcripts identified for data generated with the SMART-Seq v4 and SMART-Seq HT kits. Specifically, libraries prepared from 10 µg of Mouse Brain Total RNA (as above) were further evaluated for the overlap in the number of transcripts identified (Fragments Per Kilobase of transcript per Million mapped reads, FPKM >0.1) between technical replicates within each kit. As shown in FIG. 20, These results were found to be very similar (61-63% overlap). Transcripts identified by all three replicates for each kit were then compared against each other, indicating an overlap of 71% (see FIG. 20). The overlapping transcripts had an average expression level of 37 FPKM, while the transcripts uniquely identified with individual kits are less abundant, averaging between 6-7 FPKM, indicating that the transcripts more likely to not be identified are those expressed at low levels. This analysis demonstrated a high correlation in number of transcripts identified for data generated with the SMART-Seq v4 and SMART-Seq HT kits.

Further analysis was performed to evaluate gene GC content representation for the SMART-Seq v4 and SMART-Seq HT kits. Specifically, the libraries made from 10 µg of Mouse Brain Total RNA (as above) were further analyzed for GC content representation. Genes were binned by GC content, and the number of genes identified is reported for each bin in FIG. 21 (numbers shown are the average of three technical replicates). As can be seen in the provided data, the percentages of genes identified in each bin were identical for the two kits. For reference, there are 35,495 annotated RefSeq genes, of which 4.7% are arbitrarily classified as low CG content (≤36%), 89.9% are classified as medium CG content (37-54%), and 5.4% are classified as high GC content (≥55%). This analysis demonstrates that there is no GC content representation bias in the reduced-step method as compared to the 3 step method.

Figure 22:
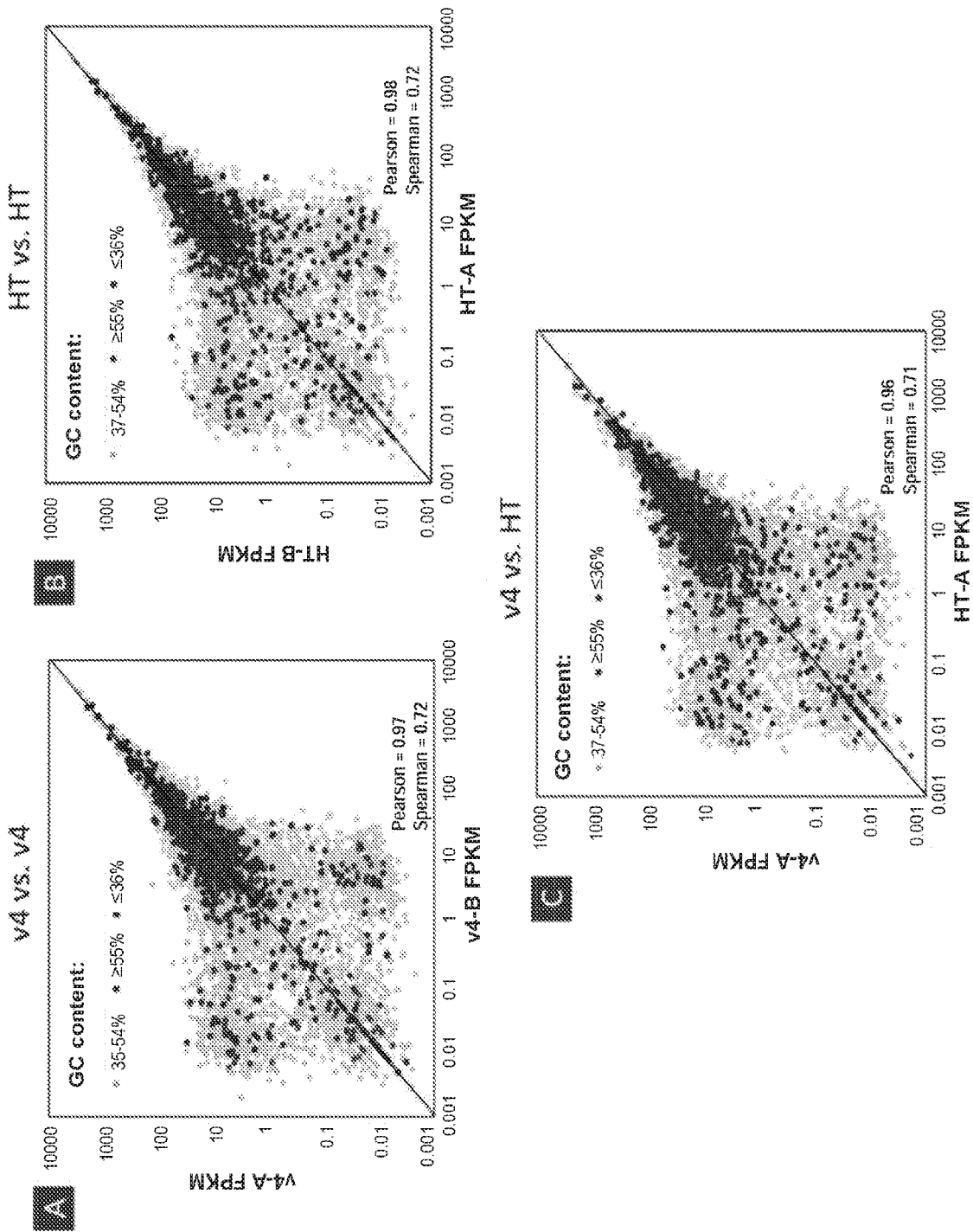
FIG. 22 shows that the one-Step RT-PCR reaction maintains the representation of low- and high-GC content genes.

Further analysis was performed to compare expression level by gene GC content between the SMART-Seq v4 and SMART-Seq HT kits. The libraries made from 10 µg of Mouse Brain Total RNA shown (as above) were further analyzed for GC content representation (see FIG. 21). Genes were binned by GC content, and correlation plots were used to visualize the reproducibility of the expression levels (FPKM) of gene in each bin (FIG. 22). The average gene counts are very reproducible for replicate samples analyzed using the SMART-Seq v4 (Panel A) or SMART-Seq HT kits (Panel B). Genes with high or low GC content show similar expression levels in the SMART-Seq v4 and SMART-Seq HT kits (Panel C). Thus, this analysis shows that the One-Step RT-PCR reaction introduced in the new SMART-seq HT Kit maintains the representation of the low- and high-GC content genes.

Further analysis was performed to compare sequencing library generation from 293T cells using SMART-Seq v4 or SMART-Seq HT kits. Specifically, libraries were generated from individual 293T cells isolated by FACS using the SMART-Seq v4 or the SMART-Seq HT kits.

For FACS sorting, 293T cells grown to near confluence were harvested by trypsinization, stained with FITC Mouse anti-Human CD47 (Clone B6H12; BD, Cat No. 556045), and resuspended in ice-cold BD FACS Pre-Sort Buffer (BD, Cat No. 563503). Sorting was done with a BD FACSJazz® Cell Sorter in 12.5 µl of FACS Dispensing Solution Cells were frozen at −80° C. until ready for processing. The cDNA was synthesized and sequencing libraries prepared and sequenced. Reads from all libraries were trimmed and mapped to mammalian rRNA and the human or mouse mitochondrial genomes using CLC Genomics Workbench. The remaining reads were subsequently mapped using CLC to the human (hg19) or mouse (mm10) genome with RefSeq annotation. All percentages shown related to these analyses, including the number of reads that map to introns, exons, or intergenic regions, are percentages of the total reads in the library. The number of transcripts identified in each library was determined by the number of transcripts with an FPKM greater than or equal to 1 or 0.1.

RNA-seq libraries were generated using the Nextera XT DNA Library Preparation Kit and sequenced on an Illumina NextSeq instrument (2×75 bp). Sequences were analyzed after normalizing all the samples to 7 million paired-end reads. As can be seen in the results provided in FIG. 23, the two kits generated similar sequencing metrics, with a high mapping rate and around 600 additional transcripts identified in the SMART-Seq HT Kit. These data indicate that the SMART-Seq HT Kit provides the same or slightly higher sensitivity as compared to the SMART-Seq v4 kit.

Figure 24:
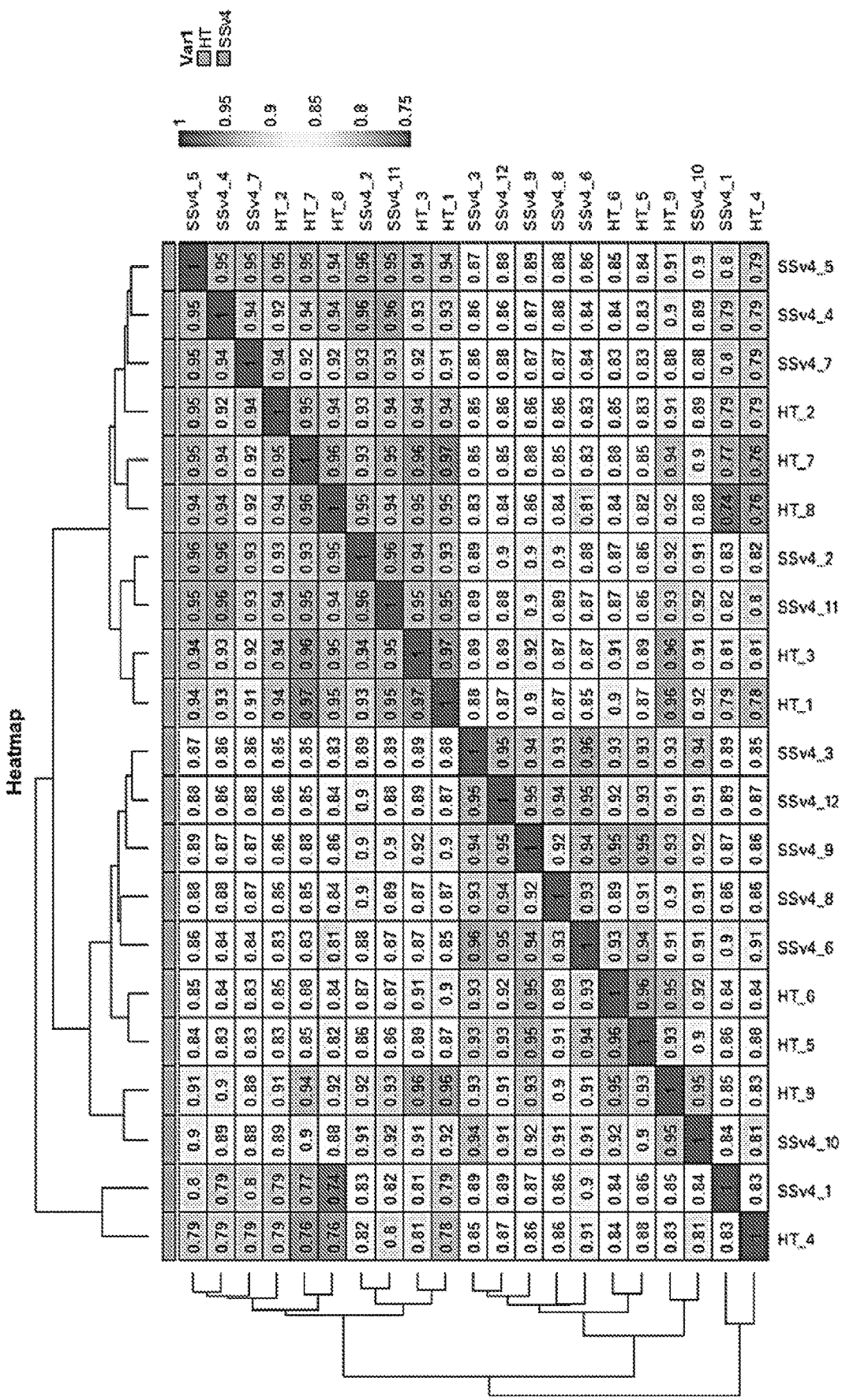
FIG. 24 demonstrates that the reduced-step workflow in the SMART-Seq HT Kit does not introduce any major bias in measurement of gene expression levels.

Further analysis was performed to compare the reproducibility of gene expression data obtained from FACS-sorted 293T cells using the SMART-seq v4 and SMART-Seq HT kits. Specifically, libraries generated from twenty-one individual 293T cells (see FIG. 23) were further analyzed to evaluate the reproducibility of gene expression measurements obtained for each cell with the SMART-Seq v4 kit (55v4_1 to 55v4_12) and the SMART-Seq HT Kit (HT_1 to HT_9). FIG. 24 provides a hierarchical clustering heat map showing the Euclidean distances between all the cells and reports Pearson correlations ranging from 0.74 to 0.97. These data show that the correlations are very high between the two kits and that the cells did not cluster based on the library preparation method. These data further demonstrate that the modified workflow in the SMART-Seq HT Kit does not introduce major bias in measurement of gene expression levels. Overall this analysis demonstrates the high reproducibility of gene expression data obtained from FACS-sorted 293T cells using the SMART-seq v4 and SMART-Seq HT kits.

Notwithstanding the appended claims, the disclosure is also defined by the following clauses:

1. A method of producing an amplified double stranded deoxyribonucleic acid (dsDNA) from a nucleic acid sample, the method comprising:
   (a) combining:
      a nucleic acid sample;
      a reverse transcriptase;
      a single product nucleic acid primer;
      a template switch oligonucleotide comprising a 3' hybridization domain;
      an amplification polymerase; and
      deoxyribonucleotide triphosphates (dNTPs);
   in a reaction mixture under conditions sufficient to produce a double stranded nucleic acid complex comprising a template nucleic acid and the template switch oligonucleotide hybridized to adjacent regions of a single product nucleic acid; and
   (b) amplifying from the single product nucleic acid using the template switch oligonucleotide and the single product nucleic acid primer under conditions sufficient to produce an amplified dsDNA.
2. The method according to Clause 1, wherein the 3' hybridization domain hybridizes to a non-templated sequence added to the single product nucleic acid by the reverse transcriptase.
3. The method according to Clause 2, wherein the non-templated sequence comprises a hetero-polynucleotide.
4. The method according to Clause 3, wherein the hetero-polynucleotide comprises a hetero-trinucleotide.
5. The method according to Clause 2, wherein the non-templated sequence comprises a homo-polynucleotide.
6. The method according to Clause 5, wherein the homo-polynucleotide comprises a homo-trinucleotide.
7. The method according to any of the preceding clauses, wherein the reverse transcriptase is a retroviral reverse transcriptase.
8. The method according to Clause 7, wherein the retroviral reverse transcriptase is a murine leukemia virus reverse transcriptase.
9. The method according to any of the preceding clauses, wherein the amplification polymerase is a hot-start polymerase.
10. The method according to any of the preceding clauses, wherein the amplification polymerase is a thermostable polymerase.
11. The method according to any of the preceding clauses, wherein the single product nucleic acid primer comprises a '5-non-tem plated sequence.
12. The method according to Clause 11, wherein the 5'-non-templated sequence is from 10 nt to 100 nt in length.
13. The method according to Clause 11 or 12, wherein the '5-non-templated sequence comprises a restriction endonuclease recognition site.
14. The method according to any of Clauses 11-13, wherein the '5-non-templated sequence comprises a primer binding site.
15. The method according to any of Clauses 11-14, wherein the '5-non-templated sequence comprises a defined sequence.
16. The method according to any of Clauses 11-15, wherein the '5-non-templated sequence comprises a source barcode sequence.
17. The method according to Clause 16, wherein the source barcode sequence comprises a sample barcode sequence.
18. The method according to Clauses 16 or 17, wherein the source barcode sequence comprises a well barcode sequence.
19. The method according to any of Clauses 16-18, wherein the source barcode sequence comprises a cell barcode sequence.
20. The method according to any of Clauses 11-19, wherein the '5-non-templated sequence comprises a unique molecular identifier sequence (UMI).
21. The method according to any of Clauses 11-20, wherein the '5-non-templated sequence comprises a unique molecular identifier (UMI) domain.
22. The method according to any of Clauses 11-21, wherein the '5-non-templated sequence comprises a barcoded unique molecular identifier (BUMI) domain.
23. The method according to any of Clauses 11-21, wherein the '5-non-templated sequence comprises a sequencing platform adapter construct.
24. The method according to any of the preceding clauses, wherein the single product nucleic acid primer comprises a caged capture moiety that is integrated into the amplified dsDNA during the amplifying.
25. The method according to Clause 24, wherein the method further comprises uncaging the caged capture moiety to attach the amplified dsDNA to a solid support.
26. The method according to Clause 25, wherein the method further comprises collecting the solid support to isolate the amplified dsDNA.

27. The method according to any of the preceding clauses, wherein the template switch oligonucleotide comprises a 5'-non-templated sequence.
28. The method according to Clause 27, wherein the 5'-non-templated sequence is from 10 nt to 100 nt in length.
29. The method according to Clause 27 or 28, wherein the 5'-non-templated sequence comprises a restriction endonuclease recognition site.
30. The method according to any of Clauses 27-29, wherein the '5-non-templated sequence comprises a primer binding site.
31. The method according to any of Clauses 27-30, wherein the '5-non-templated sequence comprises a defined sequence.
32. The method according to any of Clauses 27-31, wherein the '5-non-templated sequence comprises a source barcode sequence.
33. The method according to Clause 32, wherein the source barcode sequence comprises a sample barcode sequence.
34. The method according to Clauses 32 or 33, wherein the source barcode sequence comprises a well barcode sequence.
35. The method according to any of Clauses 32-34, wherein the source barcode sequence comprises a cell barcode sequence.
36. The method according to any of Clauses 27-35, wherein the '5-non-templated sequence comprises a unique molecular identifier sequence (UMI).
37. The method according to any of Clauses 27-36, wherein the '5-non-templated sequence comprises a unique molecular identifier (UMI) domain.
38. The method according to any of Clauses 27-37, wherein the '5-non-templated sequence comprises a barcoded unique molecular identifier (BUMI) domain.
39. The method according to any of Clauses 27-38, wherein the '5-non-templated sequence comprises a sequencing platform adapter construct.
40. The method according to any of the preceding clauses, wherein the template switch oligonucleotide comprises a caged capture moiety that is integrated into the amplified dsDNA during the amplifying.
41. The method according to Clause 40, wherein the method further comprises uncaging the caged capture moiety to attach the amplified dsDNA to a solid support.
42. The method according to Clause 41, wherein the method further comprises collecting the solid support to isolate the amplified dsDNA.
43. The method according to any of Clauses 11-42, wherein the single product nucleic acid primer and template switch oligonucleotide both comprise a 5'-non-templated sequence.
44. The method according to Clause 43, wherein the single product nucleic acid primer and template switch oligonucleotide comprise the same 5'-non-templated sequence.
45. The method according to Clause 43, wherein the single product nucleic acid primer and template switch oligonucleotide comprise different 5'-non-templated sequences.
46. The method according to any of the preceding clauses, wherein the single product nucleic acid primer is attached to a solid support.
47. The method according to any of the preceding clauses, wherein the template switch oligonucleotide is attached to a solid support.
48. The method according to any of the preceding clauses, wherein the amplifying comprises suppression PCR.
49. The method according to any of the preceding clauses, wherein the amplifying comprises quantitative PCR.
50. The method according to any of the preceding clauses, wherein the amplifying comprises emulsion PCR.
51. The method according to any of the preceding clauses, wherein the method further comprises denaturing the template nucleic acid prior to the transcribing.
52. The method according to any of the preceding clauses, wherein the method further comprises purifying the amplified dsDNA after the amplifying.
53. The method according to any of the preceding clauses, wherein the single product nucleic acid is not purified between the combining and the amplifying.
54. The method according to any of the preceding clauses, wherein the method is performed in a reaction vessel.
55. The method according to Clause 54, wherein the reaction vessel is a tube.
56. The method according to Clause 54, wherein the reaction vessel is a well of a multi-well plate.
57. The method according to any of Clauses 1-53, wherein the method is performed in a droplet.
58. The method according to any of the preceding clauses, wherein the reaction mixture comprises a nucleic acid detection reagent.
59. The method according to Clause 58, wherein the method further comprises detecting the presence of the amplified dsDNA based on the nucleic acid detection reagent.
60. The method according to Clause 59, wherein the method is performed in a droplet and further comprises sorting the droplet based on the detecting.
61. The method according to Clause 60, wherein the sorting is performed using a fluorescence based droplet sorter.
62. The method according to Clause 61, wherein the fluorescence based droplet sorter is a flow cytometer.
63. The method according to Clause 61, wherein the fluorescence based droplet sorter is a microfluidic-based droplet sorter.
64. The method according to any of the preceding clauses, wherein the method further comprises hybridizing a labeled probe to the amplified dsDNA.
65. The method according to Clause 64, wherein the labeled probe is complementary to a target sequence and, when hybridized to the amplified dsDNA, indicates the presence of the target sequence in the amplified dsDNA.
66. The method according to Clause 65, wherein the method further comprises detecting the presence of the target sequence.
67. The method according to Clause 66, wherein the method is performed in a droplet and further comprises sorting the droplet based on the detecting.
68. The method according to Clause 67, wherein the sorting is performed using a fluorescence based droplet sorter.
69. The method according to Clause 68, wherein the fluorescence based droplet sorter is a flow cytometer.
70. The method according to Clause 68, wherein the fluorescence based droplet sorter is a microfluidic-based droplet sorter.

71. The method according to any of the preceding clauses, wherein the single product nucleic acid primer comprises a random sequence.
72. The method according to Clause 71, wherein the random sequence is a random hexamer sequence.
73. The method according to any of the preceding clauses, wherein the template nucleic acid comprises a tail sequence.
74. The method according to Clause 73, wherein the tail sequence comprises a poly(A) sequence.
75. The method according to Clause 73, wherein the tail sequence comprises a poly(T) sequence.
76. The method according to any of Clauses 73-75, wherein the method further comprises a tailing reaction which adds the tail sequence to the template nucleic acid.
77. The method according to any of Clauses 73-76, wherein the single product nucleic acid primer comprises a sequence complementary to the tail sequence.
78. The method according to Clause 77, wherein the sequence complementary to the tail sequence comprises an poly(dT) sequence.
79. The method according to Clause 77, wherein the sequence complementary to the tail sequence comprises an poly(dA) sequence.
80. The method according to any of the preceding clauses wherein the template nucleic acid comprises a deoxyribonucleic acid (DNA).
81. The method according to Clause 80, wherein the DNA is genomic DNA.
82. The method according to any of Clauses 1-79, wherein the template nucleic acid comprises a ribonucleic acid (RNA).
83. The method according to Clause 82, wherein the RNA is messenger RNA (mRNA).
84. The method according to Clause 82 or 83, wherein the single product nucleic acid primer is a first strand complementary DNA (cDNA) primer and the dsDNA is a double stranded cDNA.
85. A kit comprising:
    a single product nucleic acid primer;
    a template switch oligonucleotide comprising a 3' hybridization domain; and
    a polymerase cocktail comprising an amplification polymerase and a reverse transcriptase.
86. The kit according to Clause 85, wherein the single product nucleic acid primer and the template switch oligonucleotide are in separate vessels.
87. The kit according to Clause 85, wherein the single product nucleic acid primer and the template switch oligonucleotide are in the same vessel.
88. The kit according to Clause 87, wherein the single product nucleic acid primer, the template switch oligonucleotide and the polymerase cocktail are in the same vessel.
89. The kit according to any of Clauses 85-88, wherein the amplification polymerase is a hot-start polymerase.
90. The kit according to any of Clauses 85-89, wherein the amplification polymerase is a thermostable polymerase.
91. The kit according to any of Clauses 85-90, wherein the reverse transcriptase is a retroviral reverse transcriptase.
92. The kit according to Clause 91, wherein the retroviral reverse transcriptase is a murine leukemia virus reverse transcriptase.
93. The kit according to any of Clauses 85-92, wherein the 3' hybridization domain hybridizes to a non-templated sequence added to a single product nucleic acid by the reverse transcriptase.
94. The kit according to Clause 93, wherein the non-templated sequence comprises a hetero-polynucleotide.
95. The kit according to Clause 94, wherein the hetero-polynucleotide comprises a hetero-trinucleotide.
96. The kit according to any of Clauses 85-93, wherein the non-templated sequence comprises a homo-polynucleotide.
97. The kit according to Clause 96, wherein the homo-polynucleotide comprises a homo-trinucleotide.
98. The kit according to any of Clauses 85-97, wherein the single product nucleic acid primer comprises a '5-non-tem plated sequence.
99. The kit according to Clause 98, wherein the 5'-non-templated sequence is from 10 nt to 100 nt in length.
100. The kit according to Clauses 98 or 99, wherein the '5-non-templated sequence comprises a restriction endonuclease recognition site.
101. The kit according to any of Clauses 98-100, wherein the '5-non-templated sequence comprises a primer binding site.
102. The kit according to any of Clauses 98-101, wherein the '5-non-templated sequence comprises a defined sequence.
103. The kit according to any of Clauses 98-102, wherein the '5-non-templated sequence comprises a source barcode sequence.
104. The kit according to Clause 103, wherein the source barcode sequence comprises a sample barcode sequence.
105. The kit according to Clauses 103 or 104, wherein the source barcode sequence comprises a well barcode sequence.
106. The kit according to any of Clauses 103-105, wherein the source barcode sequence comprises a cell barcode sequence.
107. The kit according to any of Clauses 98-106, wherein the '5-non-templated sequence comprises a unique molecular identifier sequence (UMI).
108. The kit according to any of Clauses 98-107, wherein the '5-non-templated sequence comprises a unique molecular identifier (UMI) domain.
109. The kit according to any of Clauses 98-108, wherein the '5-non-templated sequence comprises a barcoded unique molecular identifier (BUMI) domain.
110. The kit according to any of Clauses 98-109, wherein the '5-non-tem plated sequence comprises a sequencing platform adapter construct.
111. The kit according to any of Clauses 85-110, wherein the single product nucleic acid primer comprises a caged capture moiety.
112. The kit according to any of Clauses 85-111, wherein the template switch oligonucleotide comprises a 5'-non-templated sequence.
113. The kit according to Clause 112, wherein the 5'-non-templated sequence is from 10 nt to 100 nt in length.
114. The kit according to Clauses 112 or 113, wherein the 5'-non-templated sequence comprises a restriction endonuclease recognition site.
115. The kit according to any of Clauses 112-114, wherein the '5-non-templated sequence comprises a primer binding site.

116. The kit according to any of Clauses 112-115, wherein the '5-non-templated sequence comprises a defined sequence.
117. The kit according to any of Clauses 112-116, wherein the '5-non-templated sequence comprises a source barcode sequence.
118. The kit according to Clause 117, wherein the source barcode sequence comprises a sample barcode sequence.
119. The kit according to Clauses 117 or 118, wherein the source barcode sequence comprises a well barcode sequence.
120. The kit according to any of Clauses 117-119, wherein the source barcode sequence comprises a cell barcode sequence.
121. The kit according to any of Clauses 114-120, wherein the '5-non-templated sequence comprises a unique molecular identifier sequence (UMI).
122. The kit according to any of Clauses 114-121, wherein the '5-non-templated sequence comprises a unique molecular identifier (UMI) domain.
123. The kit according to any of Clauses 114-122, wherein the '5-non-templated sequence comprises a barcoded unique molecular identifier (BUMI) domain.
124. The kit according to any of Clauses 114-123, wherein the '5-non-templated sequence comprises a sequencing platform adapter construct.
125. The kit according to any of Clauses 85-124, wherein the template switch oligonucleotide comprises a caged capture moiety.
126. The kit according to any of Clauses 98-125, wherein the single product nucleic acid primer and the template switch oligonucleotide both comprise a 5'-non-templated sequence.
127. The kit according to Clause 126, wherein the single product nucleic acid primer and the template switch oligonucleotide comprise the same 5'-non-templated sequence.
128. The kit according to Clause 127, wherein the single product nucleic acid primer and the template switch oligonucleotide comprise different 5'-non-templated sequences.
129. The kit according to any of Clauses 85-128, wherein the single product nucleic acid primer is attached to a solid support.
130. The kit according to any of Clauses 85-129, wherein the template switch oligonucleotide is attached to a solid support.
131. The kit according to any of Clauses 85-130, wherein the kit further comprises a nucleic acid detection reagent.
132. The kit according to any of Clauses 85-131, wherein the kit further comprises a labeled probe.
133. The kit according to any of Clause 85-132, wherein the kit further comprises dNTPs.
134. The kit according to any of Clauses 85-133, wherein the single product nucleic acid primer comprises an poly(dT) sequence.
135. The kit according to any of Clauses 85-134, wherein the single product nucleic acid primer comprises an poly(dA) sequence.
136. The kit according to any of Clauses 85-135, wherein the single product nucleic acid primer comprises a random sequence.
137. The kit according to Clause 136, wherein the random sequence is a random hexamer sequence.
138. The kit according to any of Clauses 85-137, wherein the kit further includes one or more reagents for performing a tailing reaction.
139. The kit according to Clause 138, wherein the one or more reagents for performing a tailing reaction comprises a terminal transferase.
140. The kit according to Clause 138 or 139, wherein the one or more reagents for performing a tailing reaction comprises dNTP tailing mix.
141. The kit according to any of Clauses 138-140, wherein the one or more reagents for performing a tailing reaction comprises a phosphatase.

Although the foregoing invention has been described in some detail by way of illustration and example for purposes of clarity of understanding, it is readily apparent to those of ordinary skill in the art in light of the teachings of this invention that certain changes and modifications may be made thereto without departing from the spirit or scope of the appended claims.

Accordingly, the preceding merely illustrates the principles of the invention. It will be appreciated that those skilled in the art will be able to devise various arrangements which, although not explicitly described or shown herein, embody the principles of the invention and are included within its spirit and scope. Furthermore, all examples and conditional language recited herein are principally intended to aid the reader in understanding the principles of the invention and the concepts contributed by the inventors to furthering the art, and are to be construed as being without limitation to such specifically recited examples and conditions. Moreover, all statements herein reciting principles, aspects, and embodiments of the invention as well as specific examples thereof, are intended to encompass both structural and functional equivalents thereof. Additionally, it is intended that such equivalents include both currently known equivalents and equivalents developed in the future, i.e., any elements developed that perform the same function, regardless of structure. The scope of the present invention, therefore, is not intended to be limited to the exemplary embodiments shown and described herein. Rather, the scope and spirit of present invention is embodied by the appended claims.

What is claimed is:

1. A method of producing an amplified double stranded deoxyribonucleic acid (dsDNA) from a nucleic acid sample wherein the dsDNA is a double stranded complementary DNA (cDNA), the method comprising:
   (a) combining:
      a nucleic acid sample;
      a reverse transcriptase;
      a single product nucleic acid primer, wherein the single product nucleic acid primer is a first strand cDNA primer;
      a template switch oligonucleotide comprising a 3' hybridization domain;
      an amplification polymerase; and
      deoxyribonucleotide triphosphates (dNTPs);
      in a reaction mixture under conditions sufficient to produce a double stranded nucleic acid complex comprising a template nucleic acid comprising messenger RNA (mRNA) and the template switch oligonucleotide hybridized to adjacent regions of a single product nucleic acid; and
   (b) amplifying from the single product nucleic acid using only the template switch oligonucleotide and the single product nucleic acid primer as primers under conditions sufficient to produce an amplified dsDNA, wherein the dsDNA is a double stranded cDNA.

2. The method according to claim 1, wherein the 3' hybridization domain hybridizes to a non-templated sequence added to the single product nucleic acid by the reverse transcriptase.

3. The method according to claim 2, wherein the non-templated sequence comprises a hetero-polynucleotide or a homo-polynucleotide.

4. The method according to claim 1, wherein the amplification polymerase is a hot-start polymerase, a thermostable polymerase or both.

5. The method according to claim 1, wherein the single product nucleic acid primer, the template switch oligonucleotide, or both comprise a 5'-non-templated sequence selected from the group consisting of: a restriction endonuclease recognition site, a primer binding site, a defined sequence, a barcode sequence, a unique molecular identifier sequence (UMI), a sequencing platform adapter construct and a combination thereof.

6. The method according to claim 1, wherein the single product nucleic acid is not purified between the combining and the amplifying.

7. The method according to claim 1, wherein the method is performed in a reaction vessel or a droplet.

8. The method according to claim 1, wherein amplifying is performed in the absence of one or more amplification primers.

9. The method according to claim 1, wherein the amplifying comprises thermocycling.

10. The method according to claim 1, wherein the reverse transcriptase is a thermo-sensitive polymerase.

11. The method according to claim 4, wherein the amplification polymerase is a hot-start polymerase.

12. The method according to claim 4, wherein the amplification polymerase is a thermostable polymerase.

13. The method according to claim 1, wherein the single product nucleic acid primer is attached to a solid support.

14. The method according to claim 1, wherein the template switch oligonucleotide is attached to a solid support.

* * * * *

UNITED STATES PATENT AND TRADEMARK OFFICE
CERTIFICATE OF CORRECTION

PATENT NO. : 11,479,806 B2
APPLICATION NO. : 16/321418
DATED : October 25, 2022
INVENTOR(S) : Kazuo Tori et al.

It is certified that error appears in the above-identified patent and that said Letters Patent is hereby corrected as shown below:

In the Specification

Replace "1 µg/µL to 5 µg/µL" with -- 1 pg/µL to 5 µg/µL -- Column 19, Line 41.

Replace "HiSeg™, MiSeg™" with -- HiSeq™, MiSeq™ -- Column 22, Line 5.

Replace "DRAQS" with -- DRAQ5 -- Column 32, Line 36.

Replace "HiSeg™ MiSeg™ and/or NextSeg™" with -- HiSeq™ MiSeq™ and/or NextSeq™ -- Column 38, Lines 56-57.

Replace "HiSeg™ MiSeg™" with -- HiSeq™ MiSeq™ -- Column 41, Line 53.

Replace "2 µl of 5 µg/ul" with -- 2 µl of 5 pg/ul -- Column 45, Line 25.

Replace "2 µl of 5 µg/ul" with -- 2 µl of 5 pg/ul -- Column 47, Line 30.

Replace "2 µl of 5 µg/ul" with -- 2 µl of 5 pg/ul -- Column 47, Line 65.

Replace "2 µl of 5 µg/ul" with -- 2 µl of 5 pg/ul -- Column 48, Line 26.

Replace "10 µg" with -- 10 pg -- Column 49, Line 35.

Replace "10 µg" with -- 10 pg -- Column 49, Line 50.

Replace "10 µg" with -- 10 pg -- Column 50, Line 20.

Replace "(55v4_1 to 55v4_12)" with -- (SSv4_1 to SSv4_12) -- Column 51, Line 25.

Replace "'5-non-tem plated sequence" with -- '5-non-templated sequence -- Column 52, Line 20.

Signed and Sealed this
Thirteenth Day of December, 2022

*Katherine Kelly Vidal*
Katherine Kelly Vidal
*Director of the United States Patent and Trademark Office*

CERTIFICATE OF CORRECTION (continued)
U.S. Pat. No. 11,479,806 B2

Replace "'5-non-tem plated sequence" with -- '5-non-templated sequence -- Column 56, Lines 16-17.

Replace "'5-non-tem plated sequence" with -- '5-non-templated sequence -- Column 56, Line 52.